United States Patent
Guy et al.

(10) Patent No.: US 10,647,702 B2
(45) Date of Patent: *May 12, 2020

(54) ARYL-SUBSTITUTED IMIDAZOLES

(71) Applicant: St. Jude Children's Research Hospital, Memphis, TN (US)

(72) Inventors: R. Kiplin Guy, Memphis, TN (US);
Yiqun Zhang, Memphis, TN (US);
Brandon Young, Memphis, TN (US);
Michael Dyer, Memphis, TN (US);
Kristin Finch, Memphis, TN (US);
Donald Bashford, Memphis, TN (US);
Nagakumar Bharatham, Memphis, TN (US); Richard Kriwacki, Memphis, TN (US); Grace Royappa, Memphis, TN (US); Lie Min, Memphis, TN (US);
Jaeki Min, Memphis, TN (US);
Antonio Ferreira, Memphis, TN (US)

(73) Assignee: St. Jude Children's Research Hospital, Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/812,605

(22) Filed: Nov. 14, 2017

(65) Prior Publication Data

US 2018/0291004 A1    Oct. 11, 2018

Related U.S. Application Data

(63) Continuation of application No. 14/991,744, filed on Jan. 8, 2016, now Pat. No. 9,822,100, which is a continuation of application No. 13/876,465, filed as application No. PCT/US2011/054368 on Sep. 30, 2011, now Pat. No. 9,266,860.

(60) Provisional application No. 61/388,287, filed on Sep. 30, 2010.

(51) Int. Cl.
| C07D 403/06 | (2006.01) |
| C07D 403/02 | (2006.01) |
| C07D 233/22 | (2006.01) |
| C07D 403/14 | (2006.01) |

(52) U.S. Cl.
CPC ......... *C07D 403/06* (2013.01); *C07D 403/14* (2013.01); *C07D 233/22* (2013.01)

(58) Field of Classification Search
CPC ... C07D 403/06; C07D 403/02; C07D 233/22
See application file for complete search history.

(56) References Cited

U.S. PATENT DOCUMENTS

| 6,617,346 | B1 | 9/2003 | Kong et al. |
| 6,734,302 | B2 | 5/2004 | Kong et al. |
| 7,132,421 | B2 | 11/2006 | Fotouhi et al. |
| 7,425,638 | B2 | 9/2008 | Haley et al. |
| 7,579,368 | B2 | 8/2009 | Fotouhi et al. |
| 9,266,860 | B2 | 2/2016 | Guy et al. |
| 9,822,100 | B2 | 11/2017 | Guy et al. |
| 2003/0153580 | A1 | 8/2003 | Kong et al. |
| 2004/0204410 | A1 | 10/2004 | Kong et al. |
| 2004/0259867 | A1 | 12/2004 | Fotouhi et al. |
| 2004/0259884 | A1 | 12/2004 | Haley et al. |
| 2005/0282803 | A1 | 12/2005 | Haley et al. |
| 2005/0288287 | A1 | 12/2005 | Fotouhi et al. |
| 2006/0211693 | A1 | 9/2006 | Fotouhi et al. |
| 2007/0129416 | A1 | 6/2007 | Ding et al. |
| 2007/0167437 | A1 | 7/2007 | Fotouhi et al. |

FOREIGN PATENT DOCUMENTS

| CA | 2813256 A1 | 4/2012 |
| EP | 2621275 A1 | 8/2013 |
| WO | WO-03/051359 A1 | 6/2003 |
| WO | WO-2005/110996 A1 | 11/2005 |
| WO | WO-2006/097261 A1 | 9/2006 |
| WO | WO-2007/063013 A1 | 6/2007 |
| WO | WO-2008/014216 A1 | 1/2008 |
| WO | WO-2008/065068 A2 | 6/2008 |
| WO | WO-2009/047161 A1 | 4/2009 |
| WO | WO-2010/028858 A1 | 3/2010 |
| WO | WO-2012/045018 A1 | 4/2012 |
| WO | WO-2013/106643 A2 | 7/2013 |
| WO | WO-2015/184383 A1 | 12/2015 |

OTHER PUBLICATIONS

Laurie, N.A. et al., Inactivation of the p53 pathway in retinoblastoma. Nature. 2006; 444:61-6.
Reed, D. et al., Identification and Characterization of the First Small Molecule Inhibitor of MDMX. J Biol Chem. 2010; 285(14):10786-96.
Vara, B.A. et al., Organocatalytic, Diastereo- and Enantioselective Synthesis of Nonsymmetric cis-Stilbene Diamines: A Platform for the Preparation of Single-Enantiomer cis-Imidazolines for Protein-Protein Inhibition. J Org Chem. 2014; 79(15):693-38.
Vassilev, L.T. et al., In Vivo Activation of the p53 Pathway by Small-Molecule Antagonists of MDM2. Science. 2004; 303:844-8.
Verma, R. et al., DNA Damage Response to the Mdm2 Inhibitro Nutlin-3. Biochem Pharmacol. 2010; 79:565-74.
PubChem-CID-70985746. Create Date: Mar. 21, 2013, p. 3 (10 pages).
Office Action dated Sep. 11, 2017 by the Canadian Patent Office for Patent Application No. 2813256, which was filed on Mar. 28, 2013 (Inventor—Guy et al.; Applicant—St. Jude Children's Research Hospital) (4 pages).

(Continued)

*Primary Examiner* — Samira J Jean-Louis
(74) *Attorney, Agent, or Firm* — Ballard Spahr LLP

(57) ABSTRACT

The compounds of the invention are antagonists of MDM2 and MDMX, with excellent specificity for MDM2 and MDMX over other proteins, and with selective binding affinity to MDMX over MDM2. The compounds can therefore regulate p53 activity and treat a variety of cancers. This abstract is intended as a scanning tool for purposes of searching in the particular art and is not intended to be limiting of the present invention.

24 Claims, 4 Drawing Sheets

(56) References Cited

OTHER PUBLICATIONS

Extended European Search Report dated Feb. 12, 2014 for application EP 11830023.5, filed on Sep. 30, 2011 and published as EP 2621275 dated Aug. 7, 2013 (Applicant—St. Jude's Children's Research Hospital // Inventor—Guy, et al.) (7 pages).
Response to the Communication Pursuant to Rules 70(2) and 70a(2) EPC filed on Sep. 10, 2014 for application EP 11830023.5, filed on Sep. 30, 2011 and published as EP 2621275 dated Aug. 7, 2013 (Applicant—St. Jude's Children's Research Hospital // Inventor—Guy, et al.) (3 pages).
Communication Pursuant to Article 94(3) EPC dated Apr. 2, 2015 for application EP 11830023.5, filed on Sep. 30, 2011 and published as EP 2621275 dated Aug. 7, 2013 (Applicant—St. Jude's Children's Research Hospital // Inventor—Guy, et al.) (4 pages).
Response to Communication Pursuant to Article 94(3) EPC filed on Aug. 31, 2015 for application EP 11830023.5, filed on Sep. 30, 2011 and published as EP 2621275 dated Aug. 7, 2013 (Applicant—St. Jude's Children's Research Hospital // Inventor—Guy, et al.) (3 pages).
Communication Pursuant to Article 94(3) EPC dated Jan. 15, 2016 for application EP 11830023.5, filed on Sep. 30, 2011 and published as EP 2621275 dated Aug. 7, 2013 (Applicant—St. Jude's Children's Research Hospital // Inventor—Guy, et al.) (4 pages).
Communication Pursuant to Article 94(3) EPC dated Nov. 14, 2016 by the European Patent Office for EP Application No. 11830023.5, which was filed on Sep. 30, 2011 and published as 2621275 dated Aug. 7, 2013 (Applicant—St. Jude Children's Research Hospital) (4 pages).
Intention to Grant dated Sep. 21, 2017 by the European Patent Office for Patent Application No. 11830023.5, which was filed on Sep. 30, 2011 and published as EP 2621275 dated Aug. 7, 2013 (Inventor—Guy et al.; Applicant—St. Jude Children's Research Hospital) (6 pages).
International Search Report issued by the International Searching Authority dated Mar. 8, 2012 for PCT/US2011/054368 filed on Sep. 30, 2011 and published as WO 2012/045018 dated Apr. 5, 2012 (Applicant—St. Jude Children's Research Hospital; Inventor—Guy et al.) (2 pages).
Written Opinion issued by the International Searching Authority dated Mar. 8, 2012 for PCT/US2011/054368 filed on Sep. 30, 2011 and published as WO 2012/045018 dated Apr. 5, 2012 (Applicant—St. Jude Children's Research Hospital; Inventor—Guy et al.) (7 pages).
International Preliminary Report on Patentability issued by the International Searching Authority dated Sep. 21, 2012 for PCT/US2011/054368 filed on Sep. 30, 2011 and published as WO 2012/045018 dated Apr. 5, 2012 (Applicant—St. Jude Children's Research Hospital; Inventor—Guy et al.) (3 pages).
Restriction Requirement dated Nov. 25, 2013 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (12 pages).
Response to Restriction Requirement filed Jan. 27, 2014 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (24 pages).
Non-Final Office Action dated Apr. 7, 2014 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (13 pages).
Response to Non-Final Office Action filed Oct. 7, 2014 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (25 pages).
Final Office Action dated Dec. 10, 2014 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (10 pages).
Response to Final Office Action filed Jan. 5, 2015 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (27 pages).
Notice of Allowance dated Oct. 9, 2015 for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.) (11 pages).
Issue Notification dated Feb. 3, 2016 by the U.S. Patent and Trademark Office for U.S. Appl. No. 13/876,465, filed Aug. 9, 2013 now U.S. Pat. No. 9,266,860 dated Feb. 23, 2016 (Applicant—St. Jude Children's Research Hospital; Inventor—Guy et al.)(1 page).
Preliminary Amendment filed Jan. 8, 2016 with the U.S. Patent and Trademark Office for U.S. Appl. No. 14/991,744, filed Jan. 8, 2016 now U.S. Pat. No. 9,822,100 dated Nov. 21, 2017 (Inventor—Guy et al.; Applicant—St. Jude Children's Research Hospital) (13 pages).
Non-Final Office Action dated Sep. 9, 2016 by the U.S. Patent and Trademark Office for U.S. Appl. No. 14/991,744, filed Jan. 8, 2016 now U.S. Pat. No. 9,822,100 dated Nov. 21, 2017 (Inventor—Guy et al.; Applicant—St. Jude Children's Research Hospital) (14 pages).
Response to Non-Final Office Action filed Mar. 9, 2016 with the U.S. Patent and Trademark Office for U.S. Appl. No. 14/991,744, filed Jan. 8, 2016 now U.S. Pat. No. 9,822,100 dated Nov. 21, 2017 (Inventor—Guy et al.; Applicant—St. Jude Children's Research Hospital) (21 pages).
Final Office Action dated May 31, 2017 by the U.S. Patent and Trademark Office for U.S. Appl. No. 14/991,744, filed Jan. 8, 2016 now U.S. Pat. No. 9,822,100 dated Nov. 21, 2017 (Inventor—Guy et al.; Applicant—St. Jude Children's Research Hospital) (11 pages).
Response to Final Office Action filed Jul. 31, 2017 with the U.S. Patent and Trademark Office for U.S. Appl. No. 14/991,744, filed Jan. 8, 2016 U.S. Pat. No. 9,822,100 dated Nov. 21, 2017 (Inventor—Guy et al.; Applicant—St. Jude Children's Research Hospital) (31 pages).
Notice of Allowance dated Aug. 21, 2017 by the U.S. Patent and Trademark Office for U.S. Appl. No. 14/991,744, filed Jan. 8, 2016 now U.S. Pat. No. 9,822,100 dated Nov. 21, 2017 (Inventor—Guy et al.; Applicant—St. Jude Children's Research Hospital) (10 pages).
Issue Notification dated Nov. 1, 2017 by the U.S. Patent and Trademark Office for U.S. Appl. No. 14/991,744, filed Jan. 8, 2016 now U.S. Pat. No. 9,822,100 dated Nov. 21, 2017 (Inventor—Guy et al.; Applicant—St. Jude Children's Research Hospital) (1 page).
International Search Report and Written Opinion dated Aug. 12, 2015 by the International Searching Authority for Patent Application No. PCT/US2015/033370, which was filed on May 29, 2015 and published as WO 2015/184383 dated Dec. 3, 2015 (Inventor—R.K. Guy; Applicant—St. Jude Children's Research Hospital) (7 pages).
International Preliminary Report on Patentability dated Nov. 29, 2016 by the International Searching Authority for Patent Application No. PCT/US2015/033370, which was filed on May 29, 2015 and published as WO 2015/184383 dated Dec. 3, 2015 (Inventor—R.K. Guy; Applicant—St. Jude Children's Research Hospital) (6 pages).
U.S. Appl. No. 61/388,287, filed Sep. 30, 2010, R.K. Guy et al. (St. Jude Children's Res. Hosp.)
U.S. Appl. No. 13/388,287 (U.S. Pat. No. 9,266,860), filed Sep. 30, 2011 (Feb. 23, 2016), R.K. Guy et al. (St. Jude Children's Res. Hosp.)
U.S. Appl. No. 14/991,744 (U.S. Pat. No. 9,822,100), filed Jan. 8, 2016 (Nov. 21, 2017), R.K. Guy et al. (St. Jude Children's Res. Hosp.)
U.S. Appl. No. 62/004,720, filed May 29, 2014 R.K. Guy (St. Jude Children's Res. Hosp.)
2813256 (2813256), Mar. 28, 2011, R.K. Guy et al. (St. Jude Children's Res. Hosp.)
11830023.5 (EP 2621275), Sep. 30, 2011 (Aug. 7, 2013), R.K. Guy et al. (St. Jude Children's Res. Hosp.)
PCT/US2011/054368 (WO 2012/045018), Sep. 30, 2011 (Apr. 5, 2012), R.K. Guy et al. (St. Jude Children's Res. Hosp.)
PCT/US2015/033370 (WO 2015/184383), May 29, 2015 (Dec. 3, 2015), R.K. Guy (St. Jude Children's Res. Hosp.)

Ar₁, Ar₂ = substituted phenyl, hetero-aromatic rings
symmetric or non-symmetric aryl groups
Ar₃ = mono-, di-substituted phenyl, naphtyl, indoyl

ARYL-SUBSTITUTED IMIDAZOLES

CROSS-REFERENCE TO RELATED APPLICATIONS

This application is a Continuation of U.S. application Ser. No. 14/991,744, filed on Jan. 8, 2016, which is a Continuation of U.S. application Ser. No. 13/876,465, filed on Aug. 9, 2013, which is a United States National Phase of International Application No. PCT/US2011/54368, filed on Sep. 30, 2011, which claims the benefit of U.S. Application No. 61/388,287, filed Sep. 30, 2010, which is hereby incorporated by reference in its entirety.

BACKGROUND

The p53 protein is required for normal embryogenesis, tumor suppression, and cellular response to DNA damage. Activity of p53 not only guards cellular integrity but also prevents propagation of permanently damaged cells by inducing growth arrest or apoptosis. p53 is the most frequently inactivated protein in human cancer. A mutation of p53 is found in almost 50% of human cancers.

Under normal conditions, cellular regulator MDM2 controls p53 through an autoregulatory feedback loop. p53 activates MDM2 expression, leading to the expression of p53. MDM2 mediates ubiquitin-dependent degradation of p53 and is also a cofactor for E2F, which is involved in cell cycle regulation. The feedback control loop ensures that both MDM2 and p53 are kept at a low level in normal proliferating cells.

Overexpression of MDM2 has been found in many human malignancies. Accordingly, activation of the p53 pathway through inhibition of MDM2 has been proposed as a cancer therapy. Several studies have shown that p53 function can be reactivated by disrupting MDM2-p53 interaction, or by suppressing MDM2 expression. A variety of small molecules have been shown to bind p53, including Nutlin-3 and MI-219.

Overexpression of MDMX, which is structurally similar to MDM2, has also been found in many human malignancies. MDMX binds MDM2 and stimulates MDM2 degradation of p53. Only a few MDMX inhibitors have been identified to date. Many small molecules that inhibit MDM2, such as Nutlin, are virtually inactive in MDMX inhibition and fail to induce MDMX degradation in tumor cells. p53 activation by many small molecules is compromised in cells that overexpress MDMX. Small molecules that target both MDM2 and MDMX, and those that show preference for MDMX, would therefore be of great benefit in regulating p53 activity.

SUMMARY

The compounds of the invention are antagonists of MDM2 and MDMX, and can exhibit specificity for MDM2 and MDMX over other proteins, and can also exhibit improved binding affinity for MDMX over MDM2, relative to the ratio of binding for nutlin-3a and improved overall affinity for MDMX relative to nutlin-3a. The compounds can therefore regulate p53 activity through affecting function of MDMX and treat a variety of cancers.

In one aspect, the invention relates to compounds having the formula:

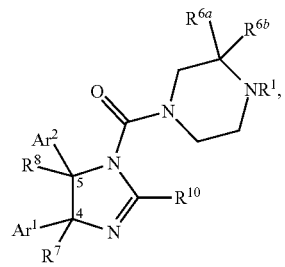

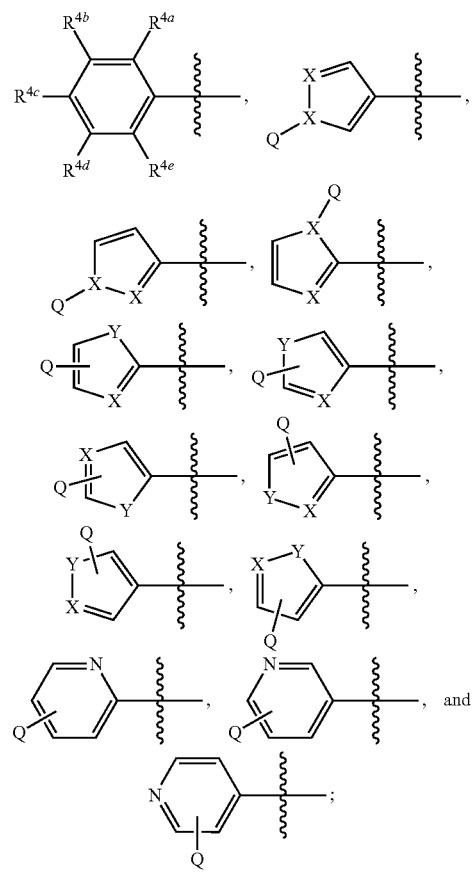

wherein $Ar^1$ and $Ar^2$ are independently selected from:

wherein each X is independently selected from N and CH; wherein each Y is independently selected from S and O; wherein each Q is independently selected from hydrogen, halogen, nitro, and $C_1$-$C_4$ alkyl; wherein $Ar^1$ and $Ar^2$ are different when both $R^7$ and $R^8$ are hydrogen; wherein $Ar^1$ and $Ar^2$ have a cis relationship; wherein $R^1$ is selected from hydrogen and $C_1$-$C_4$ alkyl and substituted with 0-2 groups selected from halogen, alkoxy, carboxymethyl, carboxyethyl, trifluoromethyl, trifluoromethoxy, and —$SO_2Me$; wherein $R^2$, $R^3$, and $R^5$ are independently selected from hydrogen, halogen, methyl, ethyl, n-propyl, i-propyl, n-butyl, i-butyl, t-butyl, trifluoromethyl, trifluoroethyl, methoxy, ethoxy, n-propoxyl, i-propoxyl, n-butoxyl, i-butoxyl, and t-butoxyl; wherein $R^{4a}$-$R^{4e}$ are independently selected from hydrogen, halogen, alkyl, trifluoromethyl, trifluoromethoxy, alkoxy, and —$SO_2Me$; wherein $R^{6a}$ and $R^{6b}$ are independently selected from hydrogen and $C_1$-$C_4$ alkyl, or wherein $R^{6a}$ and $R^{6b}$ together comprise =O; wherein $R^7$ and $R^8$ are independently selected from hydrogen, methyl, and ethyl; wherein $R^9$ is selected from hydrogen, halogen, methyl, ethyl, methoxy, ethoxy, carboxymethyl, and carboxyethyl; wherein $R^{10}$ is selected from $C_1$-$C_4$ alkyl and $Ar^3$; and wherein $Ar^3$ is selected from:

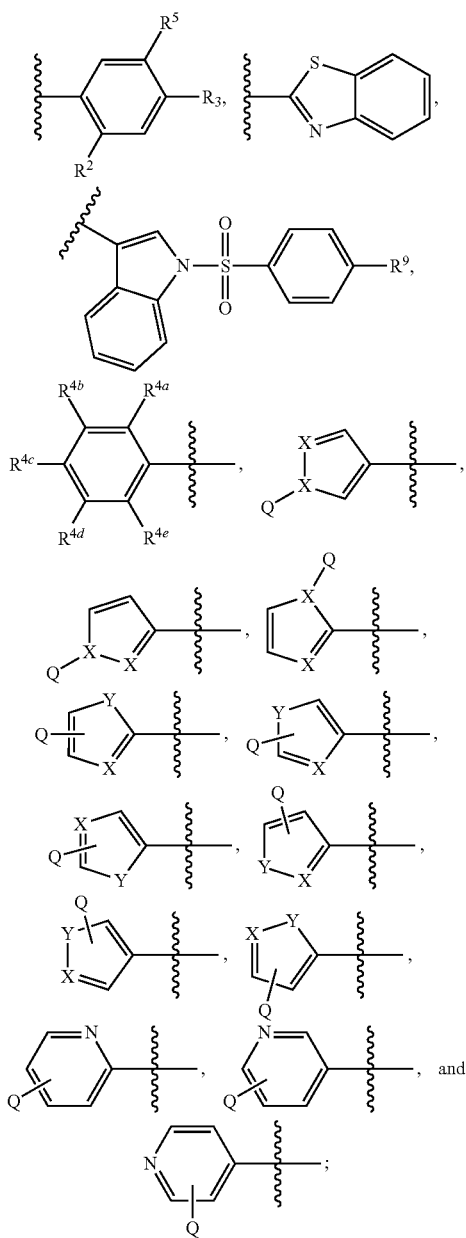

or a pharmaceutically acceptable salt thereof.

Also disclosed are pharmaceutically acceptable salts of the compounds, and pharmaceutical compositions comprising the compounds.

Also disclosed are treatment methods comprising administering to a subject in need thereof a therapeutically effective amount of a disclosed compound to treat a cell proliferative disorder.

Also disclosed are methods of making the disclosed compounds.

Also disclosed are the products of the disclosed methods of making.

BRIEF DESCRIPTION OF THE DRAWINGS

FIG. 4a shows aldehyde building block I. FIG. 4b shows diamine building block II.

Figure 1A:
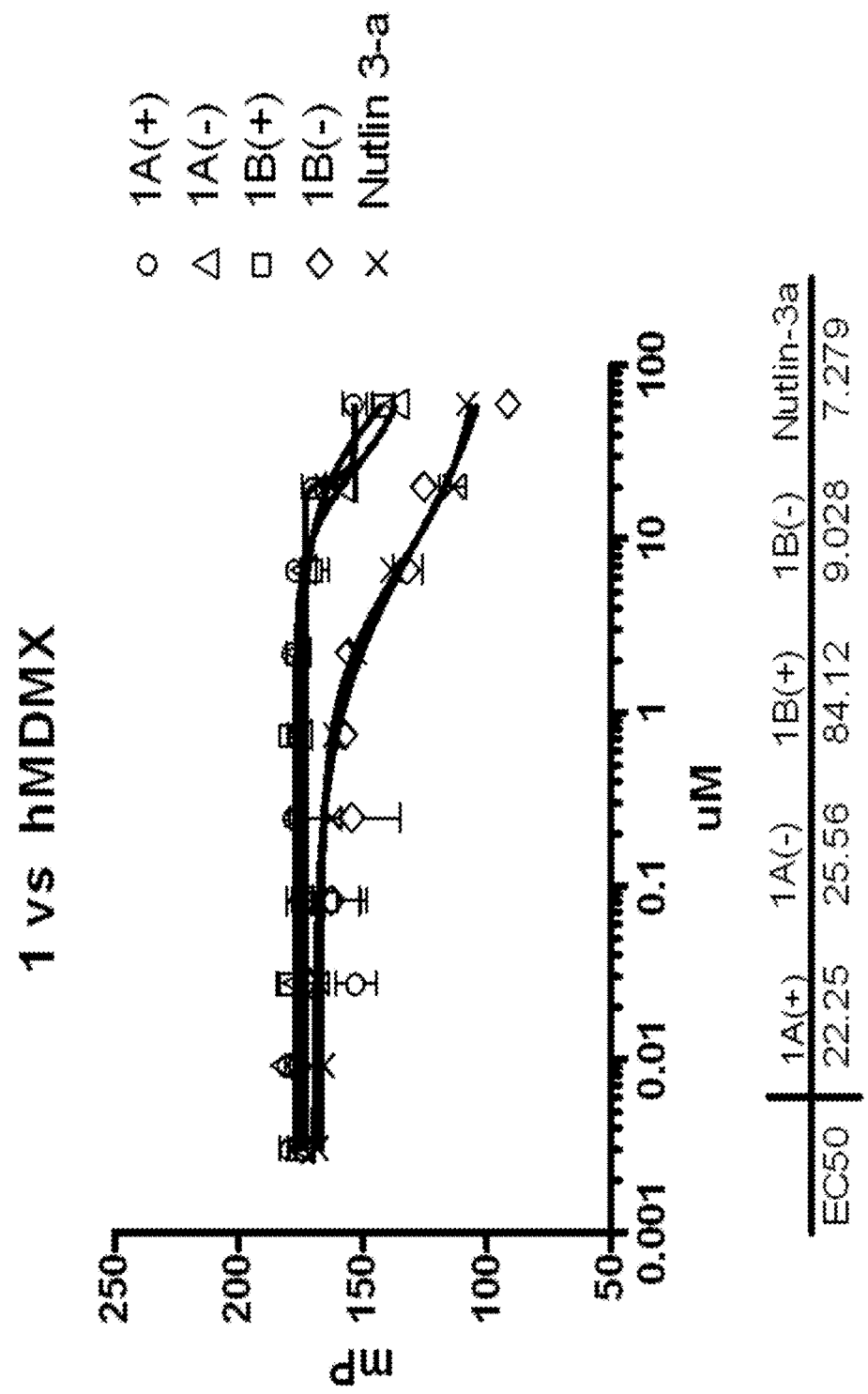
FIGS. 1A and 1B show competitive binding curves of compounds 1A and 1B (see Examples) against hMDMX (FIG. 1A) and hMDM2 (FIG. 1B). $EC_{50}$ was given in μM. The stereochemistry of each isomer was assigned based on the optical rotation compared to that of Nutlin-3a ([α]=−151.7° in Methanol, 18.5° C.).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for positive allosteric modulation of metabotropic glutamate receptor activity prior to the administering step. In some aspects of the disclosed method, the subject has been diagnosed with a need for partial agonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a disorder of cellular proliferation prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_5O$ refers to the concentration of agonist that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where A' is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an interger from 1 to 500.

"Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A¹S(O)A², where A¹ and A² can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; NO$_2$; —CN; N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°C(O)NR°)$_2$; —N(R°)C(S)NR°)$_2$; —(CH$_2$)$_{0-4}$N(R°)C(O)OR°); —N(R°)N(R°)C(O)R°); —N(R°)N(R°)C(O)NR°)$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; (CH$_2$)$_{0-4}$C(O)NR°)$_2$; —C(S)NR°)$_2$; —C(S)SR°; —SC(S)SR°, —(CH$_2$)$_{0-4}$OC(O)NR°)$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°)$_2$; —(CH$_2$)$_{0-4}$S(O)R°; —N(R°)S(O)$_2$NR°)$_2$; —N(R°)S(O)$_2$R°; —N(OR°)R°; —C(NH)NR°)$_2$; —P(O)$_2$R°; —P(O)R°)$_2$; —OP(O)R°)$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)$_{0-2}$OR●, —(CH$_2$)$_{0-2}$CH(OR●)$_2$; —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —R$^{\bullet}$, -(haloR$^{\bullet}$), —OH, —OR$^{\bullet}$, —O(halo)$_n$, —CN, —C(O)OH, —C(O)OR$^{\bullet}$, —NH$_2$, —NHR$^{\bullet}$, —NR$^{\bullet}_2$, or —NO$_2$, wherein each R$^{\bullet}$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

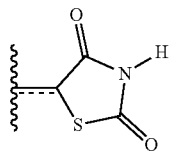

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkyl-carboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, achiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (ee). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

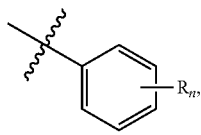

which is understood to be equivalent to a formula:

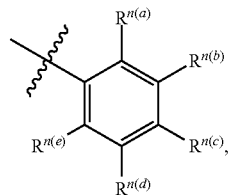

wherein n is typically an integer. That is, $R^n$ is understood to represent five independent substituents, $R^{n(a)}$, $R^{n(b)}$, $R^{n(c)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

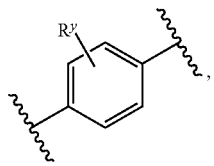

wherein $R^y$ represents, for example, 0-2 independent substituents selected from $A^1$, $A^2$, and $A^3$, which is understood to be equivalent to the groups of formulae:

wherein $R^y$ represents 0 independent substituents

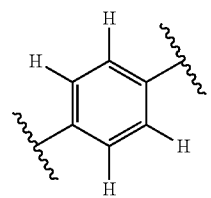

wherein $R^y$ represents 1 independent substituent

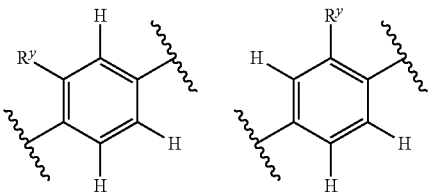

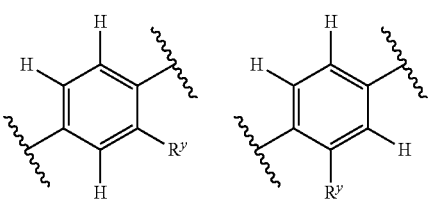

wherein $R^y$ represents 2 independent substituents

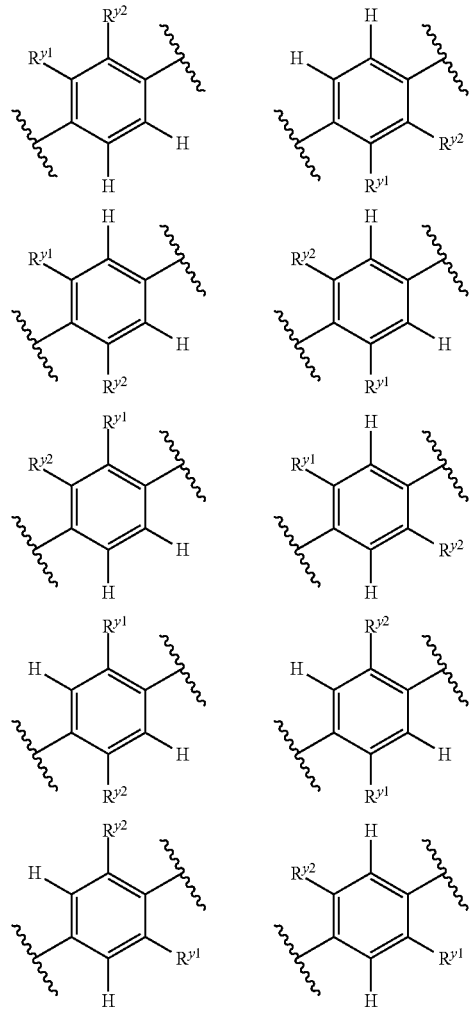

-continued

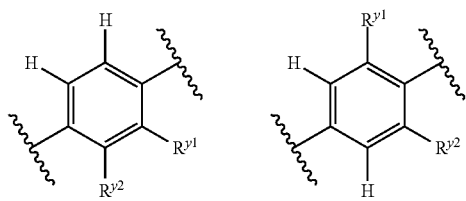

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

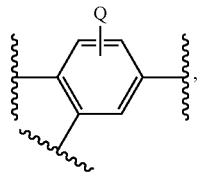

wherein, for example, Q comprises three substituents independently selected from hydrogen and A, which is understood to be equivalent to a formula:

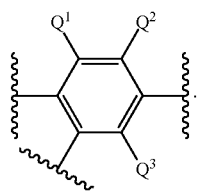

Again, by "independent substituents," it is meant that each Q substituent is independently defined as hydrogen or A, which is understood to be equivalent to the groups of formulae:
wherein Q comprises three substituents independently selected from H and A

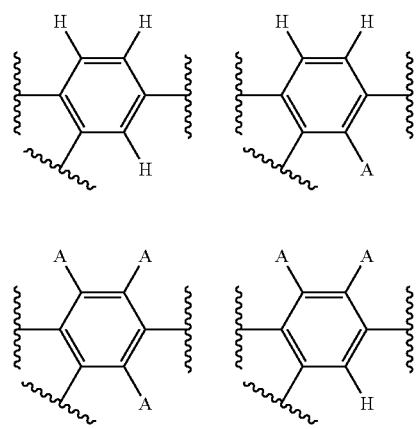

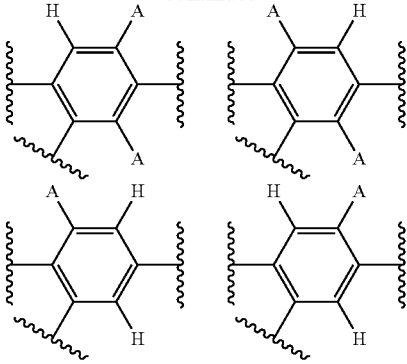

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

The compounds of the invention are useful in treating or controlling cell proliferative disorders, in particular oncological disorders, such as cancer. The compounds and pharmaceutical compositions containing the compounds can be useful in the treatment or control of solid tumors, such as breast, colon, lung and prostate tumors.

A. Compounds

In one aspect, the invention relates to compounds having the formula:

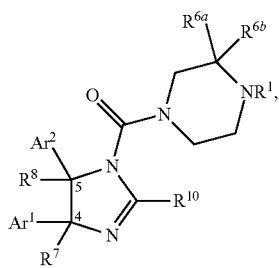

wherein $Ar^1$ and $Ar^2$ are independently selected from:

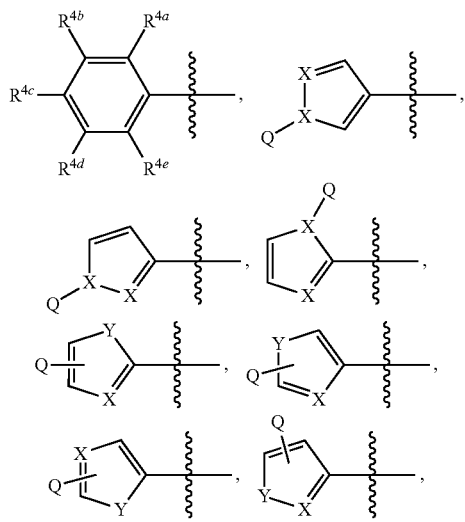

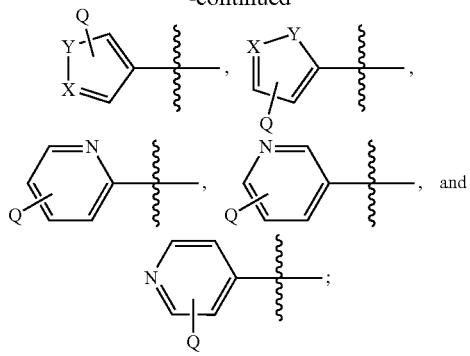

wherein each X is independently selected from N and CH; wherein each Y is independently selected from S and O; wherein each Q is independently selected from hydrogen, halogen, nitro, and $C_1$-$C_4$ alkyl; wherein $Ar^1$ and $Ar^2$ are different when both $R^7$ and $R^8$ are hydrogen; wherein $Ar^1$ and $Ar^2$ have a cis relationship; wherein $R^1$ is selected from hydrogen and $C_1$-$C_4$ alkyl and substituted with 0-2 groups selected from halogen, alkoxy, carboxymethyl, carboxyethyl, trifluoromethyl, trifluoromethoxy, and —$SO_2$Me; wherein $R^2$, $R^3$, and $R^5$ are independently selected from hydrogen, halogen, methyl, ethyl, n-propyl, i-propyl, n-butyl, i-butyl, t-butyl, trifluoromethyl, trifluoroethyl, methoxy, ethoxy, n-propoxyl, i-propoxyl, n-butoxyl, i-butoxyl, and t-butoxyl; wherein $R^{4a}$-$R^{4e}$ are independently selected from hydrogen, halogen, alkyl, trifluoromethyl, trifluoromethoxy, alkoxy, and —$SO_2$Me; wherein $R^{6a}$ and $R^{6b}$ are independently selected from hydrogen and $C_1$-$C_4$ alkyl, or wherein $R^{6a}$ and $R^{6b}$ together comprise =O; wherein $R^7$ and $R^8$ are independently selected from hydrogen, methyl, and ethyl; wherein $R^9$ is selected from hydrogen, halogen, methyl, ethyl, methoxy, ethoxy, carboxymethyl, and carboxyethyl; wherein $R^{10}$ is selected from $C_1$-$C_4$ alkyl and $Ar^3$; and wherein $Ar^3$ is selected from:

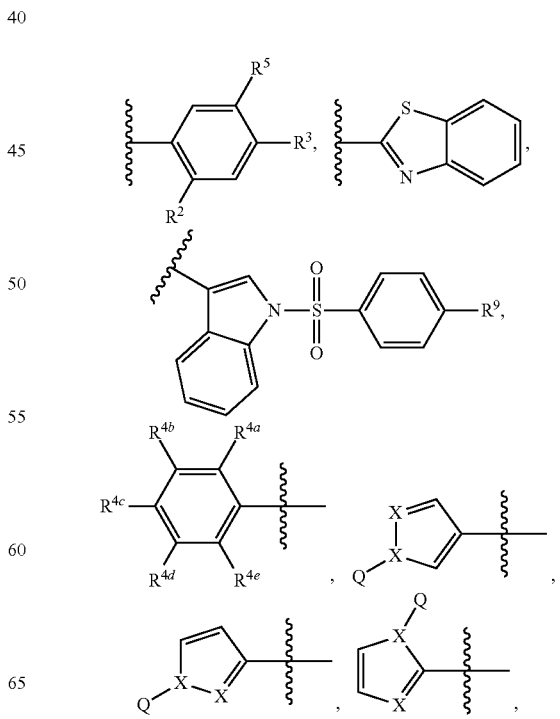

-continued

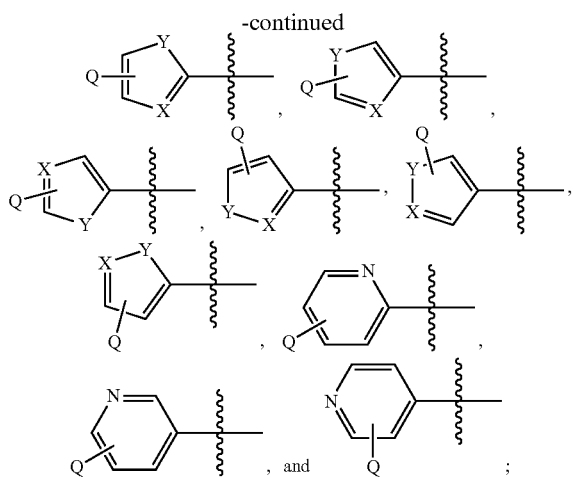

or a pharmaceutically acceptable salt thereof.

In a further aspect, $R^{10}$ is $Ar^3$ selected from:

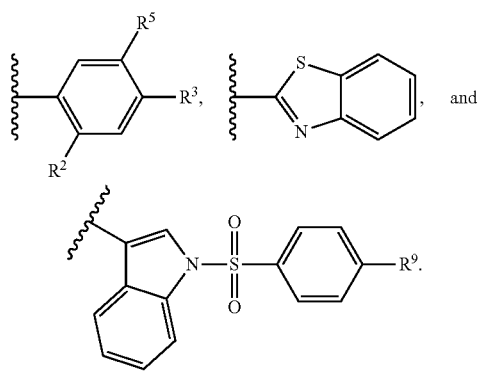

In a further aspect, $R^{10}$ is:

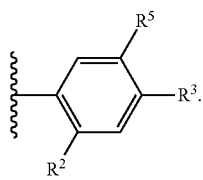

In a further aspect, $R^{10}$ is $C_1$-$C_4$ alkyl.

In further aspects, the invention relates to compounds having the formula:

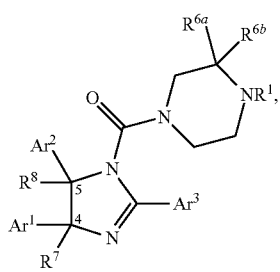

wherein $Ar^1$ and $Ar^2$ are independently selected from:

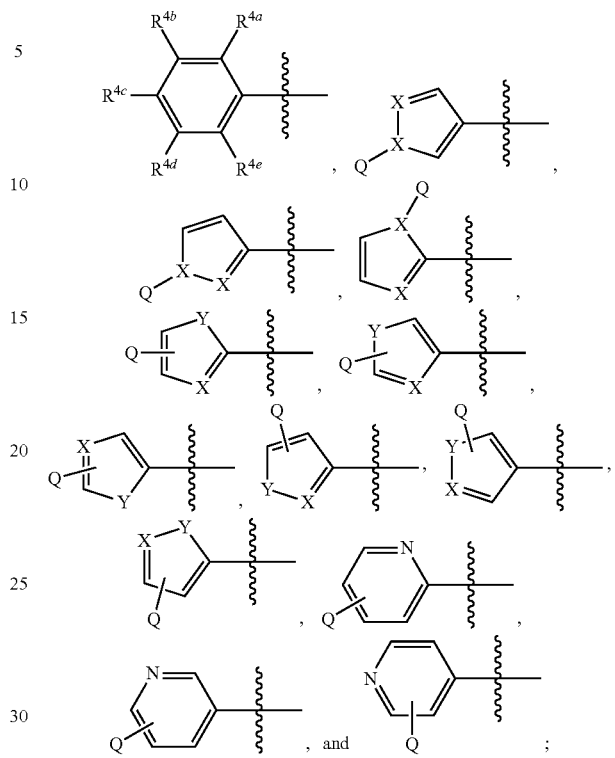

wherein each X is independently selected from N and CH; wherein each Y is independently selected from S and O; wherein each Q is independently selected from hydrogen, halogen, nitro, and $C_1$-$C_4$ alkyl; wherein $Ar^1$ and $Ar^2$ are different when both $R^7$ and $R^8$ are hydrogen; wherein $Ar^1$ and $Ar^2$ have a cis relationship; wherein $Ar^3$ is selected from:
$C_1$-$C_4$ alkyl,

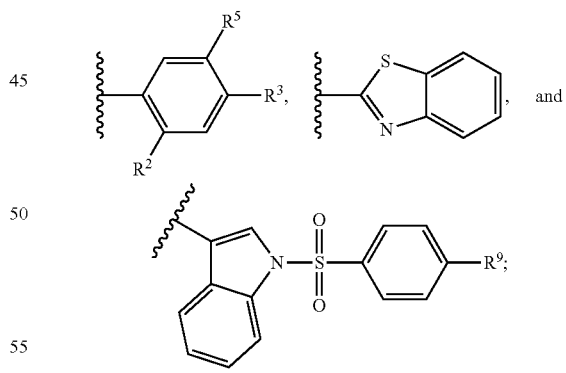

wherein $R^1$ is selected from hydrogen and $C_1$-$C_4$ alkyl and substituted with 0-2 groups selected from halogen, alkoxy, carboxymethyl, carboxyethyl, trifluoromethyl, trifluoromethoxy, and —$SO_2$Me; wherein $R^2$, $R^3$, and $R^5$ are independently selected from hydrogen, halogen, methyl, ethyl, n-propyl, i-propyl, n-butyl, i-butyl, t-butyl, trifluoromethyl, trifluoroethyl, methoxy, ethoxy, n-propoxyl, i-propoxyl, n-butoxyl, i-butoxyl, and t-butoxyl; wherein $R^{4a}$-$R^{4e}$ are independently selected from hydrogen, halogen, alkyl, trifluoromethyl, trifluoromethoxy, alkoxy, and —SO$_2$Me; wherein R$^{6a}$ and R$^{6b}$ are independently selected from hydrogen and C$_1$-C$_4$ alkyl, or wherein R$^{6a}$ and R$^{6b}$ together comprise =O; wherein R$^7$ and R$^8$ are independently selected from hydrogen, methyl, and ethyl; and wherein R$^9$ is selected from hydrogen, halogen, methyl, ethyl, methoxy, ethoxy, carboxymethyl, and carboxyethyl; or a pharmaceutically acceptable salt thereof.

In a further aspect, R$^7$ and R$^8$ are the same. In a further aspect, R$^{6a}$ and R$^{6b}$ are both hydrogen. In a further aspect, R$^{6a}$ and R$^{6b}$ together comprise =O. In a further aspect, the absolute stereochemistry at position 4 and 5 is R and S, respectively. In a further aspect, the absolute stereochemistry at position 4 and 5 is S and R, respectively. In a further aspect, AP is:

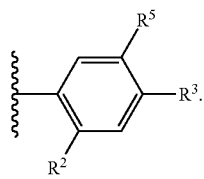

In further aspects, the compounds have the formula:

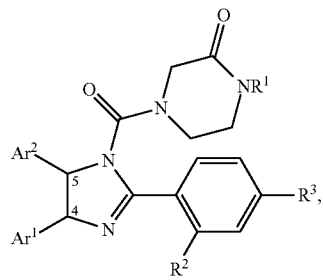

wherein Ar$^1$ and Ar$^2$ are independently selected from:

a)

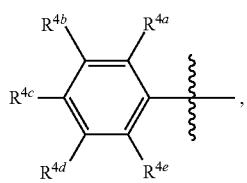

wherein R$^{4a}$-R$^{4e}$ are independently selected from hydrogen (—H), halogen (F, Cl, Br, I), alkyl, alkoxy, trifluoromethyl (—CF$_3$) methoxy (—OCH$_3$), and trifluoromethoxy (—OCF$_3$);

b)

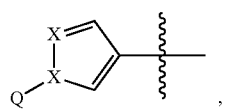

c)

d)

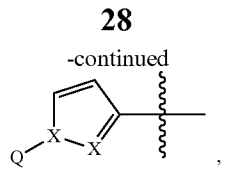

e)

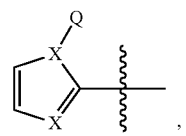

f)

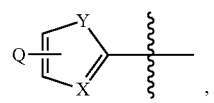

g)

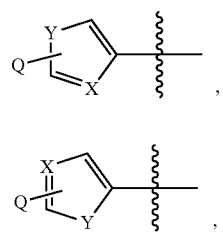

h)

i)

j)

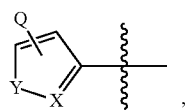

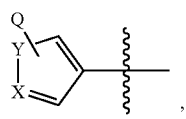

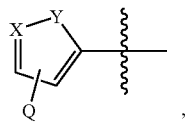

wherein each X is independently N or CH; and wherein each Y is independently S or O;

k)

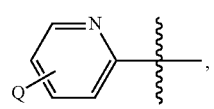

l)

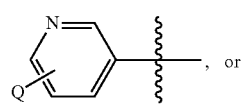, or m)

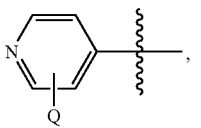, wherein Q is hydrogen or C1-C4 alkyl; wherein $Ar^1$ and $Ar^2$ are different; wherein $R^1$ is hydrogen or C1-C4 alkyl; wherein $R^2$ is hydrogen, halogen, —$CH_3$, —$CF_3$, —$OCH_3$, —$OCH(CH_3)_2$, or —$OC(CH_3)_3$; wherein $R^3$ is hydrogen, halogen, —$CH_3$, —$CF_3$, —$OCH_3$, —$OCH(CH_3)_2$, or —$OC(CH_3)_3$ and wherein the absolute stereochemistry at position 4 and 5 is R and S, respectively; or S and R, respectively; or a pharmaceutically acceptable salt thereof.

$Ar^1$ and $Ar^2$ are different substituents, and are preferably arranged in a cis, or syn configuration with respect to one another. Likewise, the hydrogen atoms at positions 4 and 5 are also preferably cis or syn with respect to one another. In this arrangement, the absolute stereochemistry at position 4 and 5 is R and S, respectively; or S and R, respectively. Known compounds, such as Nutlin, feature identical $Ar^1$ and $Ar^2$ substituents, which may have an effect on their relative lack of MDMX binding.

In certain aspects, the compounds of the invention feature asymmetrical, or different, $Ar^1$ and $Ar^2$ substituents, which is believed to affect their specificity of MDMX binding over MDM2 binding. More specifically, when both $R^7$ and $R^8$ are hydrogen, $Ar^1$ and $Ar^2$ are different.

In some aspects, each $Ar^1$ and $Ar^2$ is independently a substituent having the formula:

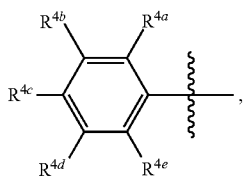

wherein $R^{4a}$-$R^{4e}$ are independently selected from hydrogen, halogen, alkyl, trifluoromethyl, trifluoromethoxy, and alkoxy. In certain examples, $R^{4c}$ is hydrogen on one, but not both Ar substituents. That is, one $R^{4c}$ substituent is hydrogen, while the other $R^{4c}$ substituent is selected from halogen, alkyl, trifluoromethyl, trifluoromethoxy, and alkoxy. That is, in certain aspects, $Ar^1$ and $Ar^2$ are not both para substituted.

In some aspects, each $Ar^1$ and $Ar^2$ is a substituent having formula (a), $R^{4a}$ and $R^{4e}$ are each hydrogen; and $R^{4b}$-$R^{4d}$ are independently selected from hydrogen, halogen, alkyl, trifluoromethyl, trifluoromethoxy, and alkoxy.

$R^1$ can be hydrogen or a C1-C4 alkyl group, such as methyl, ethyl, propyl, butyl, or isopropyl. $R^1$ is preferably hydrogen. Acid additions salts can protonate this hydrogen and/or the nitrogen of the imidazole ring to form a pharmaceutically acceptable salt, as discussed below.

In further aspects, the compounds have the formula:

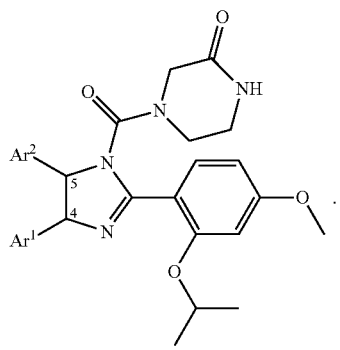

Specific examples of the compounds include, without limitation, 4-((4S,5R)-4-(4-chlorophenyl)-2-(2-isopropoxy-4-methoxyphenyl)-5-(m-tolyl)-4,5-dihydro-1H-imidazole-1-carbonyl)piperazin-2-one; 4-((4R,5S)-4-(4-chlorophenyl)-2-(2-isopropoxy-4-methoxyphenyl)-5-(m-tolyl)-4,5-dihydro-1H-imidazole-1-carbonyl)piperazin-2-one; 4-((4S,5R)-5-(4-chlorophenyl)-2-(2-isopropoxy-4-methoxyphenyl)-4-(m-tolyl)-4,5-dihydro-1H-imidazole-1-carbonyl)piperazin-2-one; and 4-((4R,5S)-5-(4-chlorophenyl)-2-(2-isopropoxy-4-methoxyphenyl)-4-(m-tolyl)-4,5-dihydro-1H-imidazole-1-carbonyl)piperazin-2-one.

1. Ar1 and Ar2 Groups

In one aspect, each of $Ar^1$ and $Ar^2$ is independently selected from:

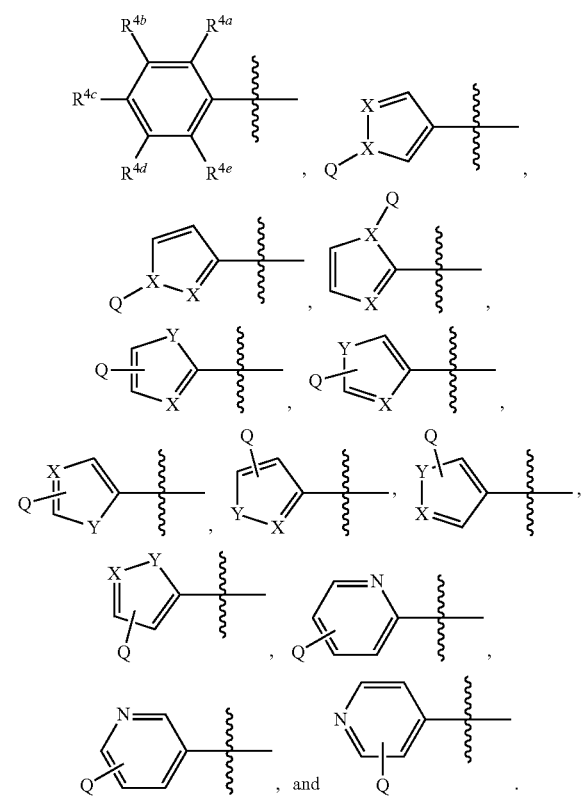

It is contemplated that the selection group can be further limited, if desired.

In various aspects, each X is independently selected from N and CH. In one aspect, X is N. In a further aspect, X is CH. In various aspects, each Y is independently selected from S and O. In one aspect, Y is S. In a further aspect, Y is O. In various aspects, each Q is independently selected from hydrogen, halogen, nitro, and $C_1$-$C_4$ alkyl. For example, Q can be selected from hydrogen and alkyl.

In various aspects, $Ar^1$ and $Ar^2$ are different when both $R^7$ and $R^8$ are hydrogen. In various aspects, $Ar^1$ and $Ar^2$ have a cis relationship; that is, both $Ar^1$ and $Ar^2$ are substituted on the same face of the central ring.

2. Ar3 Groups
In one aspect, wherein $Ar^3$ is selected from:

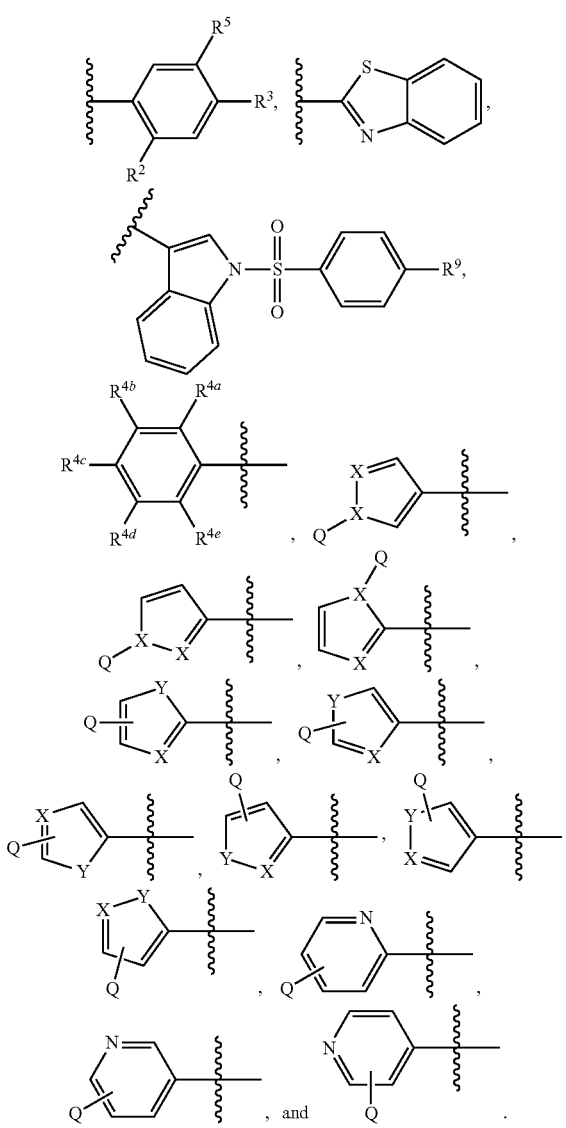

In a further aspect, $Ar^3$ is selected from:
$C_1$-$C_4$ alkyl,

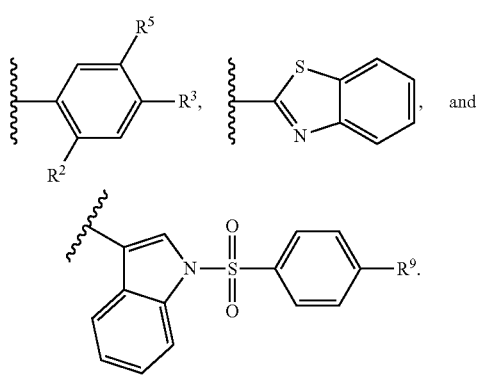

In a further aspect, $Ar^3$ selected from:

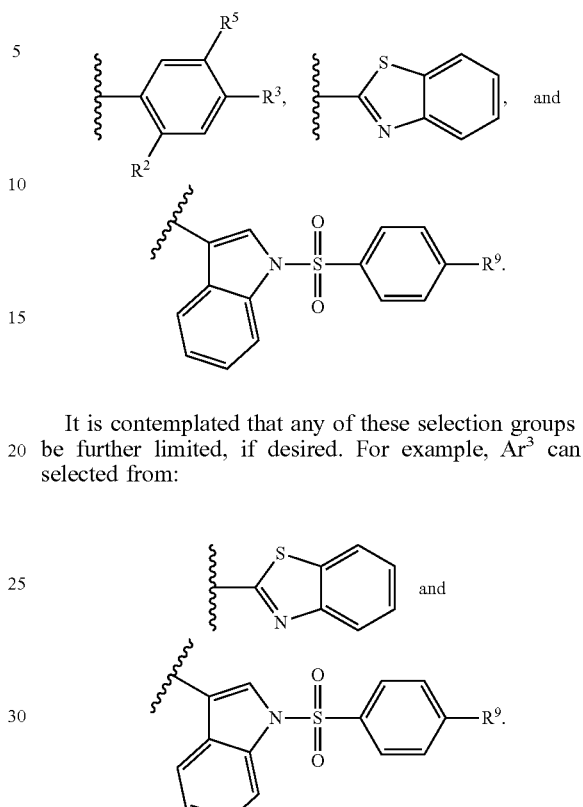

It is contemplated that any of these selection groups can be further limited, if desired. For example, $Ar^3$ can be selected from:

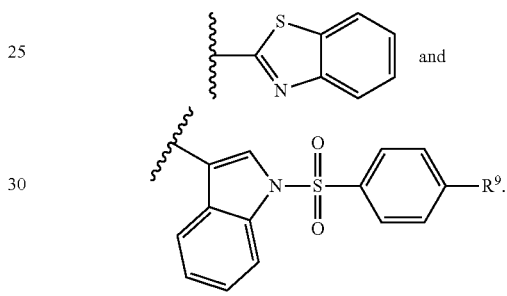

As a further example, $Ar^3$ can be:

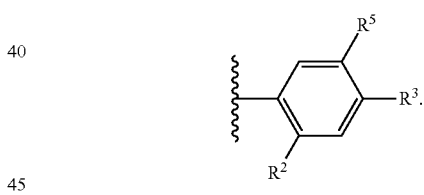

3. R1 Groups
In one aspect, $R^1$ is selected from hydrogen and $C_1$-$C_4$ alkyl. For example, $R^1$ can be hydrogen. As a further example, $R^1$ can be methyl, ethyl, propyl, or butyl.
In further aspects, $R^1$ is substituted with 0-2 groups (e.g., 0, 1, or 2 groups) selected from halogen, alkoxy, carboxymethyl, carboxyethyl, trifluoromethyl, trifluoromethoxy, and —$SO_2$Me.

4. R2 Groups
In one aspect, $R^2$ is selected from hydrogen, halogen, methyl, ethyl, n-propyl, i-propyl, n-butyl, i-butyl, t-butyl, trifluoromethyl, trifluoroethyl, methoxy, ethoxy, n-propoxyl, i-propoxyl, n-butoxyl, i-butoxyl, and t-butoxyl.

5. R3 Groups
In one aspect, $R^3$ is selected from hydrogen, halogen, methyl, ethyl, n-propyl, i-propyl, n-butyl, i-butyl, t-butyl, trifluoromethyl, trifluoroethyl, methoxy, ethoxy, n-propoxyl, i-propoxyl, n-butoxyl, i-butoxyl, and t-butoxyl.

6. R4 Groups
In one aspect, each of $R^4$ is independently selected from hydrogen, halogen, alkyl, trifluoromethyl, trifluoromethoxy, alkoxy, and —$SO_2$Me.

7. R5 Groups

In one aspect, $R^5$ is selected from hydrogen, halogen, methyl, ethyl, n-propyl, i-propyl, n-butyl, i-butyl, t-butyl, trifluoromethyl, trifluoroethyl, methoxy, ethoxy, n-propoxyl, i-propoxyl, n-butoxyl, i-butoxyl, and t-butoxyl.

8. R6 Groups

In one aspect, each of $R^6$ is $R^{6a}$ and $R^{6b}$ is independently selected from hydrogen and $C_1$-$C_4$ alkyl. For example, methyl, ethyl, n-propyl, i-propyl, n-butyl, i-butyl, and t-butyl. In a further aspect, $R^{6a}$ and $R^{6b}$ together comprise =O.

9. R7 Groups

In one aspect, $R^7$ is selected from hydrogen, methyl, and ethyl. For example, $R^7$ can be hydrogen. As a further example, $R^1$ is methyl or ethyl. As a yet further example, $R^7$ is methyl.

10. R8 Groups

In one aspect, $R^8$ is selected from hydrogen, methyl, and ethyl. For example, $R^8$ can be hydrogen. As a further example, $R^8$ is methyl or ethyl. As a yet further example, $R^8$ is methyl.

11. R9 Groups

In one aspect, $R^9$ is selected from hydrogen, halogen, methyl, ethyl, methoxy, ethoxy, carboxymethyl, and carboxyethyl. For example, $R^9$ can be hydrogen. As a further example, $R^9$ is halogen, methyl, ethyl, methoxy, ethoxy, carboxymethyl, or carboxyethyl.

12. R10 Groups

In one aspect, $R^{10}$ is selected from $C_1$-$C_4$ alkyl and $Ar^3$. In a further aspect, $R^{10}$ can be $C_1$-$C_4$ alkyl, for example, methyl, ethyl, n-propyl, i-propyl, n-butyl, i-butyl, s-butyl, or t-butyl. In a further aspect, $R^{10}$ can be $Ar^3$, wherein $Ar^3$ is selected from:

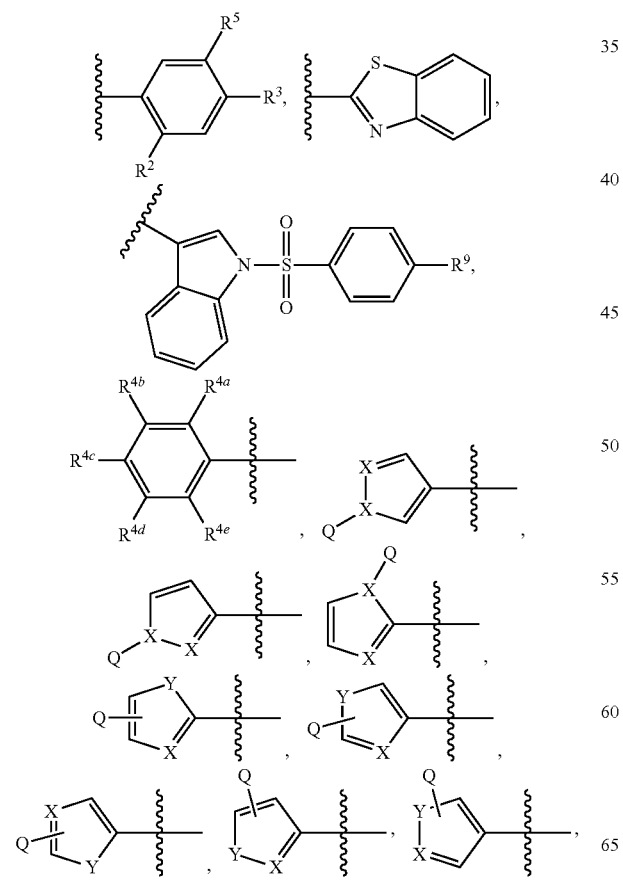

In a further aspect, $R^{10}$ is $Ar^3$ selected from:

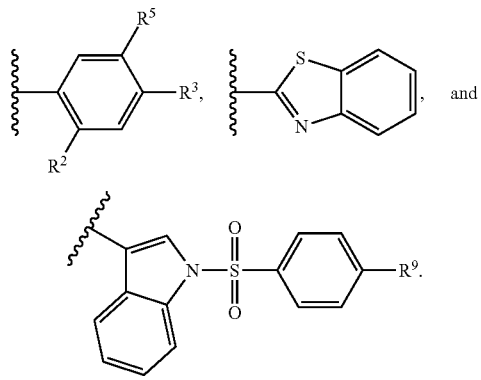

In a further aspect, $R^{10}$ is:

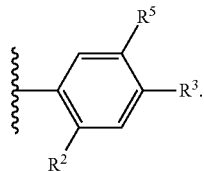

In a further aspect, $R^{10}$ is $C_1$-$C_4$ alkyl.

B. Methods of Making the Compounds

The compounds can be prepared according to the following scheme.

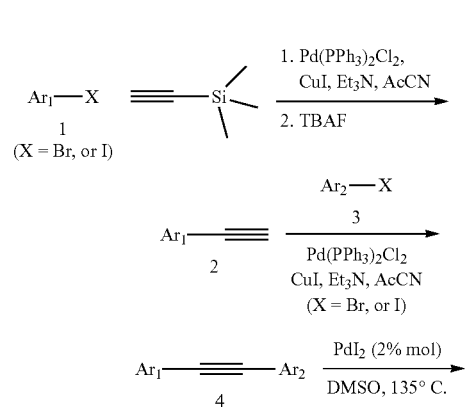

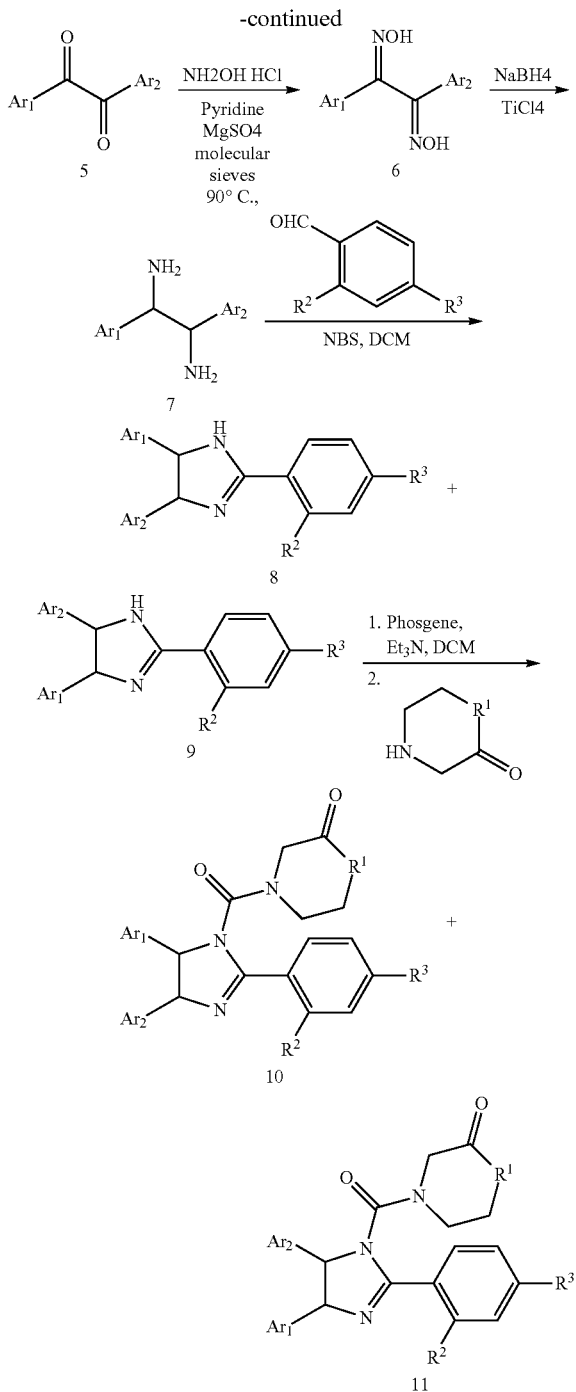

amount), triethylamine (excess), and then aryl halide 3 (slight excess) are added to a solution of arylacetylene 2 in a suitable solvent, such as acetonitrile. The reaction is preferably carried out under an inert atmosphere, with stirring at a temperature of about 60° C. until the reaction is complete. The product 4 is then isolated and purified.

Diarylacetylene 4 and $PdI_2$ (catalytic amount) in a solvent such as DMSO are stirred at 135° C. to yield diketone 5. After cooling to room temperature, pyridine, molecular sieves, anhydrous magnesium sulfate, and hydroxylamine hydrochloride added. After stirring at 90° C., another portion of hydroxylamine hydrochloride is added to the reaction mixture. The resulting mixture is stirred at 90° C. Dioxime 6 is then isolated and purified.

$NaBH_4$ is added portion-wise to a solution of dioxime 6 in a suitable solvent, such as dimethoxyethane. The reaction mixture is cooled in an ice water bath for 10 mins, and then $TiCl_a$ (excess) is added dropwise, and the reaction mixture is stirred at 90° C. Diamine 7 is then isolated and can be used in the next step without further purification.

the corresponding benzaldehyde and N-bromosuccinimide are added to a solution of diamine 7 in a suitable solvent, such as dichloromethane. The mixture is stirred at room temperature until the reaction is complete. The crude product is isolated and purified to give a mixture of two regioisomers of dihydro imidazole 8 and 9.

Triethylamine and phosgene are added dropwise at 0° C. to the mixture of dihydro-imidazole 8 and 9 under a stream of inert gas. The resulting mixture is stirred at 0° C. for 30 mins, and then at room temperature for 30 mins. The reaction is concentrated and placed under high vacuum. The remaining residue is re-dissolved. Triethylamine is added to this solution, and then pierazin-2-one at 0° C. The reaction is quenched by adding water. Regioisomers 10 and 11 are then isolated and purified. Isomers 10 and 11 are separated by supercritical fluid chromatography (OD-H column).

The compounds are active against MDM2 and/or MDMX, and generally have $EC_{50}$ values against hMDM2 and/or hMDMX ranging from 10 to 50 micromolar. $EC_{50}$ refers to the concentration of the compound that is required for 50% antagonism or inhibition of hMDM2 or hMDMX. $EC_{50}$ also refers to the concentration of a substance that is required for 50% antagonism or inhibition of MDM2 or MDMX in vivo. The activity of the compounds, including $EC_{50}$, is determined according to the procedures discussed below in the Examples section. The compounds can have equipotent activity against MDM2 or MDMX, or can be selective against MDMX over MDM2.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of com- Triethylamine (excess), and then trimethylsilylacetylene (e.g. 1.1 equivalents) are added to a solution of aryl halide 1, $Pd(PPh_3)_2Cl_2$ (catalytic amount), and CuI (catalytic amount) in a suitable solvent, such as acetonitrile. The reaction is preferably carried out under an inert atmosphere, with stirring at a temperature of about 60° C. until the reaction is complete. The reaction mixture is then cooled to room temperature, followed by the addition tetra-n-butylammonium fluoride (1 equivalent), followed by stirring at room temperature. The product 2 is then isolated and purified.

Diarylacetylene 4 is prepared by coupling 2 with aryl halide 3. $(PPh_3)_2Cl_2$ (catalytic amount), CuI (catalytic pounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The compounds and pharmaceutical compositions of the invention are useful in treating or controlling cell proliferative disorders, in particular oncological disorders, such as cancer. The compounds and pharmaceutical compositions containing the compounds can be useful in the treatment or control of solid tumors, such as breast, colon, lung and prostate tumors, by action of restoring p53 activity through the inhibition of MDM2 and/or MDMX.

Examples of cell proliferative disorders for which the compounds and compositions can be useful in treating, include, but not limited to, Leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, curvical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. For a review of such disorders, see Fishman et al., 1985, Medicine, 2d Ed., J.B. Lippincott Co., Philadelphia).

To treat or control the cell proliferative disorder, the compounds and pharmaceutical compositions comprising the compounds are administered to a subject in need thereof, such as a vertebrate, e.g., a mammal, a fish, a bird, a reptile, or an amphibian. The subject of can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cell proliferative disorder, such as cancer.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition, such as cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. administration. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In one aspect, the invention relates to methods of making compounds useful as aryl-substituted imidazoles, which can be useful in the treatment of diseases of uncontrolled cellular proliferation.

The compounds of this invention can be prepared by employing reactions as shown in the disclosed schemes, in addition to other standard manipulations that are known in the literature, exemplified in the experimental sections or clear to one skilled in the art. Substituent numbering as shown in schemes does not necessarily correlate to that used in the claims and often, for clarity, a single substituent is shown to attach to the compound where multiple substituents are allowed under the definitions disclosed herein.

Reactions used to generate the compounds of this invention are prepared by employing reactions as shown in the disclosed Reaction Schemes, in addition to other standard manipulations known in the literature or to one skilled in the art. The following examples are provided so that the invention might be more fully understood, are illustrative only, and should not be construed as limiting.

In one aspect, the invention relates to a method for the manufacture of a medicament for treating a disease of uncontrolled cellular proliferation in a mammal comprising combining a therapeutically effective amount of a disclosed compound or product of a disclosed method with a pharmaceutically acceptable carrier or diluent.

In one aspect, the invention relates to the use of a disclosed compound or a product of a disclosed method. In a further aspect, a use relates to the manufacture of a medicament for the treatment of a disease of uncontrolled cellular proliferation in a mammal. In a further aspect, a use relates to treatment of a disease of uncontrolled cellular proliferation in a mammal.

In one aspect, the invention relates to a kit comprising a disclosed compound or a product of a disclosed method and one or more of at least one agent known to increase cellular proliferation or risk of cellular proliferation; at least one agent known to decrease cellular proliferation or risk of cellular proliferation; at least one agent known to treat a disease of uncontrolled cellular proliferation; or instructions for treating a disease of uncontrolled cellular proliferation.

In a further aspect, the at least one compound or the at least one product and the at least one agent are co-formulated. In a further aspect, the at least one compound or the at least one product and the at least one agent are co-packaged.

EXAMPLES

A. Experimental Protocols

13. Plasmid Constructs and Protein Production

The p53-binding domain of mouse and human MDMX (amino acids 1-185) and humanMDM2(amino acids 1-188) were amplified by PCR and cloned into the pGEX-4T1 plasmid. Recombinant GST fusion proteins were prepared in BL21 (DE3) *Escherichia coli* cells. The lysates were cleared by spinning at 100,000×g, and the supernatant was loaded onto a 5-ml GSTrap Fast-Flow column (GE Healthcare). The proteins were further purified via a Mono Q column and an S200 gel filtration column. Peak fractions were combined and dialyzed against phosphate-buffered saline (pH 7.6) containing 2 mM phenylmethylsulfonyl fluoride.

14. Fluorescence Polarization Assays

Fluorescence polarization (FP) assay was conducted in assay buffer containing 10 mM Tris (pH 8.0), 42.5 mM NaCl, and 0.0125% Tween 20. The wild type p53 peptide (amino acids 15-29) was GSGSSQETFSDLWKLLPEN, and the mutant AAA-p53 peptide was GSGSSQETFADLAKLAPEN. The FP assay was carried out 15 nM Texas Red and 1 uM GST-MDMX or GST-MDM2. For MDM2-p53 or MDMX-p53 inhibitor assay, small molecules were preincubated with the recombinant protein for 30 min. The labeled peptide was then added and incubated for 45 min. FP assay was conducted in 384-well black microplates (Corning Glass). The FP assay with Texas Red-labeled p53 peptide was analyzed using an EnVision multilabel plate reader with a 555-nm excitation filter, a 632-nm static and polarized filter, and a Texas Red FP dichroic mirror. The unlabeled competitor peptide and nutlin-3 were used as positive controls, and the alanine-substituted p53 peptide (AAA-p53) was used as a negative control.

15. NMR Chemical Shift Perturbation Experiment

All the HSQC spectra were recorded at 298 K using Bruker Avance 600 or 800 MHz NMR spectrometers, equipped with $^1H/^{13}C$ detect, TCI triple resonance cryogenic probes. The NMR samples contained 0.1 mM $^{15}N$-labeled MDM4 in complex with the small molecule, in molar ratio of 1:1, in 10 mM NaPi, 200 mM NaCl, 2 mM DTT, 0.01% NaN3, 90% $H_2O$/10% $D_2O$ at pH 6.5. The backbone chemical shift assignments of the free protein and in complex with SJ558295 were obtained using either free $^{13}C$, $^{15}N$-labeled MDM4 or in complex with equimolar SJ558295 in the presence of 5% deuterated DMSO. The backbone chemical shift assignments were obtained using a standard triple-resonance assignment strategy through the analysis of two-dimensional [$^1H$, $^{15}N$] HSQC and the three-dimensional HNCA, FIN(CO)CA, HNCACB and $^{15}N$ resolved NOESY spectra of free MDM4. MDM4 in complex with either the p53 peptide or SJ558295 were assigned with the help of three-dimensional I-INCA, HN(CO)CA and $^{15}N$ resolved NOESY spectra of the complex. All the spectra were processed using TOPSPIN NMR software and analyzed using the program, computer aided resonance assignment, CARA. Several backbone amides were not observed in the HSQC spectrum of free MDM4 and were observed in the spectra of the complex.

16. Experimental Protocols for In Vitro PK Study a. Solubility.

Solubility assay was carried out on Biomek FX lab automation workstation (Beckman Coulter, Inc., Fullerton, Calif.) using μSOL Evolution software (pION Inc., Woburn, Mass.). The detailed method is described as following. 10 μL of 10 mM compound stock (in DMSO) was added to 190 μL 1-propanol to make a reference stock plate. 5 μL from this reference stock plate was mixed with 70 μl, 1-propanol and 75 μL citrate phosphate buffered saline (isotonic) to make the reference plate, and the UV spectrum (250 nm-500 nm) of the reference plate was read. 6 μL of 10 mM test compound stock was added to 594 μL buffer in a 96-well storage plate and mixed. The storage plate was sealed and incubated at room temperature for 18 hours. The suspension was then filtered through a 96-well filter plate (pION Inc., Woburn, Mass.). 75 μL filtrate was mixed with 75 μL 1-propanol to make the sample plate, and the UV spectrum of the sample plate was read. Calculation was carried out by μSOL Evolution software based on the AUC (area under curve) of UV spectrum of the sample plate and the reference plate. All compounds were tested in triplicates.

b. Permeability.

Parallel Artificial membrane Permeability Assay (PAMPA) was conducted by Biomek FX lab automation workstation (Beckman Coulter, Inc., Fullerton, Calif.) and PAMPA evolution 96 command software (pION Inc., Woburn, Mass.). The detailed method is described as following. 3 μL of 10 μM test compound stock in DMSO was mixed with 597 μL of citrate phosphate buffered saline (isotonic) to make diluted test compound. 150 μL of diluted test compound was transferred to a UV plate (pION Inc., Woburn, Mass.) and the UV spectrum was read as the reference plate. The membrane on pre-loaded PAMPA sandwich (pION Inc., Woburn, Mass.) was painted with 4 μL GIT lipid (pION Inc., Woburn, Mass.). The acceptor chamber was then filled with 200 μL ASB (acceptor solution buffer, pION Inc., Woburn, Mass.), and the donor chamber was filled with 180 μL diluted test compound. The PAMPA sandwich was assembled, placed on the Gut-box and stirred for 30 minutes. Aqueous Boundary Layer was set to 40 μm for stirring. The UV spectrum (250-500 nm) of the donor and the acceptor were read. The permeability coefficient was calculated using PAMPA evolution 96 command software (pION Inc., Woburn, Mass.) based on the AUC of the reference plate, the donor plate and the acceptor plate. All compounds were tested in triplicates.

c. Plasma Stability.

Compound stocks were 10 mM in DMSO. The internal standard was 10 μM warfarin in methanol. 1.9 ml mouse plasma (Fisher Scientific, catalog #: NC9050370) or pooled human plasma (Innovative Research Inc., catalog # IPLA-1)

was added to the columns of 1, 4, 7 and 10 of a 2 ml 96-well deep well plate (pION Inc., MA, #110023); this was the master plate. 1.9 µl compound stock was added to each well with plasmas and mixed well. Using a multi-channel pipette, 600 µl from the columns of 1, 4, 7 and 10 were taken and added into the rest of the columns (fluids in column 1 added to columns 2 and 3, column 4 into 5 and 6, and so on). From the master plate, 65 µl were taken from each well and added into 8 storage plates (pION Inc., MA, #110323), each for a time point. The storage plates was then incubated at 37° C. and shaken at 60 rpm. Samples were taken at 0 min, 30 min, 1 hr, 2 hr, 4 hr, 8 hr, 24 hr and 48 hr. At each time point, 195 µl internal standard was added to quench the reaction. The plates were then centrifuged at 4000 rpm for 15 min and supernatant was analyzed by UPLC-MS. The compound was detected by SIR and quantitation was based on peak area ratio of test compound vs. the internal standard.

d. Simulated Gastric Fluid (SGF) Stability.

Compound stocks were 10 mM in DMSO. The internal standard was 10 µM warfarin in methanol. 1.4 ml concentrate HCl (37%), 0.4 g NaCl and 0.64 g pepsin were added to 198 ml DI water to make SGF (pH 1). 1.9 ml SGF was added to the columns of 1, 4, 7 and 10 of a 2 ml 96-well deep well plate (pION Inc., MA, #110023); this was the master plate. 1.9 µl compound stock was added to each well with SGF and mixed well. Using a multi-channel pipette, 600 µl from the columns of 1, 4, 7 and 10 were taken and added into the rest of the columns (fluids in column 1 added to columns 2 and 3, column 4 into 5 and 6, and so on). From the master plate, 65 µl were taken from each well and added into 8 storage plates (pION Inc., MA, #110323), each for a time point. The storage plates was then incubated at 37° C. and shaken at 60 rpm. Samples were taken at 0 min, 30 min, 1 hr, 2 hr, 4 hr, 8 hr, 24 hr and 48 hr. At each time point, 195 µl internal standard was added to quench the reaction. The plates were then centrifuged at 4000 rpm for 15 min and supernatant was analyzed by UPLC-MS. The compound was detected by SIR and quantitation was based on peak area ratio of test compound vs. the internal standard.

e. PBS Stability.

Compound stocks were 10 mM in DMSO. The internal standard was 10 µM warfarin in methanol. 1.9 ml PBS (Mediatech Inc., Manassas, Va., catalog #21-040-CM) was added to the columns of 1, 4, 7 and 10 of a 2 ml 96-well deep well plate (pION Inc., MA, #110023); this was the master plate. 1.9 µl compound stock was added to each well with SGF and mixed well. Using a multi-channel pipette, 600 µl from the columns of 1, 4, 7 and 10 were taken and added into the rest of the columns (fluids in column 1 added to columns 2 and 3, column 4 into 5 and 6, and so on). From the master plate, 65 pil were taken from each well and added into 8 storage plates (pION Inc., MA, #110323), each for a time point. The storage plates was then incubated at 37° C. and shaken at 60 rpm. Samples were taken at 0 min, 30 min, 1 hr, 2 hr, 4 hr, 8 hr, 24 hr and 48 hr. At each time point, 195 µl internal standard was added to quench the reaction. The plates were then centrifuged at 4000 rpm for 15 min and supernatant was analyzed by UPLC-MS. The compound was detected by SIR and quantitation was based on peak area ratio of test compound vs. the internal standard.

f. Liver Microsomal Stability.

1.582 mL of mouse liver microsome (20 mg/mL, female CD-1 mice, pooled, Fisher Scientific, # NC9567486) was mixed with 0.127 ml of 0.5M EDTA solution and 48.3 ml potassium phosphate buffer (0.1M, pH 7.4, 37° C.) to make 50 ml of mouse liver microsome solution. Human liver microsomal solution was made with human liver microsome (50 pooled mix gender, Fisher Scientific #50-722-516) the same way. 1 volume of 10 mM DMSO compound stock was mixed with 4 volume of acetonitrile to make 2 mM diluted compound stock in DMSO and acetonitrile. 37.83 µL, diluted compound stock was added to 3 mL liver microsomal solution and vortexed to make microsomal solution with compound. 1 ml of liver microsomal solution with compound is added to each well of a master storage plate (pION Inc., MA, #110323). All compounds are in triplicates. Mouse and human liver microsomes were tested side by side on the same plate. 175 µL of each well was dispensed from the master plate into 5 storage plates. For 0 hour time point, 450 pit pre-cooled (4° C.) internal standard (10 µM warfarin in methanol) was added to the first plate before the reaction starts. 5.25 ml of microsome assay solution A (Fisher Scientific, # NC9255727) was combined with 1.05 ml of solution B (Fisher Scientific, # NC9016235) in 14.7 ml of potassium phosphate buffer (0.1 M, pH 7.4). 45 µL of this A+B solution was added to each well of all the 96-well storage plates and mixed with pipette briefly. The plates are sealed, and all plates except 0-hr plate were incubated at 37° C., shaken at a speed of 60 rpm. 0.5 hr, 1 hr, 2 hr and 4 hr time points were taken. At each time point, 450 µL pre-cooled internal standard was added to the plate to quench the reaction. The quenched plate was then centrifuged (model 5810R, Eppendorf, Westbury, N.Y.) at 4000 rpm for 15 minutes. 150 µL supernatant was transferred to a 96-well plate and analyzed by UPLC-MS (Waters Inc., Milford, Mass.). The compounds and internal standard were detected by SIR. The log peak area ratio (compound peak area/internal standard peak area) was plotted vs time (hr) and the slope was determined to calculate the elimination rate constant $[k=(-2.303)*slope]$. The half life (hr) was calculated as $t(1/2)=0.693/k$. Intrinsic clearance was calculated as $CL_{int}'=(0.693/(t1/2))*(1/\text{microsomal concentration in the reaction solution})*(45 \text{ mg microsome/gram liver})*(\text{gram liver/kg b.w.})$, where microsomal concentration in the reaction solution is 0.5 mg/ml, and gram liver/kg b.w. of CD-1 female mice and human are 52 and 20, respectively.

17. General Synthesis of Compounds

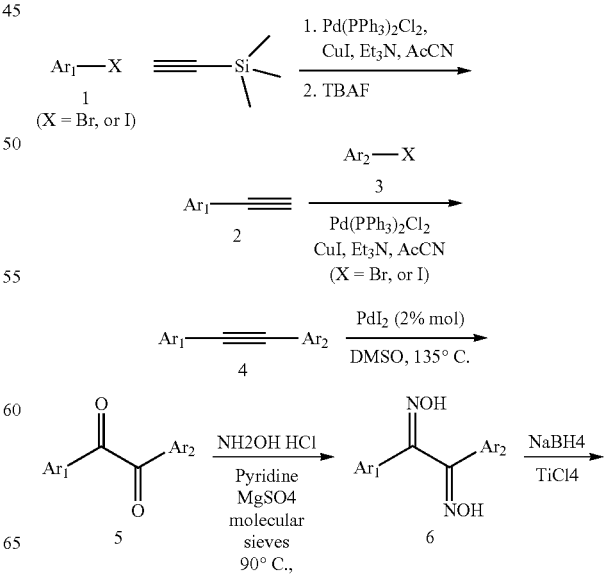

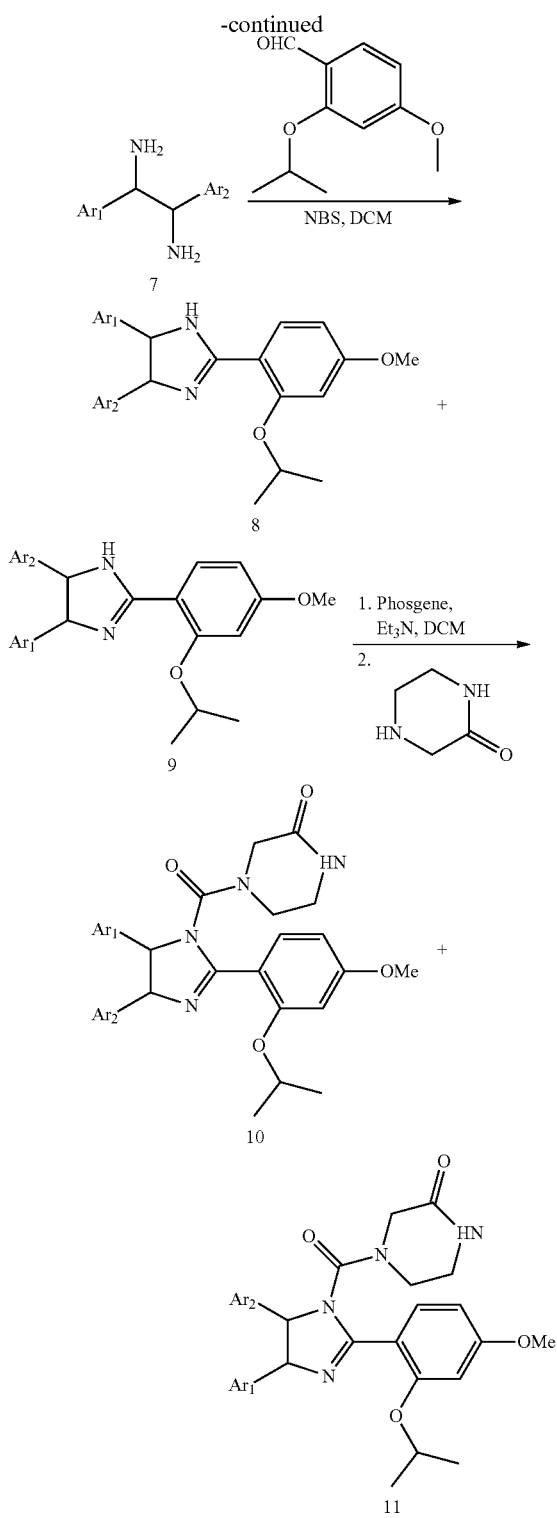

The mixture continued to stir at room temperature for 2 hours. And then, 50 mL of saturated sodium chloride solution was added to the reaction mixture. The two layers were separated. The aqueous layer was extracted by diethyl ether (50 mL×3). The organic layers were combined, dried over sodium sulfate, and concentrated under vacuum. Purification of the crude residue was performed by flash column chromatography (Biotage SP1, silica column, eluting with a gradient of 1-10% ethyl acetate in hexane) to give arylacetylene 2.

Diarylacetylene 4 was prepared by coupling of 2 and aryl halide 3. To the solution of arylacetlene 2 (1 mmol, 1 equiv.) in 10 mL acetonitrile was added $(PPh_3)_2Cl_2$ (0.02 mol, 0.02 equiv.), CuI (0.03 mmol, 0.03 equiv.), triethylamine (3 mmol, 3 equiv.), and then aryl halide 3 (1.1 mmol, 1.1 equiv.). The mixture was degassed three times, and then stirred at 60° C. under nitrogen for 16 hours. After cooled to room temperature, the precipitate was filtered off. The filtrate was concentrated. The residue was then purified by flash chromatography (Biotage SP1, silica column, eluting with ethyl acetate/hexane) to give diarylacetylene 4.

Diarylacetylene 4 (0.66 mmol, 1 equiv.) and $PdI_2$ (0.013 mmol, 0.02 equiv.) in 4 mL anhydrous DMSO were stirred at 135° C. for 16 hours to yield diketone 5. After cooled to room temperature, to the reaction mixture was added 4.5 mL anhydrous pyridine, 2 g of 4 Å molecular sieves, 1.5 g of anhydrous magnesium sulfate, and hydroxylamine hydrochloride (4 mmol, 6 equiv.). After stirred at 90° C. for 16 hours, another portion of hydroxylamine hydrochloride (4 mmol, 6 equiv) was added into the reaction mixture. The mixture continued to stir at 90° C. for 16 h. The reaction mixture was cooled to room temperature, and filtered off solid. The filtrate was concentrated. The remaining residue was then purified by flash chromatography (Biotage SP1, silica column, eluting with ethyl acetate/hexane) to give dioxime 6.

To the solution of dioxime 6 (0.3 mmol, 1 equiv.) in 6 mL dimethoxyethane was added NaBH4 (2.4 mmol, 8 equiv.) portion-wise. The reaction mixture was cooled in ice water bath for 10 mins, and then was added $TiCl_4$ (1.5 mmol, 5 equiv.) dropwise. The reaction mixture turned to dark green. After stirred at room temperature for 16 hours, the reaction mixture was blue suspension. It continued to stir at 90° C. for 2 hours. After cooled to room temperature, the reaction was quenched by adding 1 N NaOH until pH reached to 8. The mixture turned to a white suspension. Product was extracted by dichloromethane 20 mL×3. Organic layers were combined, dried over sodium sulfate, and concentrated to give diamine 7. The crude product 7 was used for the next step without further purification.

To the solution of diamine 7 (0.3 mmol, 1 equiv.) in 5 mL dicloromethane was added 2-isopropoxy-4-methoxybenzaldehyde (0.27 mmol, 0.9 equiv.) and N-bromosuccinimide (0.18 mmol, 0.6 equiv.). The mixture was stirred at room temperature for 2 hours. The solvent was evaporated, and the remaining crude product was purified by flash chromatography ((Biotage SP1, silica column, eluting with a gradient of 1-10% methanol in dichloromethane) to give the mixture of two regioisomers of dihydro imidazole 8 and 9.

To the mixture of dihydro-imidazole 8 and 9 (0.18 mmol, 1 equiv.) in 2 mL dichloromethane and triethylamine (0.72 mmol, 4 equiv.) was added phosgene (0.44 mmol, 2.5 equiv.) dropwise at 0° C. under a stream of nitrogen. The resulting mixture was stirred at 0° C. for 30 mins, and then at room temperature for 30 mins. The reaction was concentrated down and placed under high vacuum for 1 hour. The remaining residue was re-dissolved in 2 mL dicholormeth- To the solution of aryl halide 1 (30 mmol, 1 equiv.) in 50 mL acetonitrile was added $Pd(PPh_3)_2Cl_2$ (0.6 mmol, 0.02 equiv.), CuI (0.9 mmol, 0.03 equiv.), triethylamine (90 mmol, 3 equiv.), and then trimethylsilylacetylene (33 mmol, 1.1 equiv.). The mixture was degassed three times. After stirring at 60° C. under nitrogen for 16 h, the reaction mixture was cooled to room temperature, followed by adding tetra-n-butylammonium fluoride (30 mmol, 1 equiv.).

ane. To the solution was added triethylamine (0.36 mmol, 2 equiv.), and then pierazin-2-one in 1 mL of dichloromethane at 0° C. The mixture was allowed to stir at room temperature for 2 hours. The reaction was quenched by adding 1 mL water. The aqueous layer was extracted by dichloromethane 2 mL x 3. The organic layers were combined, dried over sodium sulfate, and concentrated to give the crude product. Purification was performed on Waters reverse phase HPLC (C18 column, mobile phase: water with 0.1% formic acid, and methanol with 0.1% formic acid) to yield the mixture of two regioisomers 10 and 11. Two regioisomers and two enantiomers were separated by SFC (OD-H column).

a. 4-((4S,5R)-4-(4-chlorophenyl)-2-(2-isopropoxy-4-methoxyphenyl)-5-(m-tolyl)-4,5-dihydro-1H-imidazole-1-carbonyl)piperazin-2-one

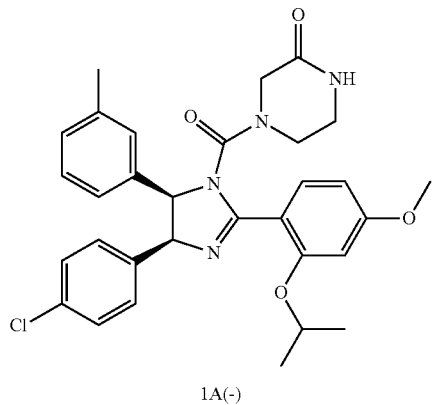 [SMILES: COc1ccc(C2=N[C@@H](c3ccc(Cl)cc3)[C@@H](c3cccc(C)c3)N2C(=O)N2CCNC(=O)C2)c(OC(C)C)c1]

1A(-)

b. 4-((4R,5S)-4-(4-chlorophenyl)-2-(2-isopropoxy-4-methoxyphenyl)-5-(m-tolyl)-4,5-dihydro-1H-imidazole-1-carbonyl)piperazin-2-one

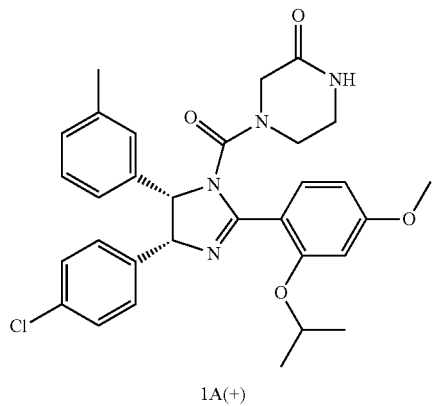 [SMILES: COc1ccc(C2=N[C@H](c3ccc(Cl)cc3)[C@H](c3cccc(C)c3)N2C(=O)N2CCNC(=O)C2)c(OC(C)C)c1]

1A(+)

c. 4-((4S,5R)-5-(4-chlorophenyl)-2-(2-isopropoxy-4-methoxyphenyl)-4-(m-tolyl)-4,5-dihydro-1H-imidazole-1-carbonyl)piperazin-2-one

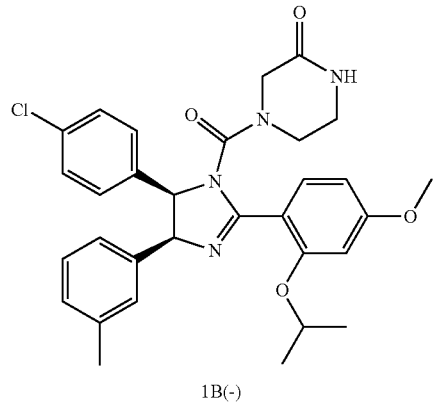 [SMILES: COc1ccc(C2=N[C@@H](c3cccc(C)c3)[C@@H](c3ccc(Cl)cc3)N2C(=O)N2CCNC(=O)C2)c(OC(C)C)c1]

1B(-)

d. 4-((4R,5S)-5-(4-chlorophenyl)-2-(2-isopropoxy-4-methoxyphenyl)-4-(m-tolyl)-4,5-dihydro-1H-imidazole-1-carbonyl)piperazin-2-one

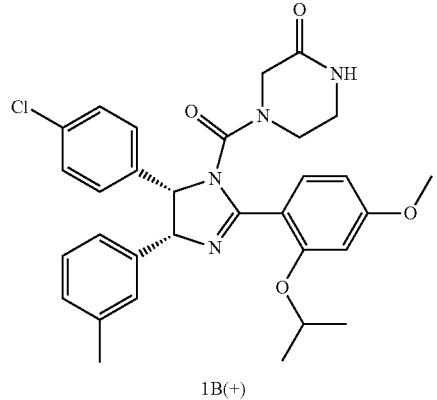 [SMILES: COc1ccc(C2=N[C@H](c3cccc(C)c3)[C@H](c3ccc(Cl)cc3)N2C(=O)N2CCNC(=O)C2)c(OC(C)C)c1]

1B(+)

18. Experimental Protocols for the Synthesis of Analogs a. Procedure to Synthesize 2-isopropoxy-4-methoxybenzaldehyde 11

To the solution of 2-hydroxy-4-methoxybenzaldehyde 10 (6.6 mmol, 1 equiv.) and 2-iodopropane (7.23 mmol, 1.1 equiv.) in 7 mL of DMF was added $K_2CO_3$ (26.3 mmol, 4 equiv.). The reaction was stirred at 45° C. for 18h. Next day, added DCM 5 mL, filtered off solid, and washed solid with DCM twice. The filtrate was washed by water. And then organic layer was dried over $MgSO_4$, and concentrated. The remaining residues was purified by Biotage SP1:0-20% EtOAc in hexane over 7 CV, 20% EtOAc in hexane over 5 CV.

b. General Procedure to Synthesize 1-((4-substituted phenyl)sulfonyl)-1H-indole-3-carbaldehyde 14

To the solution of 1H-indole-3-carbaldehyde 12 (0.69 mmol, 1 equiv.) in 3 mL DMF was added $K_2CO_3$ (2.07 mmol, 3 equiv.) The mixture was stirred at the room temperature overnight (around 16 hours). And then sulfonyl chloride 13 (1.033 mmol, 1.5 equiv.) was added into the reaction mixture. The reaction was allowed to stirred at the room temperature or 60° C. for 1 h. After cooled to the room temperature, added EtOAc 5 mL, and washed with sat'd NaCl.

The organic layer was dried over $MgSO_4$, and concentrated. The remaining residues was purified by Biotage SP1: 0-30% EtOAc in hexane over 7 CV, 30% EtOAc in hexane over 10 CV.

c. General Procedure to Synthesize Diarylacetylene 3

To the solution of aryl acetylene 1 (30 mmol, 1 equiv.) and aryl halide 2 (30 mmol, 1 equiv.) in 50 mL acetonitrile was added $Pd(PPh_3)_2Cl_2$ (0.6 mmol, 0.02 equiv.), CuI (0.9 mmol, 0.03 equiv.), triethylamine (90 mmol, 3 equiv.). The mixture was degassed three times. When aryl iodide was applied as a starting material, the reaction mixture was stirred at the room temperature for 16h. Otherwise, aryl bromide was used as a starting material followed by stirring at 60° C. for 16 hours. After cooled to room temperature, the precipitate was filtered off. The filtrate was concentrated. The residue was then purified by flash chromatography (Biotage SP1, silica column, eluting with ethyl acetate/hexane) to give diarylacetylene 3.

d. General Procedure to Synthesize 1,2-diaryl-1,2-diamino Ethane 6

Diarylacetylene 3 (12.8 mmol, 1 equiv.) was dissolved in 60 mL of acetone. The solution of 3 was then transferred into the aqueous solution of $KMnO_4$ (26.9 mmol, 2.1 equiv.), $NaHCO_3$ (7.68 mmol, 0.6 equiv.) and $MgSO_4$ (25.6 mmol, 2.0 equiv.) in 40 mL $H_2O$. After stirring at 40° C. for 30-60 min, the reaction mixture was quenched by adding saturated $Na_2S_2O_3$ aqueous solution. The desired diketone was extracted by EtOAc (60 mL×3). The organic layers were combined, dried over $MgSO_4$, and concentrated under vacuum. The crude product 4 was used for the next step without further purification.

The suspension of diketone 4 (10.2 mmol, 1 equiv.) and $NH_2OH.HCl$ (61 mmol, 6 equiv.) in 30 mL of anhydrous EtOH and 7 mL of anhydrous pyridine (87 mmol, 8.5 equiv.) was refluxed at 90° C. for 1-3 days. The reaction was monitored by LCMS until over 90% of diketone was converted to the corresponding dioxime 5. The reaction mixture was cooled to room temperature followed by adding 10 mL of 2 N HCl. The product was extracted by EtOAc (60 mL×3). The organic layers were combined, dried over $MgSO_4$, and concentrated under vacuum. The remaining residue was then purified by flash chromatography (Biotage SP1, silica column, eluting with ethyl acetate/hexane) to give dioxime 5.

To the solution of dioxime 5 (8.6 mmol, 1 equiv.) in 35 mL dimethoxyethane was added NaBH4 (35 mmol, 4 equiv.) portion-wise. The reaction mixture was cooled in ice water bath for 10 mins, and then was added $TiCl_a$ (19 mmol, 2.2 equiv.) dropwise. After stirred at 0° C. for 30 min and room temperature for 1 hour, the reaction mixture continued to stir at 90° C. for 6 hours. After cooled to room temperature, the reaction was quenched by adding 10 mL of 2 N HCl and 20 mL $H_2O$ at 0° C. The mixture was stirred at the room temperature until there were no bubbles. The aqueous layer was in purple. Separated aqueous layer, which was then neutralized by adding 2N NaOH until pH reached 8.0. The mixture was stirred overnight, and turned to a white suspension. Product was extracted by EtOAc 60 mL x 3. Organic layers were combined, dried over $MgSO_4$, and concentrated to give diamine 6. The crude product 6 was used for the next step without further purification.

e. General Procedure to Synthesize nutlin-3a analogues, 4-[4,5-diaryl-2-(2-isopropoxy-4-methoxyphenyl)-4,5-dihydro-1H-imidazole-1-carbonyl]-piperazin-2-one To the solution of diamine 6 (0.15 mmol, 1 equiv.) in 3 mL dicloromethane was added aldehyde 7 (0.15 mmol, 1 equiv., aldehyde 11 and 14 was applied here respectively) and N-bromosuccinimide (0.15 mmol, 1 equiv.). The mixture was stirred at room temperature for 2 hours. The solvent was evaporated, and the remaining crude product was purified by flash chromatography ((Biotage SP1, silica column, eluting with a gradient: dichloromethane over 3 CV, and 0-10% methanol in dichloromethane over 10 CV, 10% methanol in dichloromethane over 5 CV) to give the mixture of two regioisomers of dihydro imidazole 8.

To the mixture of dihydro-imidazole 8 (0.9 mmol, 1 equiv.) and triphosgen (0.118, 1.3 equiv.) in 2 mL dichloromethane was added triethylamine (0.455 mmol, 5 equiv.) at 0° C. The mixture was stirred at 0° C. for 15 min and then at the room temperature for 1 hour, followed by adding solid piperzin-2-one (0.18 mmol, 2 equiv). The mixture was allowed to stir at room temperature for 2-16 hours. The reaction was monitored by LCMS until the competed conversion. The reaction was quenched by adding 1 mL water. The aqueous layer was extracted by dichloromethane 2 mL x 3. The organic layers were combined, dried over sodium sulfate, and concentrated to give the crude product. Purification was performed on Waters reverse phase HPLC (C18 column, mobile phase: water with 0.1% formic acid, and methanol with 0.1% formic acid) to yield the mixture of two regioisomers 9. The mixture of regioisomers 9 was further separated by SFC (OD-H column) in order to give enantiomers.

19. Method for Preparative HPLC/UV

LC-MS chromasolv grade methanol and formic acid were obtained from Sigma-Aldrich (St. Louis, Mo.). Milli-Q water as an ultrapure laboratory grade water was used in aqueous mobile phase.

Chromatographic separation was performed on an Xbridge OBD C18 5 µm, 30×50 mm column using an waters high performance liquid chromatography system. Data were acquired using Masslynx v. 4.1. This was coupled to an waters photodiode array detector, which acquired UV data from 230-500 nm. The total flow rate was 20 mL/min. Mobile phase A was 0.1% formic acid in MilliQ H2O; while mobile phase B was 0.1% formic acid in methanol. The HPLC column was maintained at 20° C. and the gradient program were listed below:

HPLC Method A:
started at 20% B (0.1% formic acid in methanol), held for 1 min, changed to 40% B over 2 min, to 50% B over 4 minutes, to 65% B over 15 min, then 95% B over 3 min, held for 4 minutes, then to 20% B over 1 minutes.

HPLC Method B:
started at 5% B (0.1% formic acid in methanol), held for 1 min, changed to 40% B over 2 min, to 55% B over 19 min, then 95% B over 3 min, held for 4 minutes, then to 5% B over 1 minutes.

HPLC Method C:

started at 20% B (0.1% formic acid in methanol), held for 1 min, changed to 65% B over 1 min, to 85% B over 13 minutes, to 95% B over 1 min, held for 3 minutes, then to 20% B over 1 minutes.

HPLC Method D:

started at 20% B (0.1% formic acid in methanol), held for 1 min, changed to 70% B over 1 min, to 85% B over 13 minutes, to 95% B over 1 min, held for 3 minutes, then to 20% B over 1 minutes.

20. Method for Preparative SFC/UV

LC-MS chromasolv grade methanol and formic acid were obtained from Sigma-Aldrich (St. Louis, Mo.). Chromatographic separation was performed on a Chiralcel ODH 2 cm×25 mm column (Daicel chemical Ind, LTD) using an Berger Auto Prep Supercritical Fluid Chromatography system (Mettler Toledo). This was coupled to a photodiode array detector, which acquired UV data from 240 nm. The total flow rate was 50 mL/min. Solvent mobile phase was $CO_2$, while solvent modifier was methanol. The ODH column was maintained at 35° C. and the solvent modifier program were listed below:

SFC Method A:

started at 5% Methanol, changed to 50% methanol at rate 5 mL/min, held for 2.6 min, then to 10% methanol at rate 99 mL/min.

SFC Method B:

started at 5% Methanol, changed to 20% methanol at rate 3 mL/min, held for 8 min, to 40% methanol at rate 5 mL/min, held for 2.7 min, then to 10% methanol at rate 99 mL/min.

SFC Method C:

started at 10% Methanol, changed to 20% methanol at rate 3 mL/min, held for 15 min, to 50% methanol at rate 99 mL/min, held for 0.96 min, then to 10% methanol at rate 99 mL/min.

SFC Method D:

started at 30% Methanol, changed to 50% methanol at rate 2.5 mL/min, held for 3 min, to 70% methanol at rate 99 mL/min, held for 1.39 min, then to 30% methanol at rate 99 mL/min.

SFC Method E:

started at 35% Methanol, changed to 50% methanol at rate 2.5 mL/min, held for 5 min, to 70% methanol at rate 99 mL/min, held for 1.39 min, then to 30% methanol at rate 99 mL/min.

SFC Method F:

started at 8% Methanol, changed to 13% methanol at rate 3.0 mL/min, held for 7.79 min, to 50% methanol at rate 9.15 mL/min, held for 0.3 min, to 50% methanol at rate 99 mL/min, held for 0.8 min, then to 10% methanol at rate 99 mL/min.

B. Evaluation of Inhibitory Activity Against MDMX

Activity of the compounds were compared to the activity of Nutlin, which is shown below.

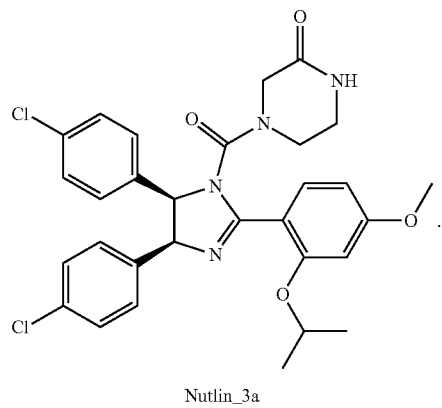 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

Nutlin_3a

Figure 1B:
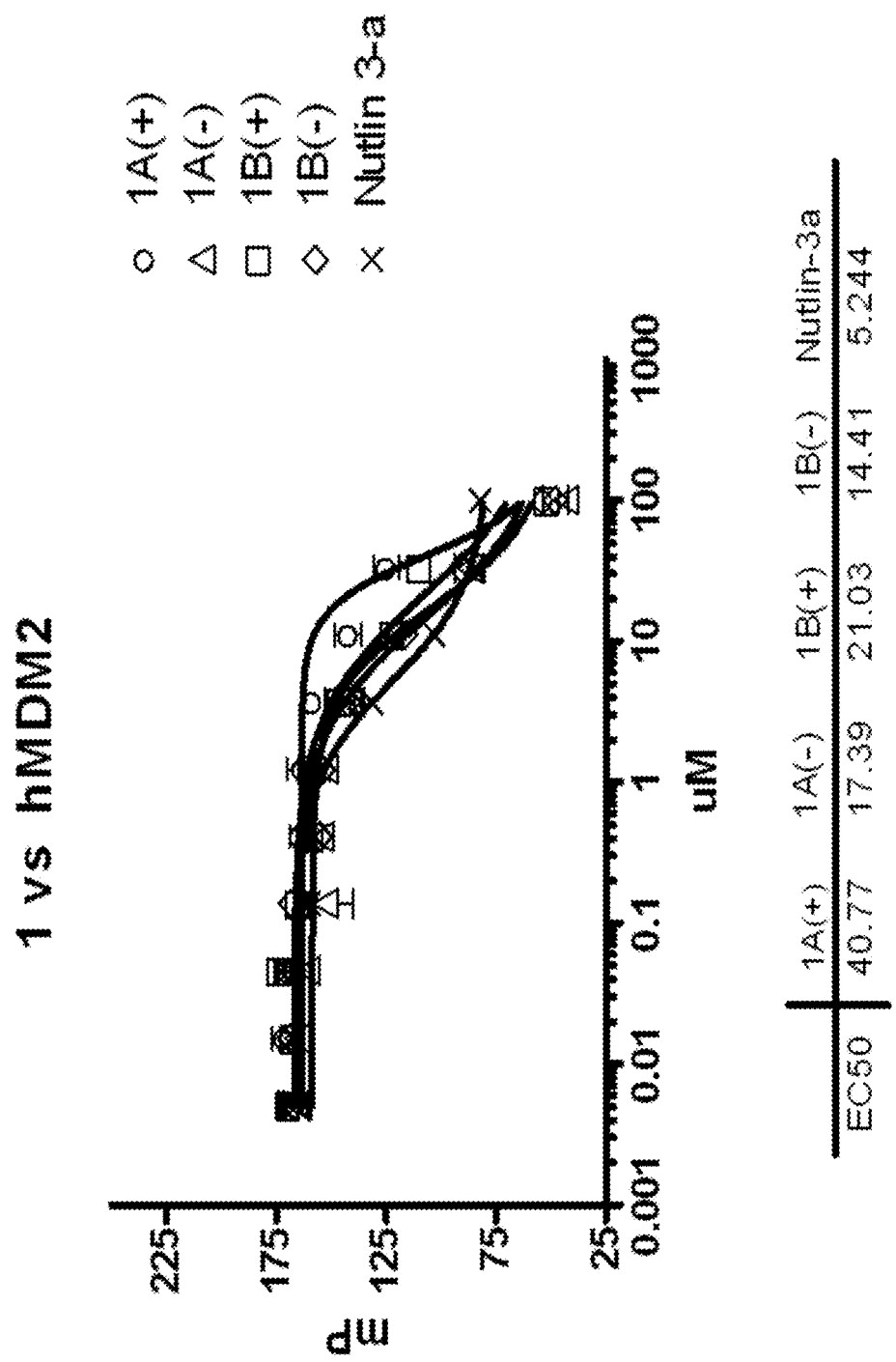

FIG. 1A and FIG. 1B show competitive binding curves of four isomers of 1 against hMDMX (FIG. 1A) and hMDM2 (FIG. 1B). $EC_{50}$ was given in μM. The stereochemistry of each isomer was signed based on the optical rotation compared to that of Nutlin-3a ([α]=−151.7° in Methanol, 18.5° C.).

Two nutlin analogues, SJ558295 and SJ558304, had selected as hit candidates in terms of their inhibitory activity against MDMX in fluorescence polarization (FP) assay. For further evaluation with these hit compounds, several pre-in vivo studies such as physico-chemical property and metabolic stability were carried out and its result listed in Table 1. Both analogs possessed reasonable in vitro PK profiles with uM level of IC50 value against MDMX in FP assay so further biological evaluation and chemical modification performed to optimization this imidazoline series of molecule as a potent MDMX inhibitors.

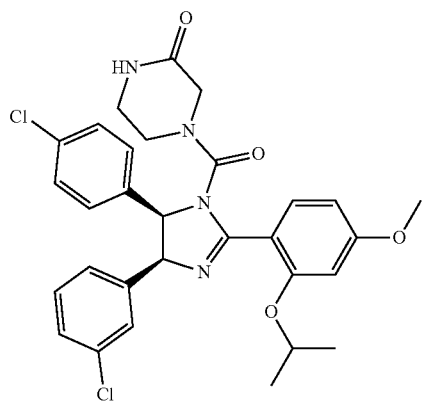

SJ000558295
FP IC50 (hMDM2) = 9.1 uM
FP IC50 (hMDMX) = 9.0 uM

51 -continued

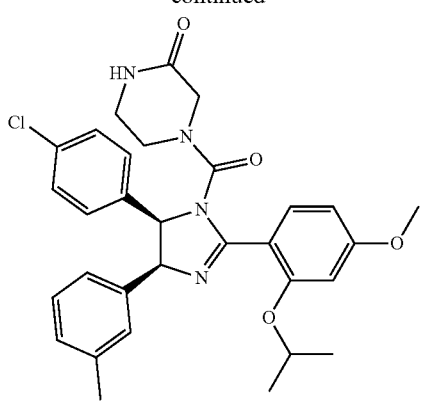

SJ000558304
FP IC50 (hMDM2) = 14.4 uM
FP IC50 (hMDMX) = 9.0 uM

TABLE 1

DATA FOR IN VITRO PK STUDY

|  | SJ000558295 | SJ000558304 |
|---|---|---|
| uSOL pH 7.4 (uM) | 37.8 | 57.4 |
| uSOL pH 3 (uM) | 72.7 | 66.7 |
| PAMPA pH 7.4 (10−6 cm/s) | 694.1 | 867.2 |
| R % pH 7.4 | 78 | 79 |
| PAMPA pH 3 (10−6 cm/s) | 222.4 | 72.1 |
| R % pH 3 | 76 | 42 |
| mouse liver microsome t(½) (hr) | 2.17 | 0.73 |
| mouse liver microsome CLint' (ml/min/kg) | 24.9 | 73.9 |
| human liver microsome t(½) (hr) | 1.72 | 1.46 |
| Human liver microsome CLint' (ml/min/kg) | 12.1 | 14.2 |
| mPlasma stability t(½) (hr) | >48 | >48 |
| hPlasma stability t(½) (hr) | >48 | >48 |
| PBS pH 7.4 stability t(½) (hr) | >48 | >48 |
| SGF stability t(½) (hr) | 30.13 | >48 |

Figure 2:
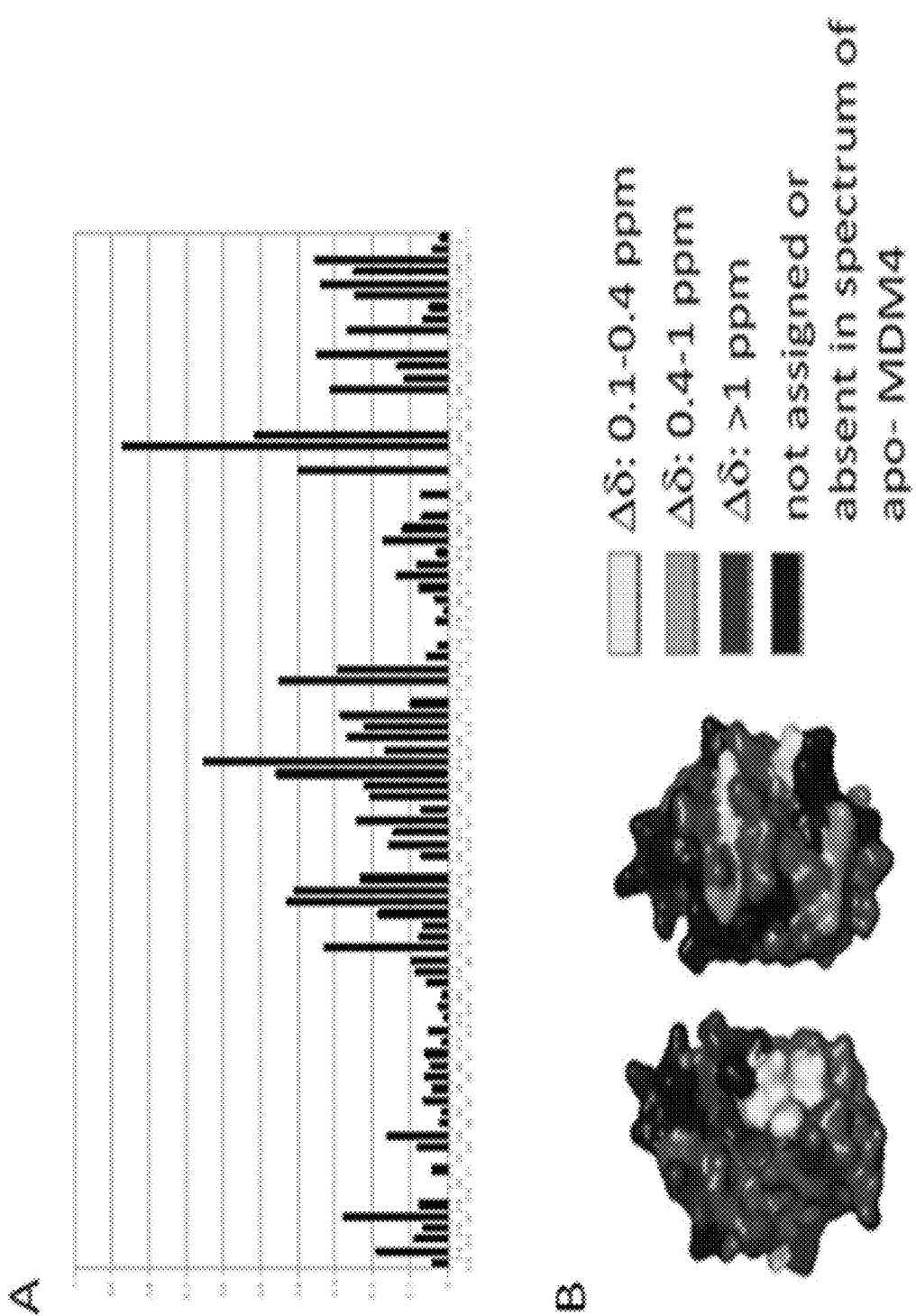
FIG. 2 shows SJ558295 Binding-Induced NMR Chemical Shift Perturbations of MDM4. A. Difference in chemical shift perturbation of MDM4-SJ558295 complex and MDM4-P53_NTD complex versus amino acid B. Chemical shift mapping of SJ558295 on MDM4 coded by the level of chemical shift perturbations

To verify further whether the identified active compounds from primary FP assay can disrupt MDMX-p53 or not, a NMR based assay was used to define binding regions via measuring level of $^1$H and $^{15}$N chemical shift perturbations on the residues of MDM4 protein. As an alternative method to detect the binding of small molecules to MDM4, 2D [$^{15}$N, $^1$H] HSQC spectra were measured. The chemical shift perturbations observed in these experiments identify the residues of MDM4 that are directly involved in the binding of small molecules. Coded structures of MDM4 depicting the degree of chemical shift perturbation with various nutlin analogues and the data for SJ558295 are shown in FIG. 2.

According to the result of NMR based binding assay, the promising derivatives that were confirmed to bind to MDMX listed on Table 2.

TABLE 2

ANALOGUES CONFIRMED TO BIND ON MDM4 BY NMR SCREENING

| SJ Number | Structure |
|---|---|
| Nutlin 3a | 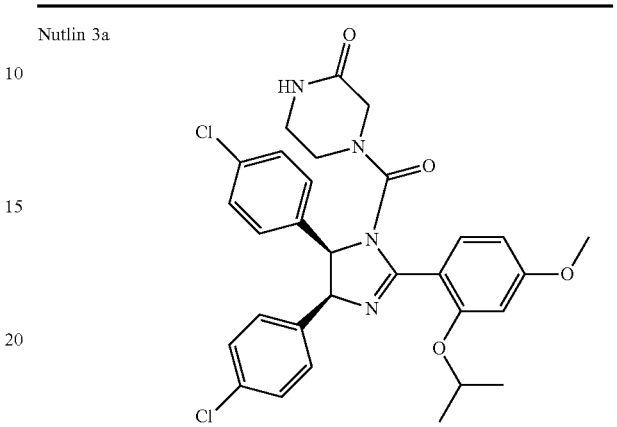 |
| SJ558299-1 | 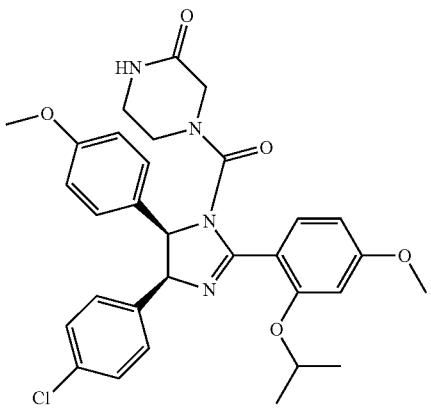 |
| SJ558295-1 | 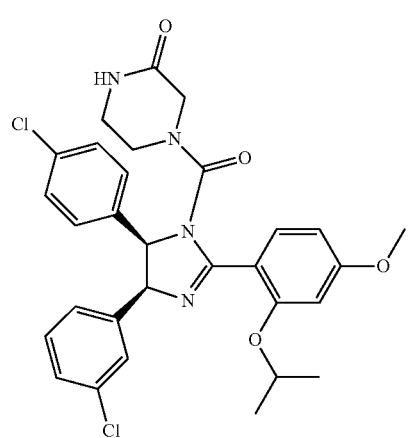 [SMILES: COc1ccc(C2=N[C@@H](c3cccc(Cl)c3)[C@@H](c3ccc(Cl)cc3)N2C(=O)N2CCNC(=O)C2)c(OC(C)C)c1] |

TABLE 2-continued
ANALOGUES CONFIRMED TO BIND ON MDM4 BY NMR SCREENING
| SJ Number | Structure |
| --- | --- |
| SJ558300-1 | 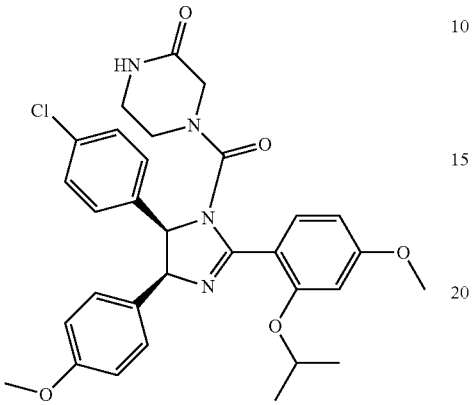 |
| SJ560615-1 | 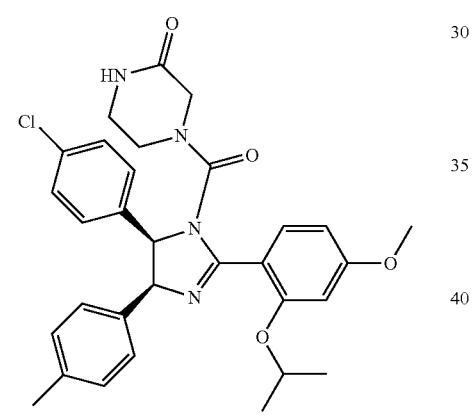 |
| SJ558302-1 | 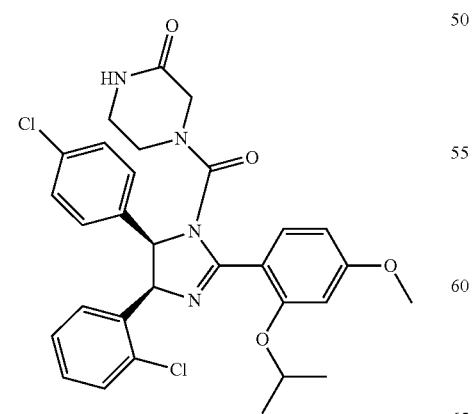 |
| SJ560616-1 | 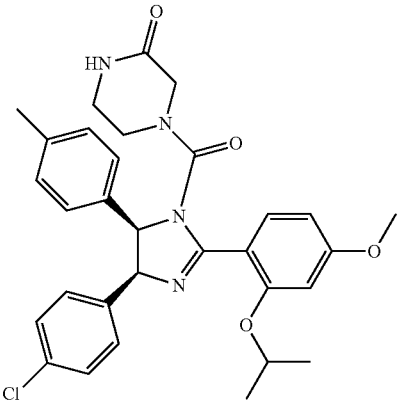 |
| SJ558303-1 | 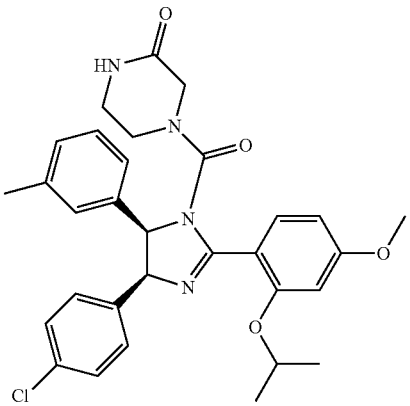 |
| SJ558304-1 | 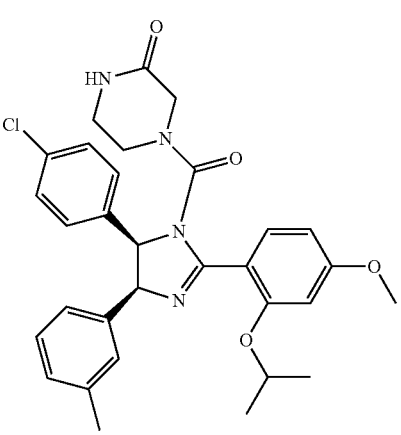 [SMILES: COc1ccc(C2=N[C@@H](c3cccc(C)c3)[C@@H](c3ccc(Cl)cc3)N2C(=O)N2CCNC(=O)C2)c(OC(C)C)c1] |

TABLE 2-continued

ANALOGUES CONFIRMED TO BIND ON MDM4 BY NMR SCREENING

| SJ Number | Structure |
|---|---|
| SJ558306-1 | 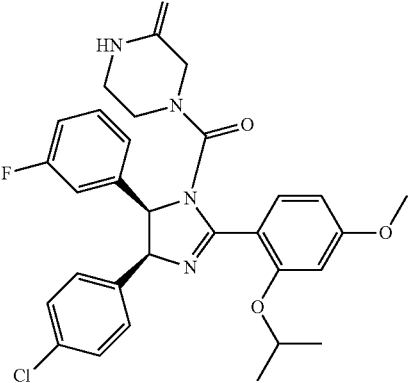 |
| SJ558305-1 | 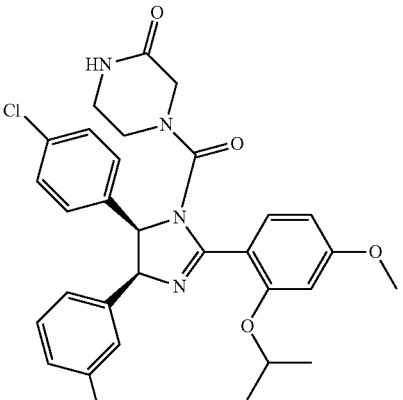 |

Figure 3:
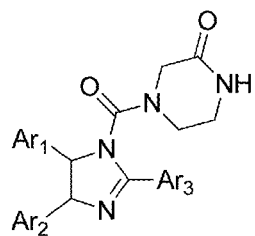
FIG. 3 shows a representative formula for synthetic derivatives.

Based on the promising data from Fluorescence polarization (FP) and NMR assay for the nutlin-3a and its analogs, a parallel synthetic strategy applied to generate imidazoline focused library by modifying Ar1, Ar2 and Ar3 group to optimize binding affinity to MDMX with various substituted aryl groups in FIG. 3 using schemes 1 and 2.

General Scheme 1

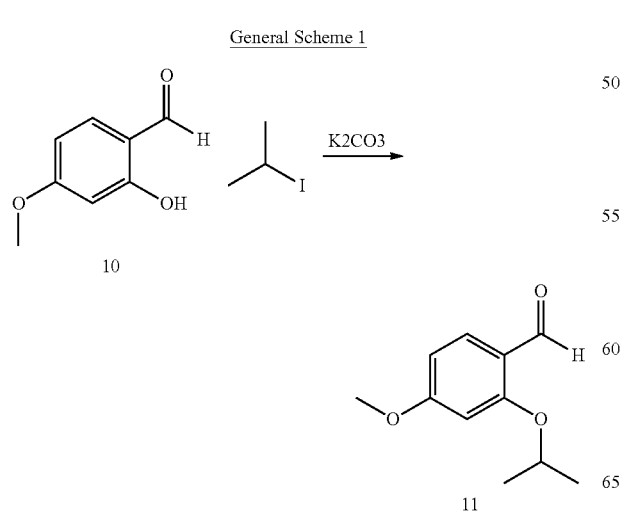

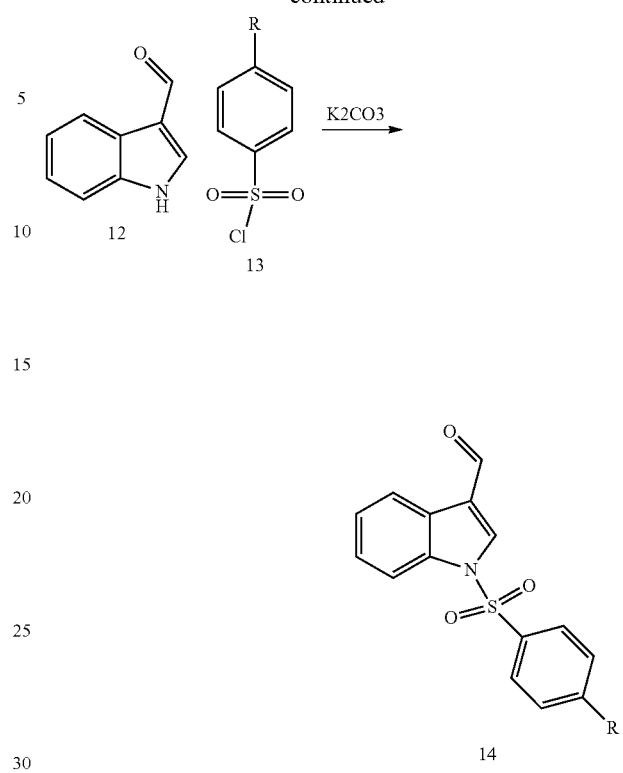

General Scheme 2

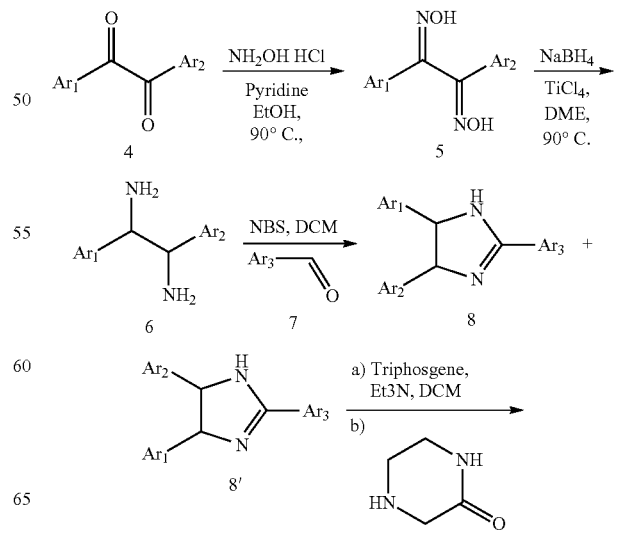

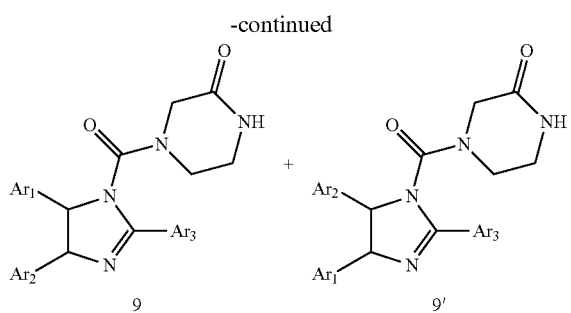

Figure 4A:
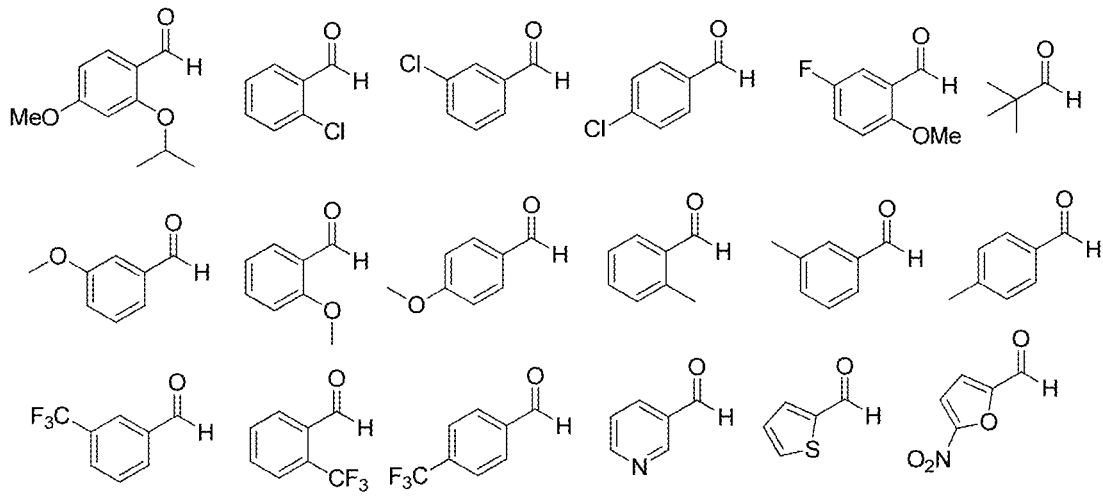
FIGS. 4a and 4b show representative imidazoline library building blocks.
Figure 4B:
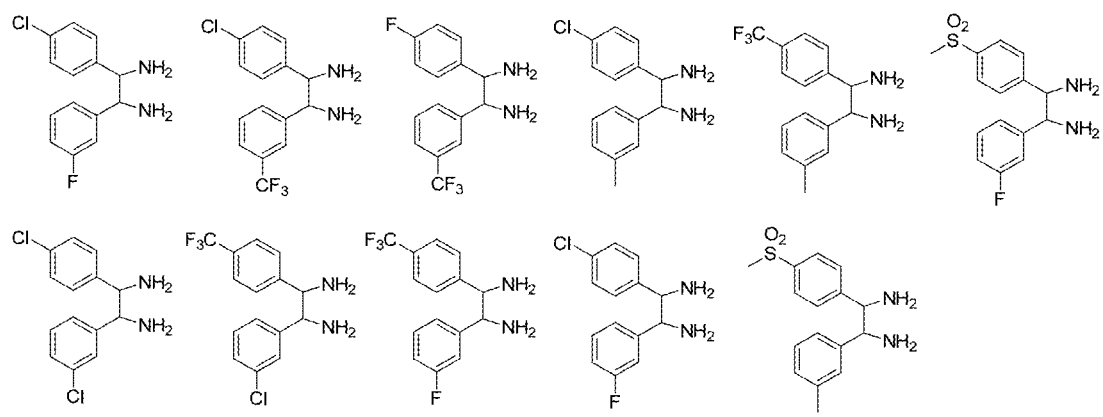

To prepare imidazoline scaffold focused library via parallel synthetic approach, two types of library building blocks, aldehydes (7) and diaryl vicinal diamines (6), needed to be prepared with structural diversity. Functionalized aldehydes building block (FIG. 4a) prepared by both syntheses via scheme 1 and purchasing commercial reagents. On the other hand, the various aryl substituted diamine building block (FIG. 4b) synthesized through general scheme 2.

Condensation of aldehydes and diamines followed by introducing piperazin-one carbonyl on the nitrogen of imidazoline generated around 160 library compounds and its representative analogs that were prepared via parallel synthetic approach listed in Table 3 for the compounds tested against FP assay and Table 4 for total analogs prepared.

TABLE 3

IMIDAZOLINE ANALOGS TESTED AGAINST FP ASSAY WITH THEIR PURIFICATION METHODS

| SJ_num | Structure | FP Assay hMDMX IC$_{50}$ (uM) | SFC Method | Purification HPLC Method |
|---|---|---|---|---|
| SJ000558297-2 | 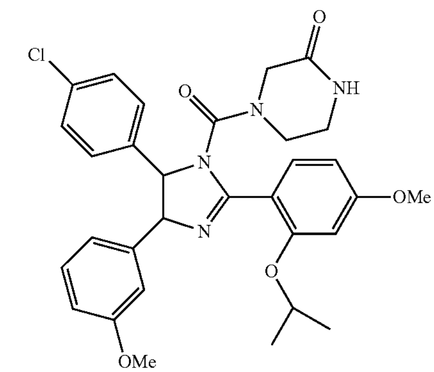 [SMILES: COc1cccc(C2N=C(c3ccc(OC)cc3OC(C)C)N(C(=O)N3CCNC(=O)C3)C2c2ccc(Cl)cc2)c1] | 39.4 | A | A |
| SJ000558298-1 | 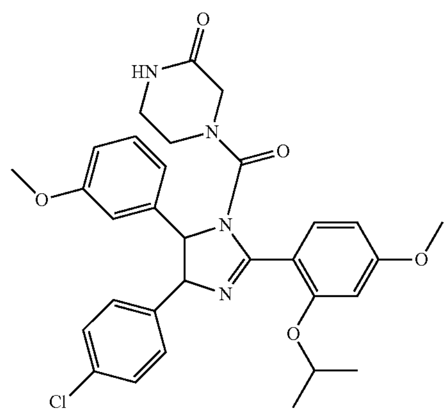 | 2.0 | A | A |
| SJ000558300-1 | 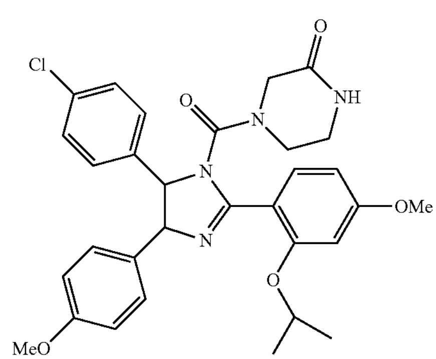 [SMILES: COc1ccc(C2N=C(c3ccc(OC)cc3OC(C)C)N(C(=O)N3CCNC(=O)C3)C2c2ccc(Cl)cc2)cc1] | >40 | B | B |

TABLE 3-continued

IMIDAZOLINE ANALOGS TESTED AGAINST FP ASSAY WITH THEIR PURIFICATION METHODS

| SJ_num | Structure | FP Assay hMDMX IC$_{50}$ (uM) | SFC Method | Purification HPLC Method |
|---|---|---|---|---|
| SJ000558295-1 | 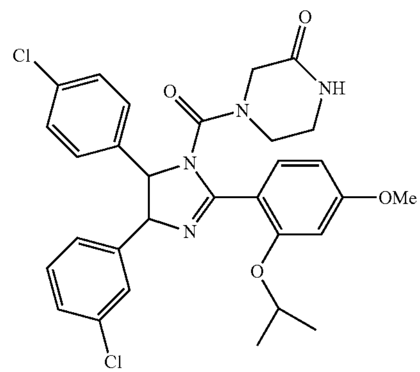 [SMILES: COc1ccc(C2=NC(c3cccc(Cl)c3)C(c3ccc(Cl)cc3)N2C(=O)N2CCNC(=O)C2)c(OC(C)C)c1] | 9.0 | A | A |
| SJ000558296-1 | 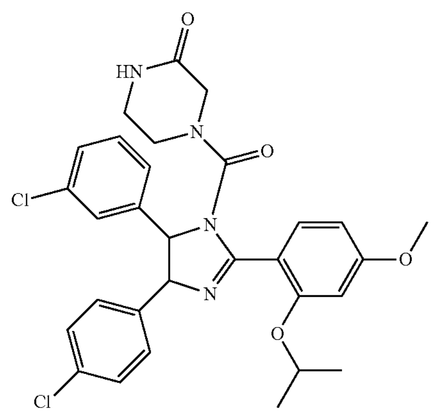 [SMILES: COc1ccc(C2=NC(c3ccc(Cl)cc3)C(c3cccc(Cl)c3)N2C(=O)N2CCNC(=O)C2)c(OC(C)C)c1] | 15.6 | A | |
| SJ000558301-1 | 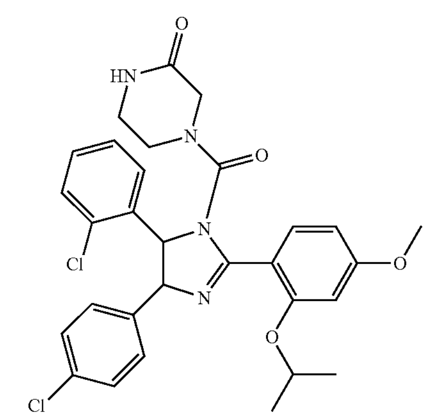 [SMILES: COc1ccc(C2=NC(c3ccc(Cl)cc3)C(c3ccccc3Cl)N2C(=O)N2CCNC(=O)C2)c(OC(C)C)c1] | >40 | C | B |

TABLE 3-continued

IMIDAZOLINE ANALOGS TESTED AGAINST FP ASSAY WITH THEIR PURIFICATION METHODS

| SJ_num | Structure | FP Assay hMDMX IC$_{50}$ (uM) | SFC Method | Purification HPLC Method |
|---|---|---|---|---|
| SJ000558302-1 | 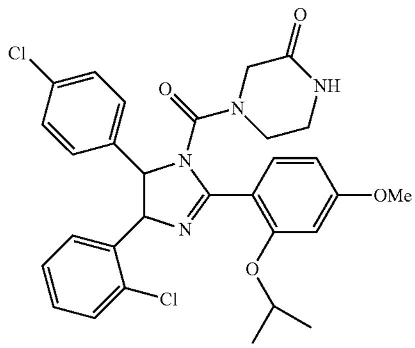 [SMILES: COc1ccc(C2=NC(c3ccccc3Cl)C(c3ccc(Cl)cc3)N2C(=O)N2CCNC(=O)C2)c(OC(C)C)c1] | 9.1 | C | B |
| SJ000558304-1 | 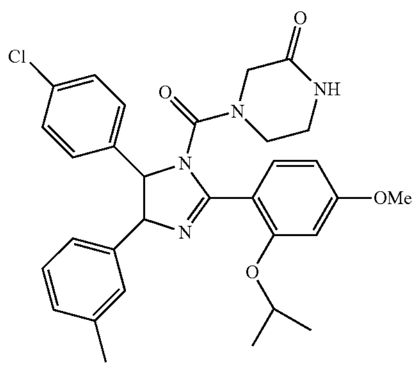 [SMILES: COc1ccc(C2=NC(c3cccc(C)c3)C(c3ccc(Cl)cc3)N2C(=O)N2CCNC(=O)C2)c(OC(C)C)c1] | 9.0 | C | B |
| SJ000560615-1 | 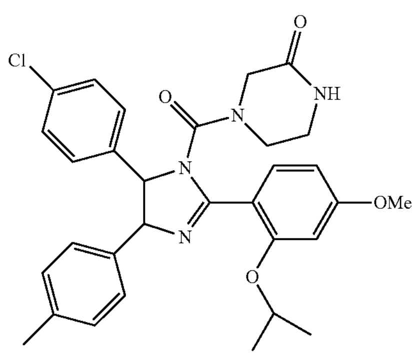 [SMILES: COc1ccc(C2=NC(c3ccc(C)cc3)C(c3ccc(Cl)cc3)N2C(=O)N2CCNC(=O)C2)c(OC(C)C)c1] | >40 | | B |
| SJ000560616-1 | 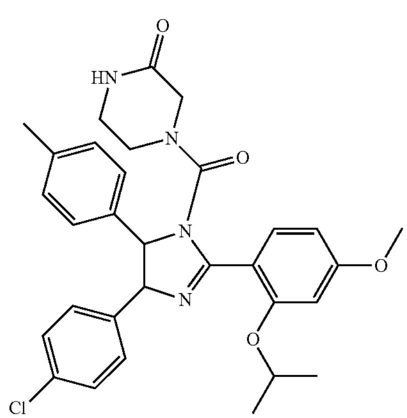 [SMILES: COc1ccc(C2=NC(c3ccc(Cl)cc3)C(c3ccc(C)cc3)N2C(=O)N2CCNC(=O)C2)c(OC(C)C)c1] | 25 | | B |

TABLE 3-continued

IMIDAZOLINE ANALOGS TESTED AGAINST FP ASSAY WITH THEIR PURIFICATION METHODS

| SJ_num | Structure | FP Assay hMDMX IC$_{50}$ (uM) | SFC Method | Purification HPLC Method |
|---|---|---|---|---|
| SJ000558305-1 | 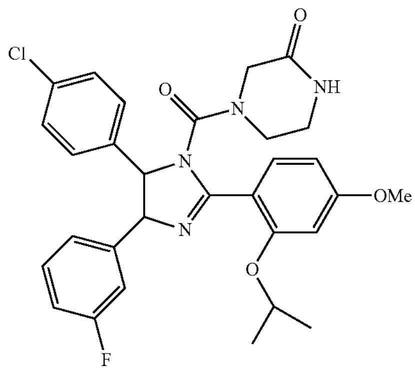 [SMILES: COc1ccc(C2=NC(c3cccc(F)c3)C(c3ccc(Cl)cc3)N2C(=O)N2CCNC(=O)C2)c(OC(C)C)c1] | 19.4 | C | B |
| SJ000558306-1 | 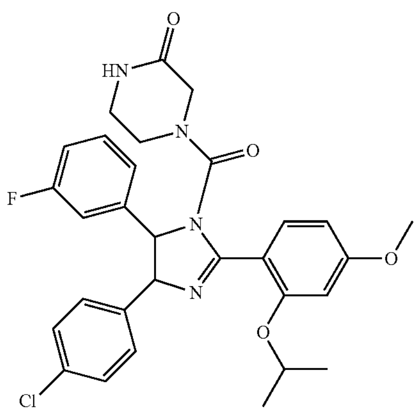 [SMILES: COc1ccc(C2=NC(c3ccc(Cl)cc3)C(c3cccc(F)c3)N2C(=O)N2CCNC(=O)C2)c(OC(C)C)c1] | 9.7 | C | B |

TABLE 4
STRUCTURES OF 160 IMIDAZOLINE ANALOGS SYNTHESIZED VIA PARALLEL APPROACH
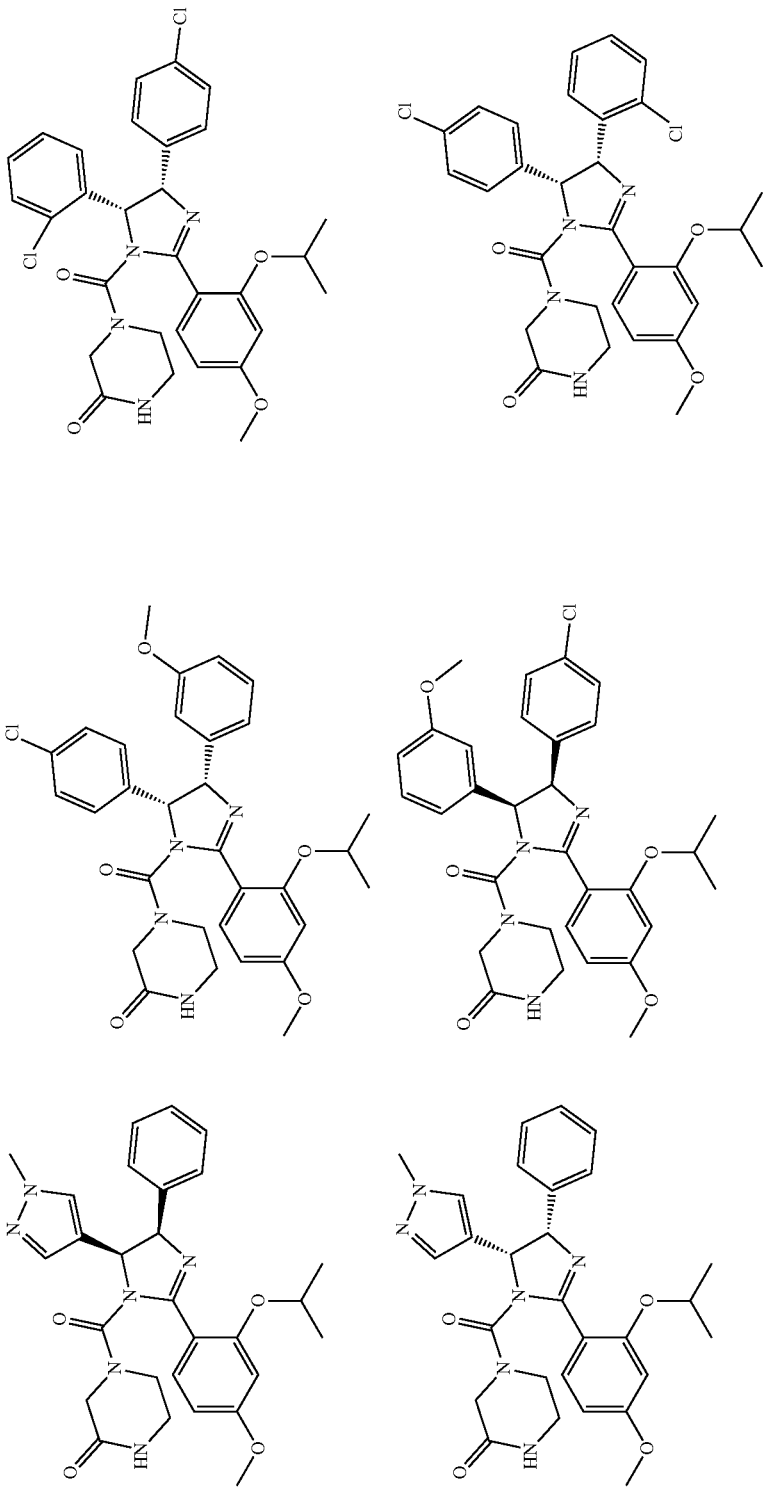

TABLE 4-continued
STRUCTURES OF 160 IMIDAZOLINE
ANALOGS SYNTHESIZED VIA PARALLEL APPROACH
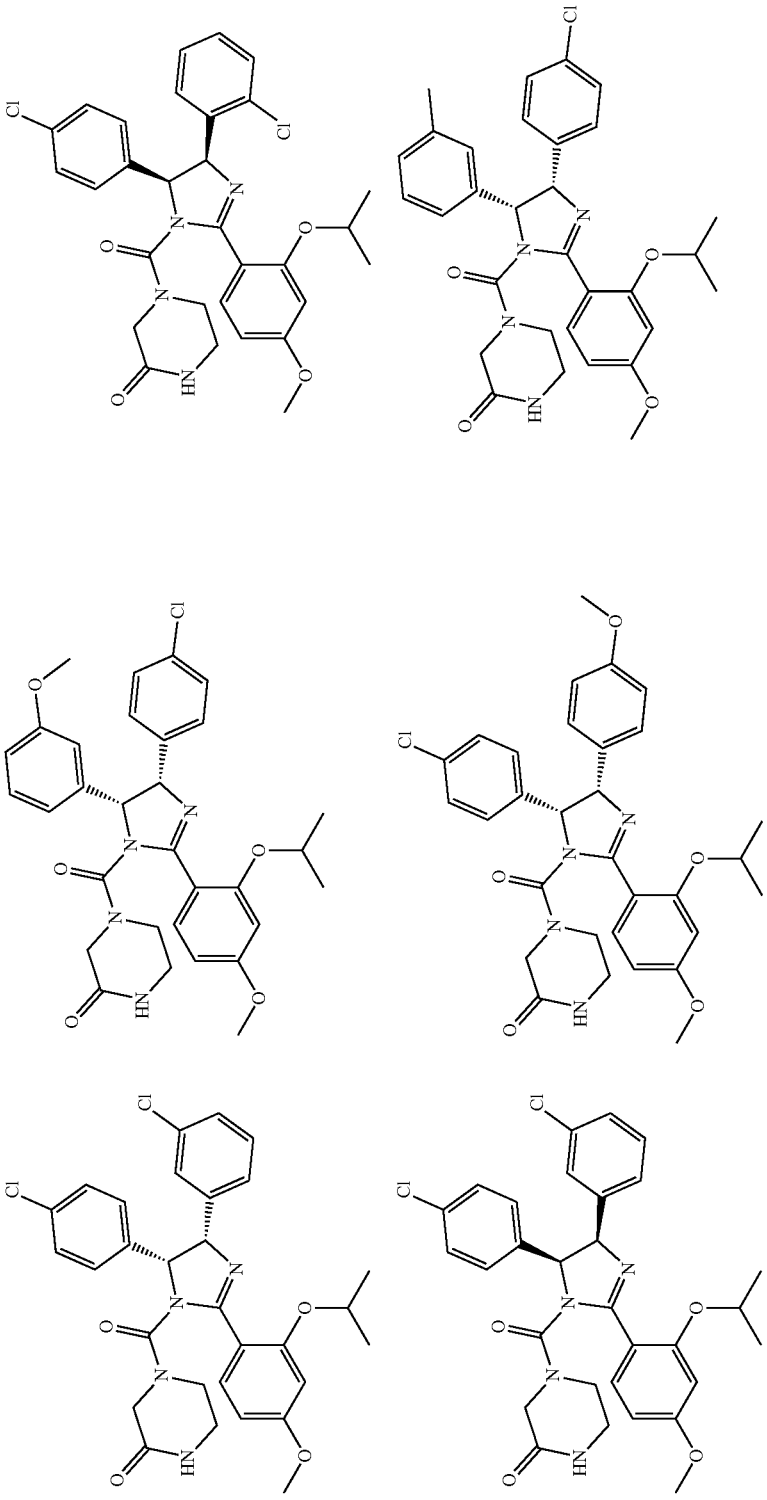

TABLE 4-continued
STRUCTURES OF 160 IMIDAZOLINE ANALOGS SYNTHESIZED VIA PARALLEL APPROACH
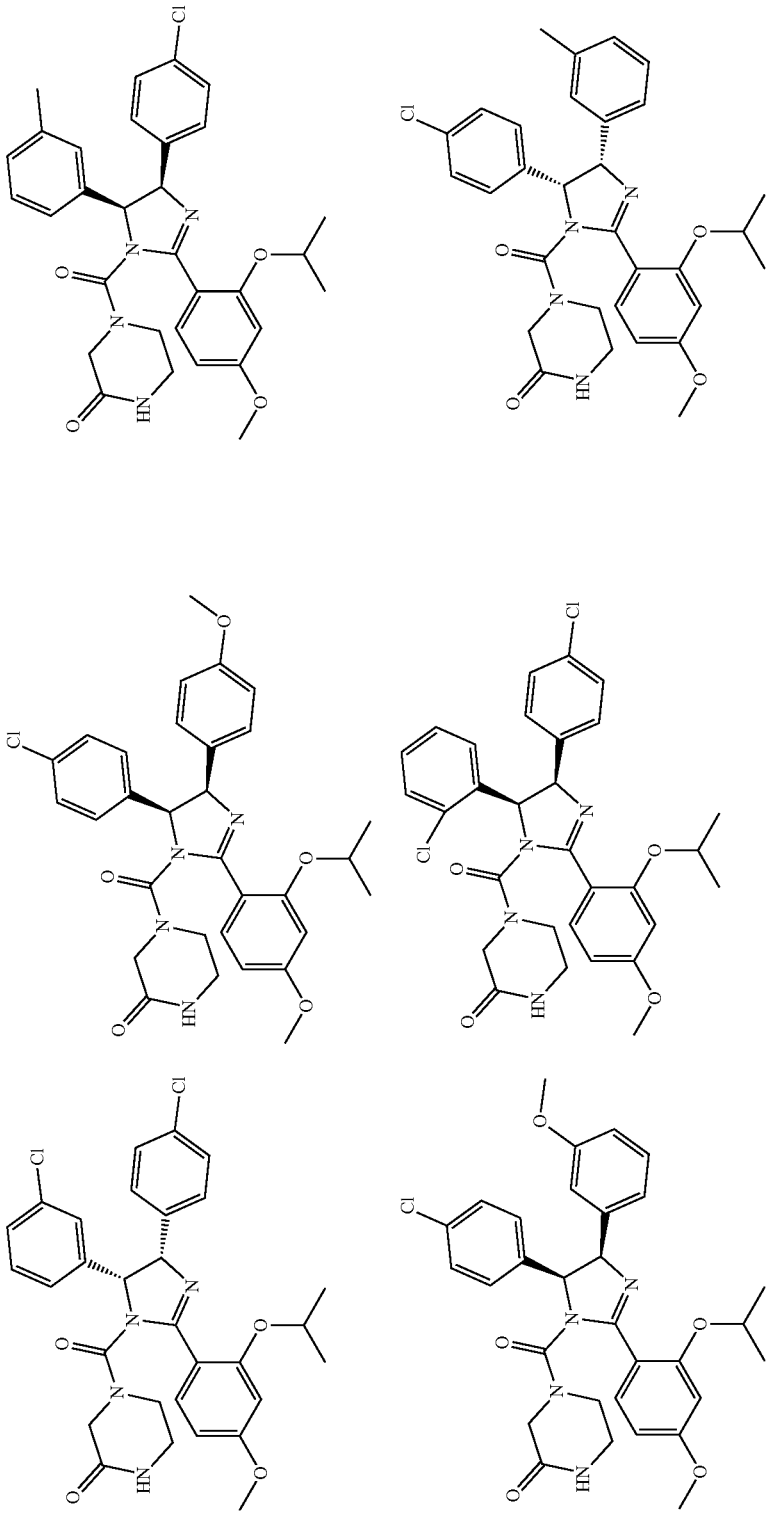

TABLE 4-continued
STRUCTURES OF 160 IMIDAZOLINE ANALOGS SYNTHESIZED VIA PARALLEL APPROACH
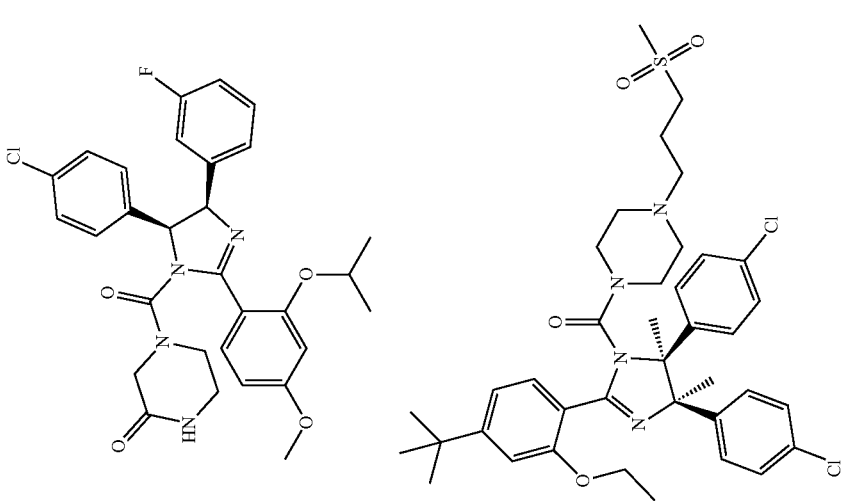

TABLE 4-continued
STRUCTURES OF 160 IMIDAZOLINE ANALOGS SYNTHESIZED VIA PARALLEL APPROACH
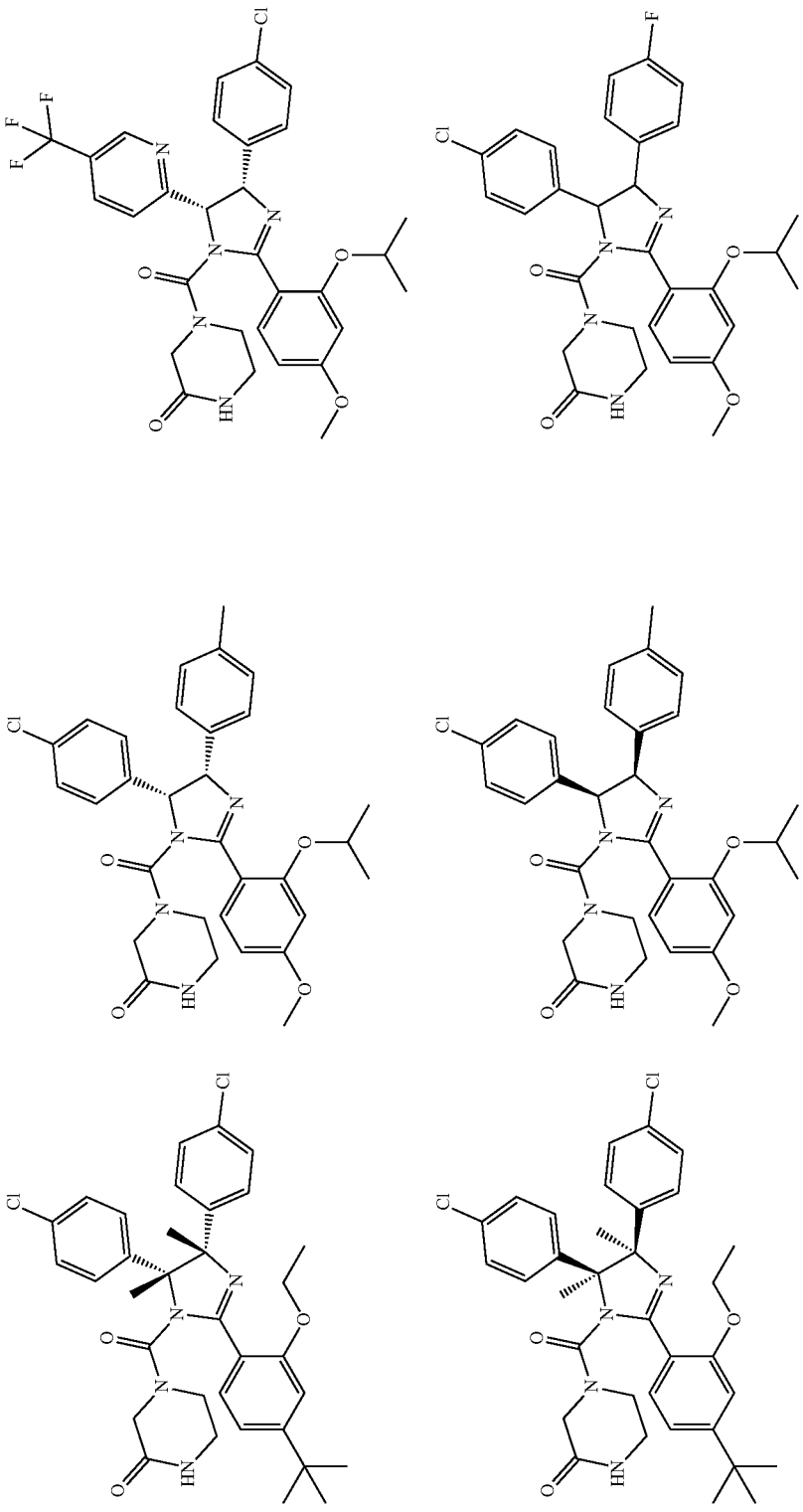

TABLE 4-continued
STRUCTURES OF 160 IMIDAZOLINE
ANALOGS SYNTHESIZED VIA PARALLEL APPROACH
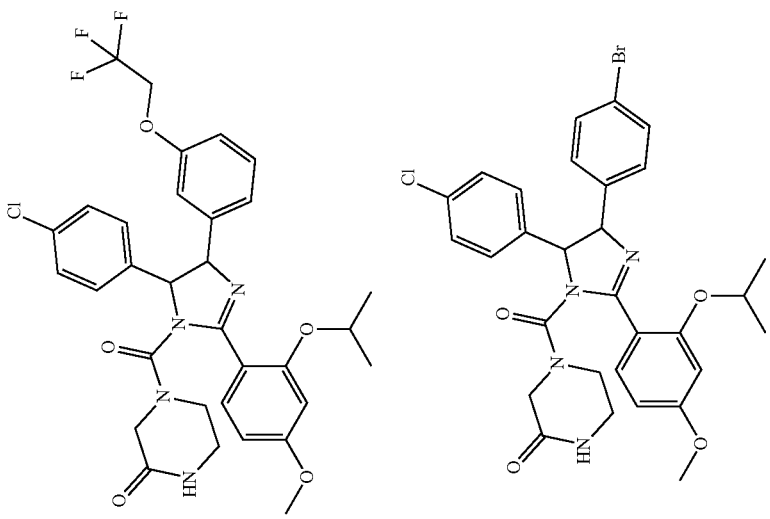
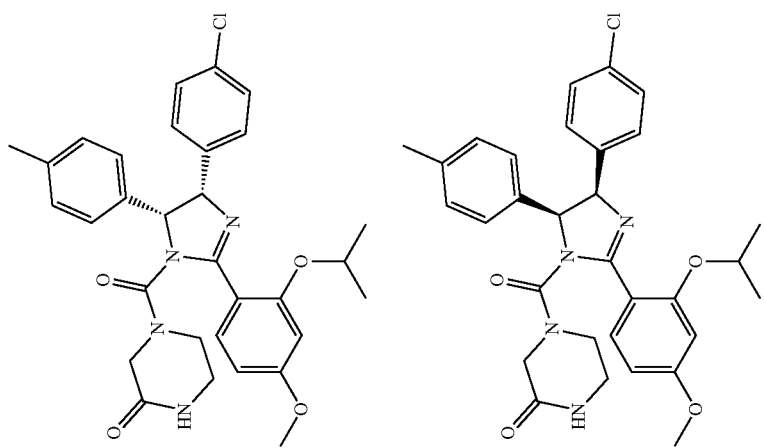
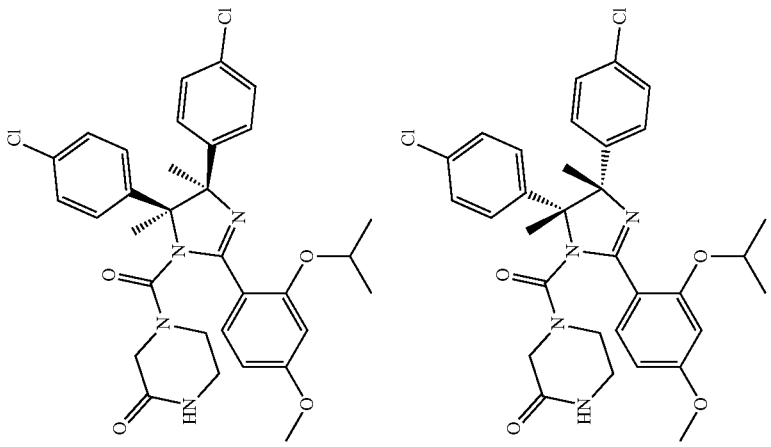

TABLE 4-continued
STRUCTURES OF 160 IMIDAZOLINE ANALOGS SYNTHESIZED VIA PARALLEL APPROACH
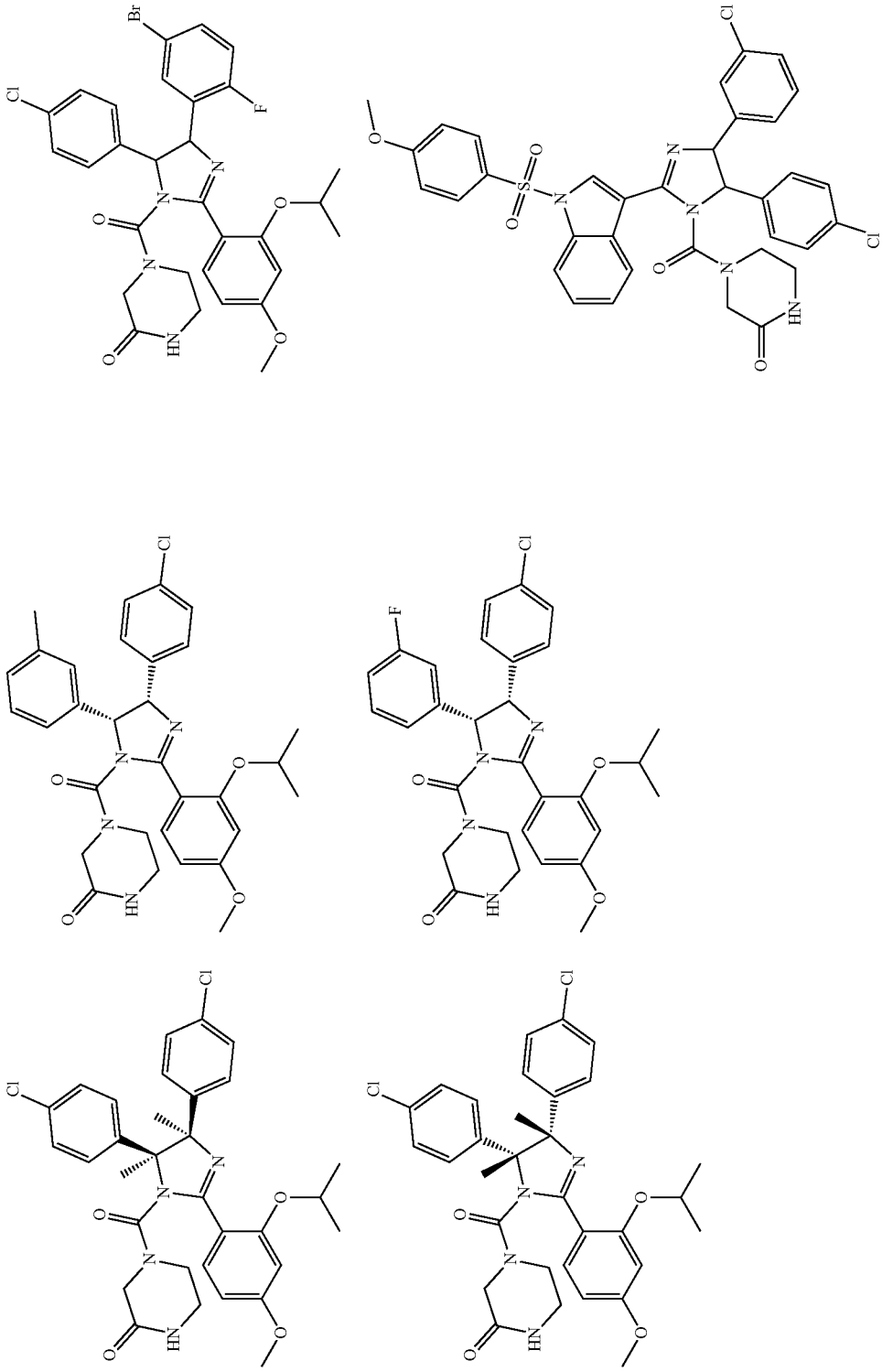

TABLE 4-continued
STRUCTURES OF 160 IMIDAZOLINE
ANALOGS SYNTHESIZED VIA PARALLEL APPROACH
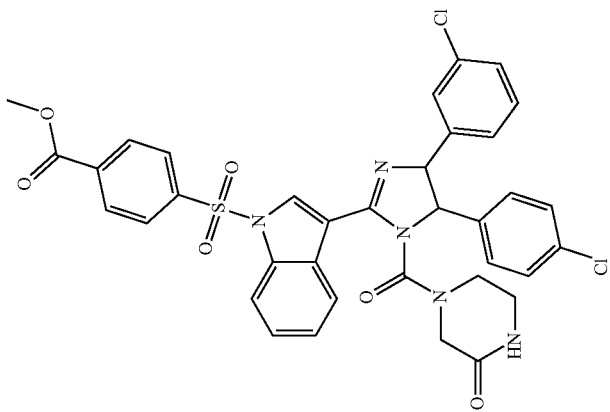
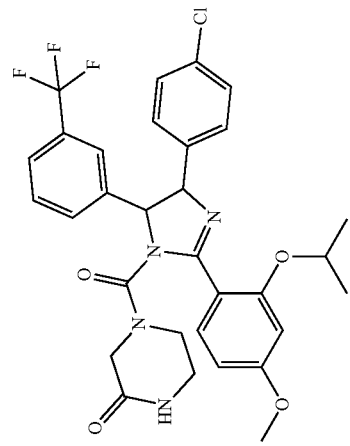
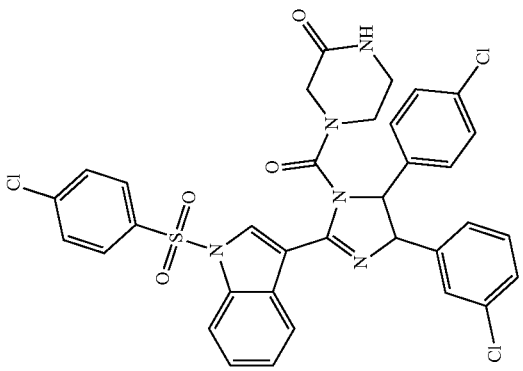
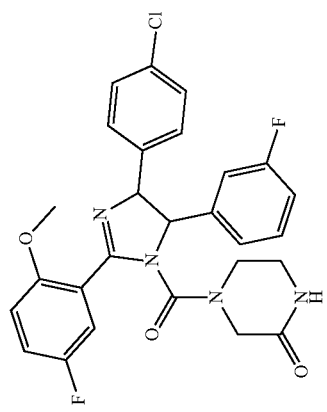
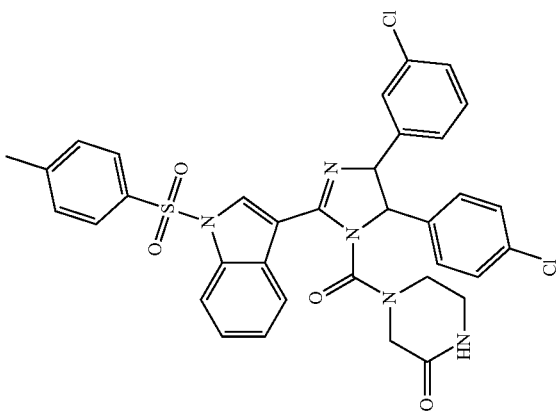
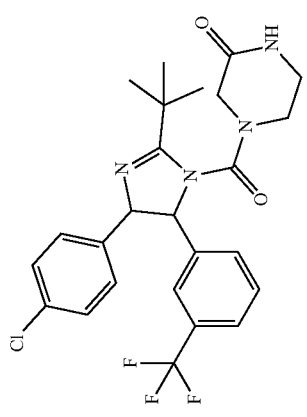

TABLE 4-continued
STRUCTURES OF 160 IMIDAZOLINE ANALOGS SYNTHESIZED VIA PARALLEL APPROACH
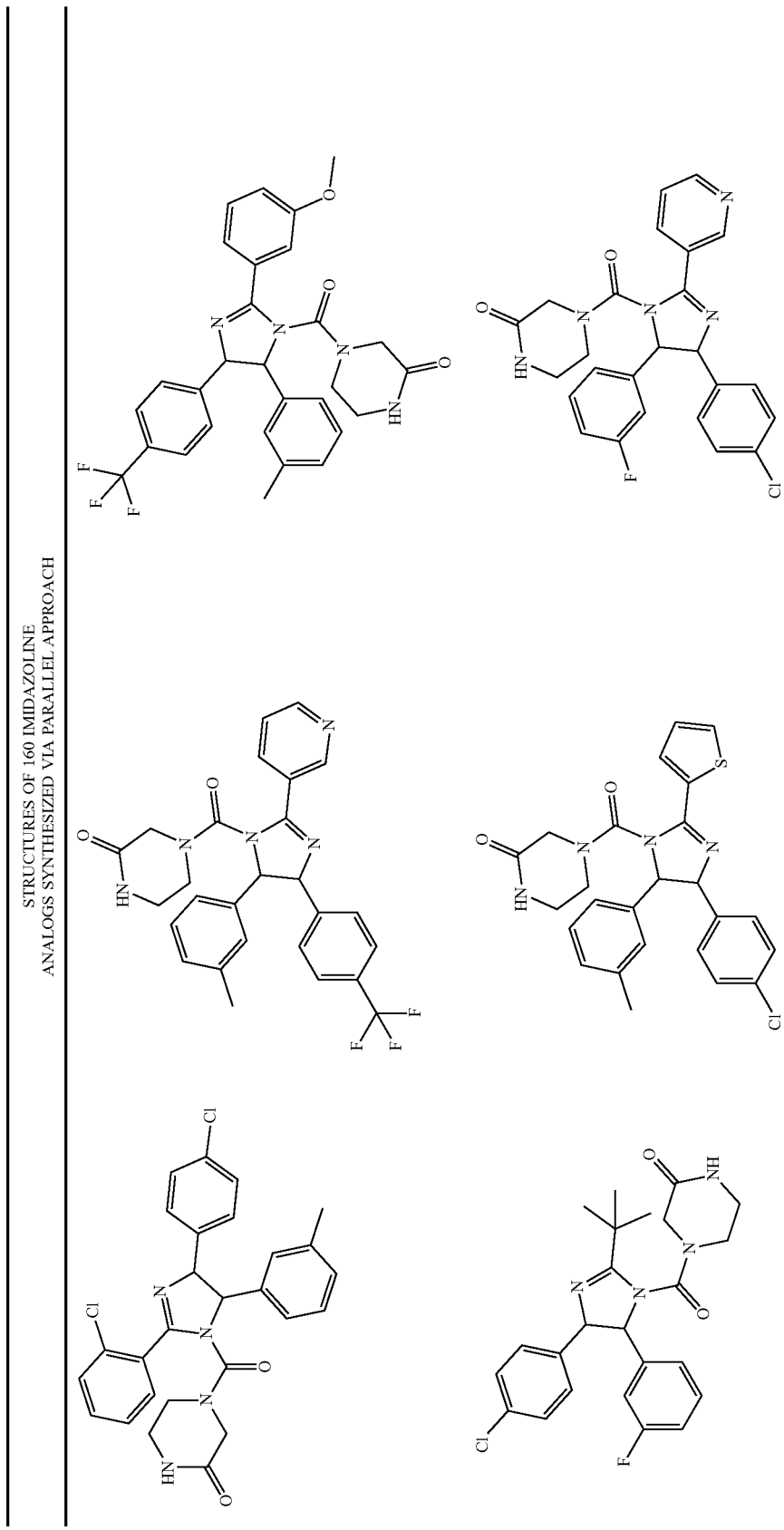

TABLE 4-continued
STRUCTURES OF 160 IMIDAZOLINE ANALOGS SYNTHESIZED VIA PARALLEL APPROACH
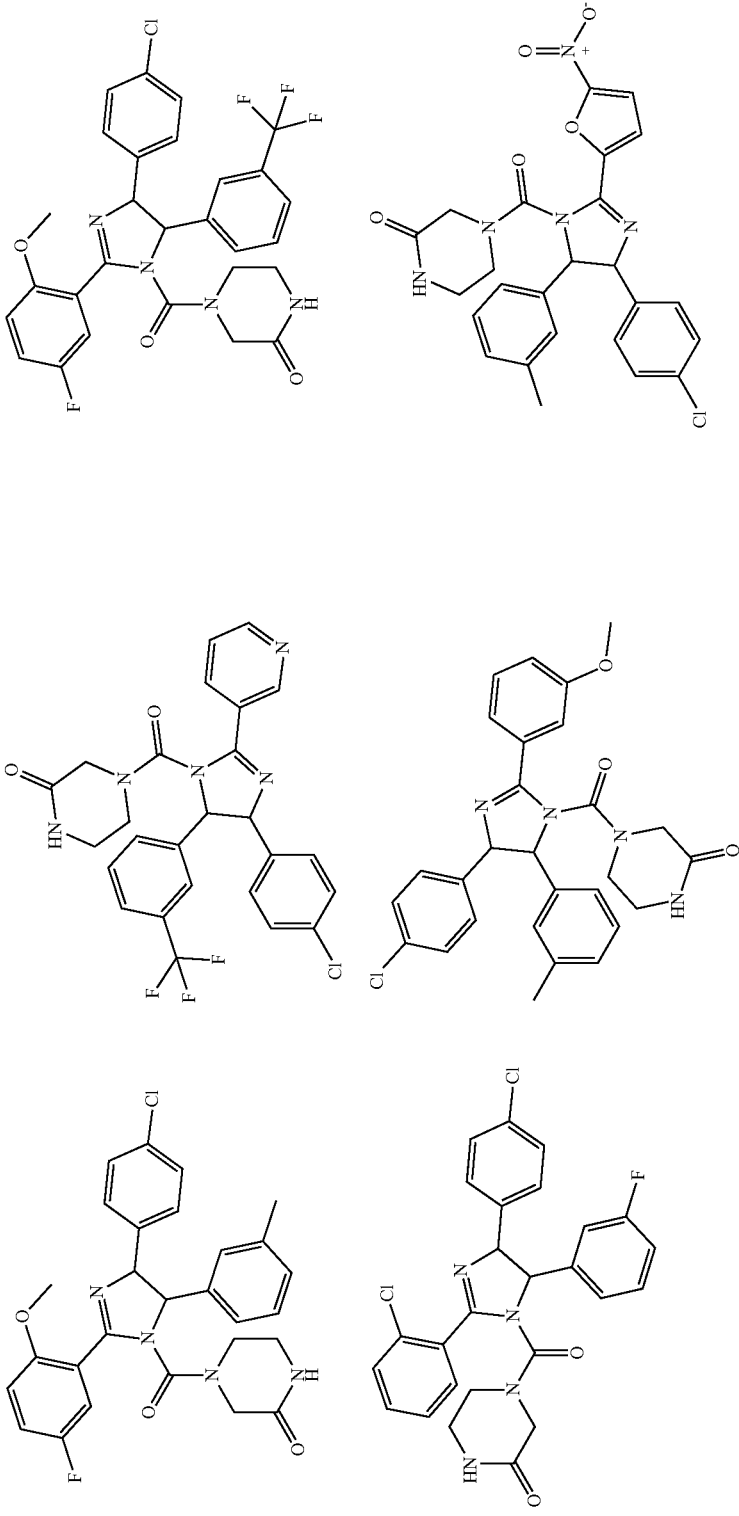

TABLE 4-continued
STRUCTURES OF 160 IMIDAZOLINE ANALOGS SYNTHESIZED VIA PARALLEL APPROACH
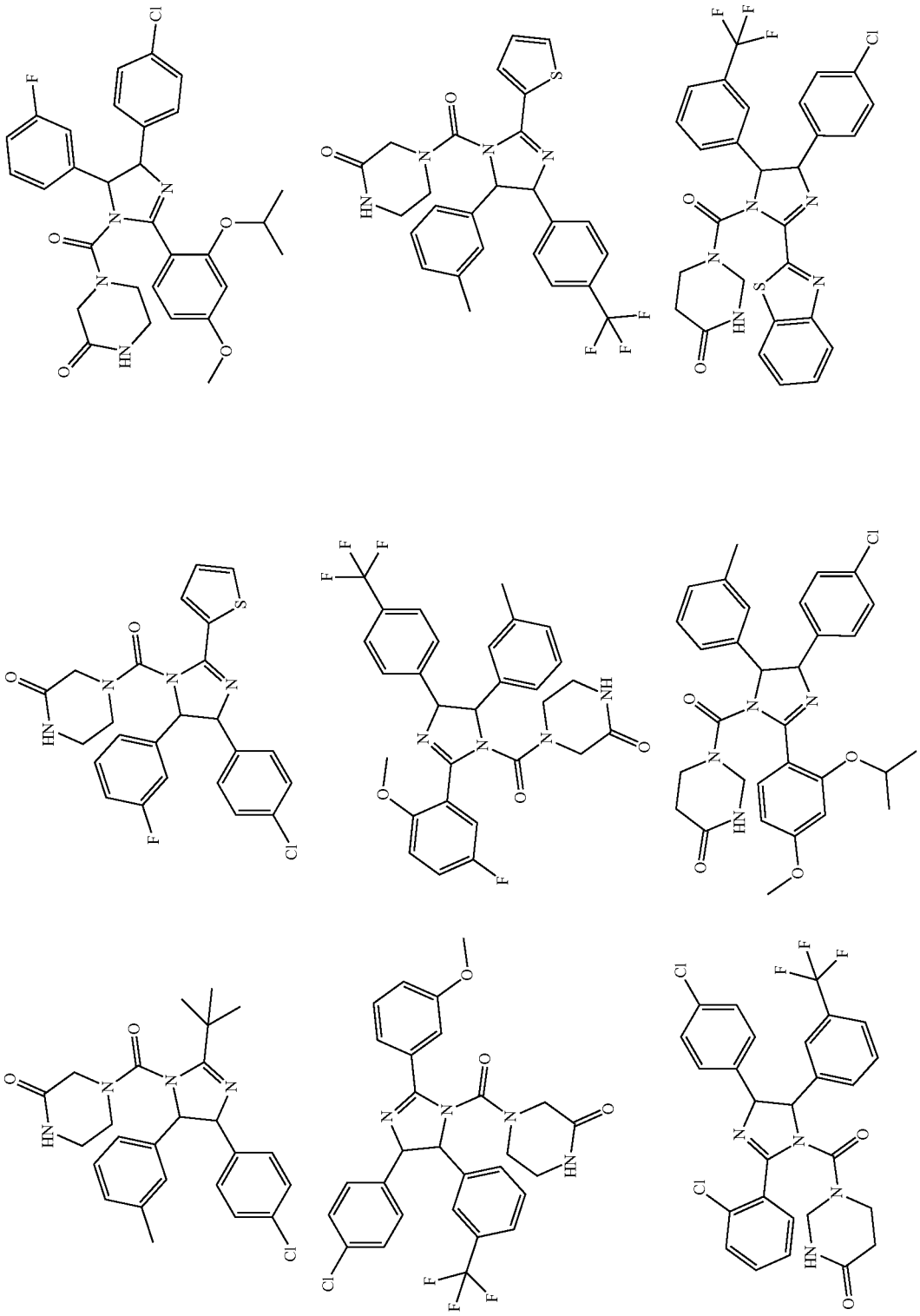

TABLE 4-continued
STRUCTURES OF 160 IMIDAZOLINE
ANALOGS SYNTHESIZED VIA PARALLEL APPROACH
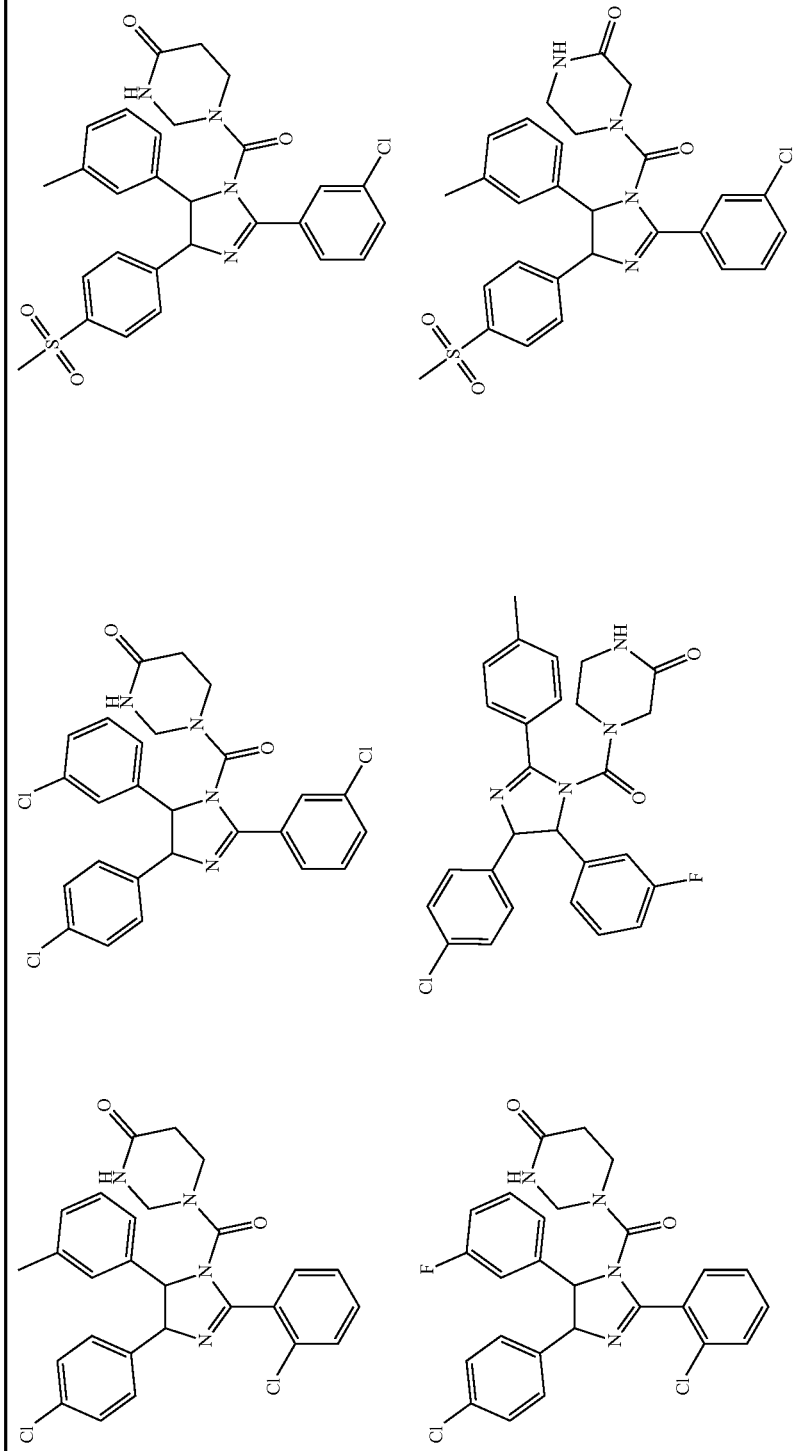

TABLE 4-continued
STRUCTURES OF 160 IMIDAZOLINE ANALOGS SYNTHESIZED VIA PARALLEL APPROACH
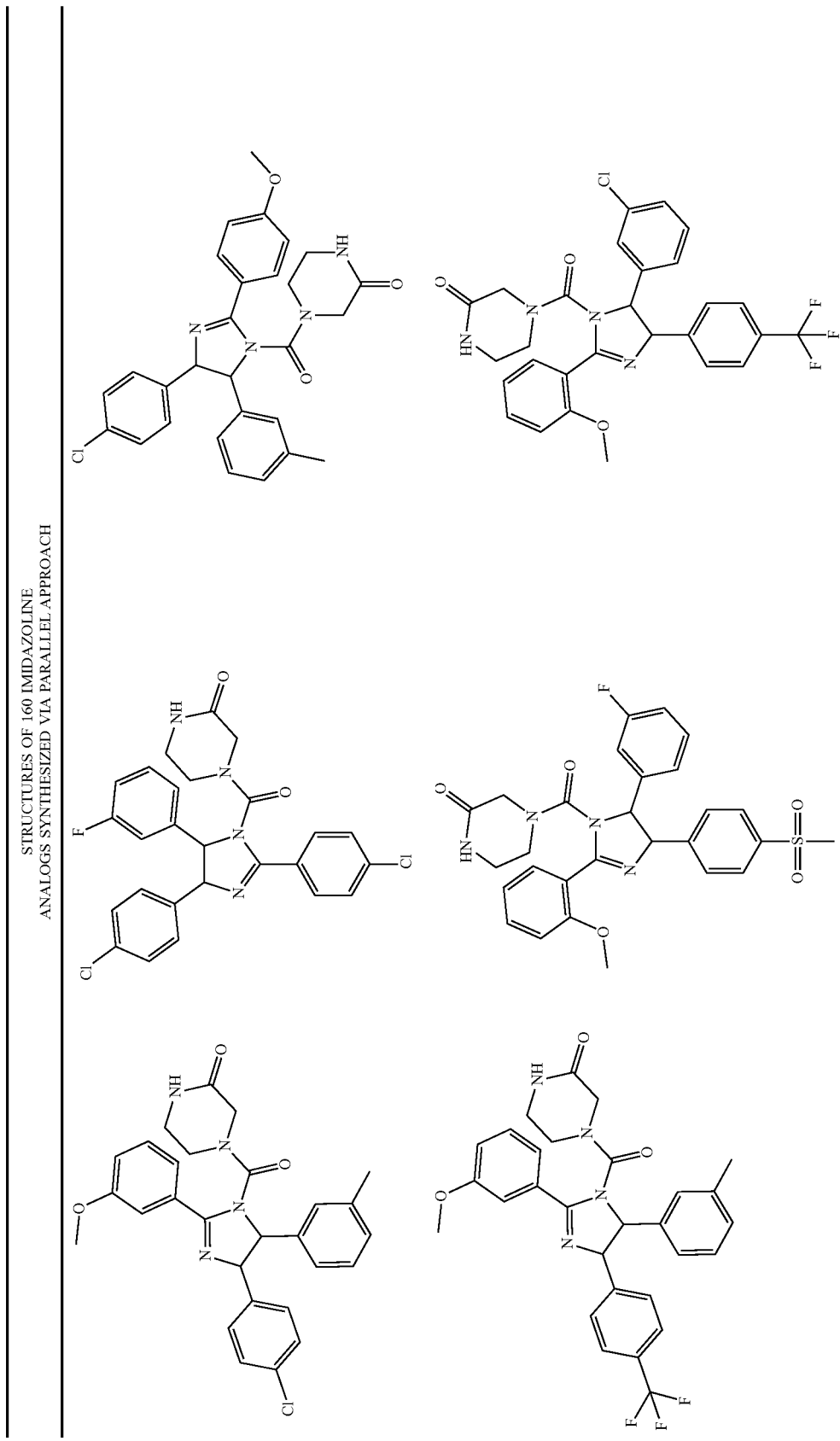

TABLE 4-continued
STRUCTURES OF 160 IMIDAZOLINE ANALOGS SYNTHESIZED VIA PARALLEL APPROACH
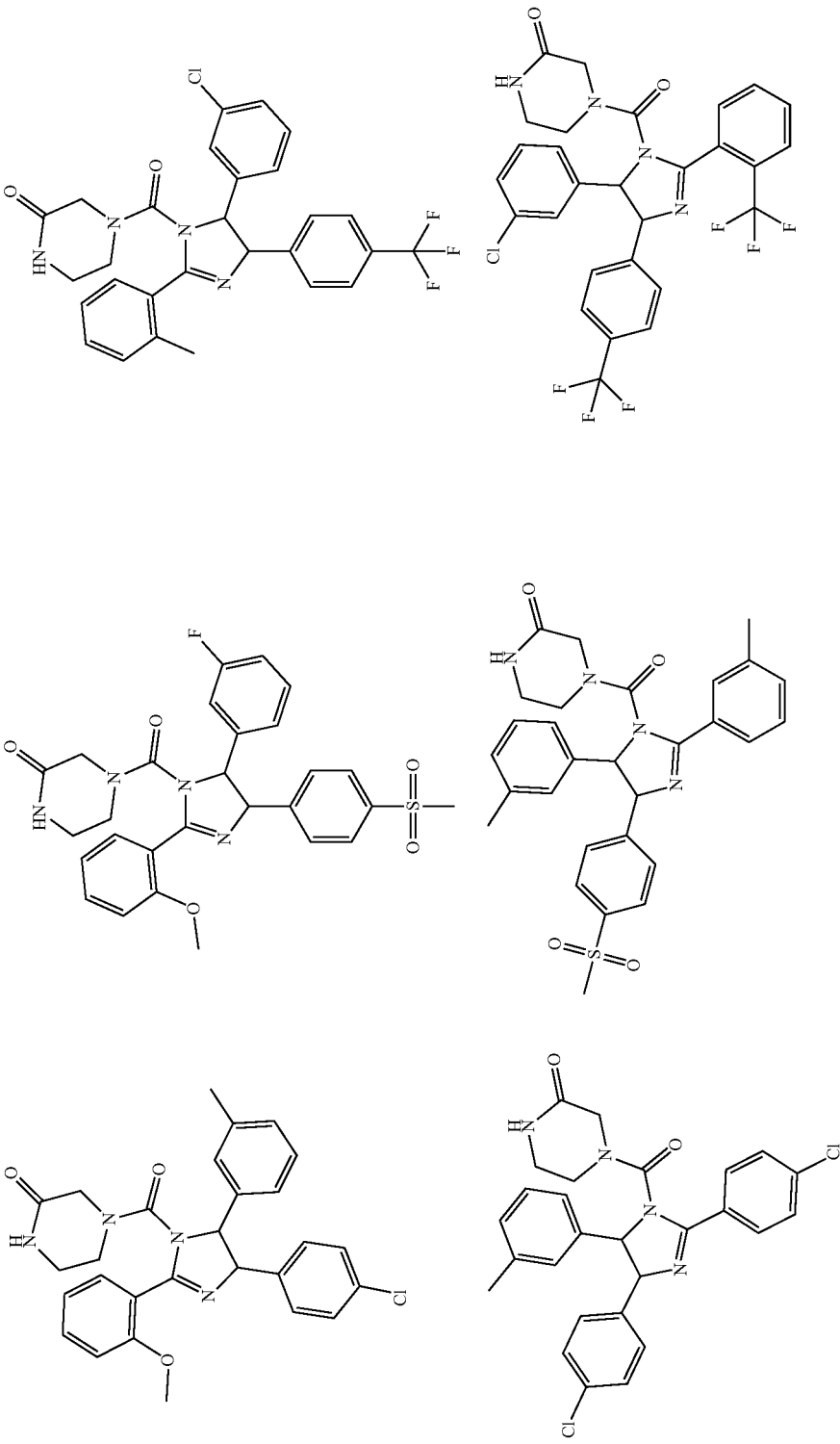

TABLE 4-continued
STRUCTURES OF 160 IMIDAZOLINE
ANALOGS SYNTHESIZED VIA PARALLEL APPROACH
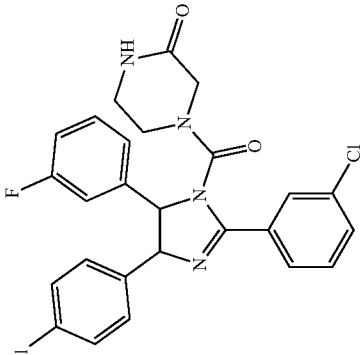
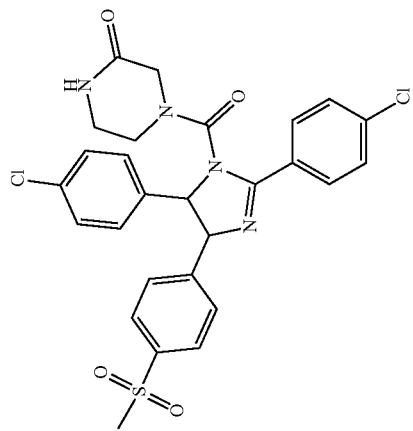
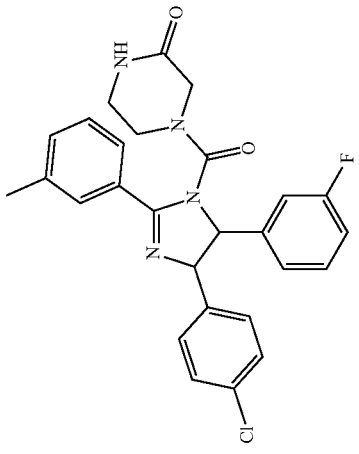
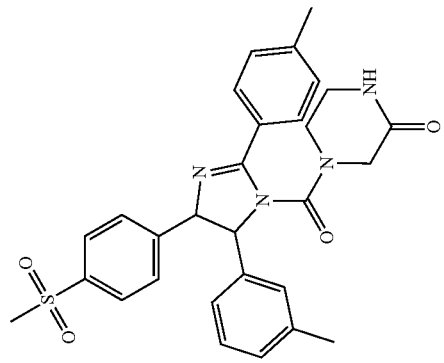
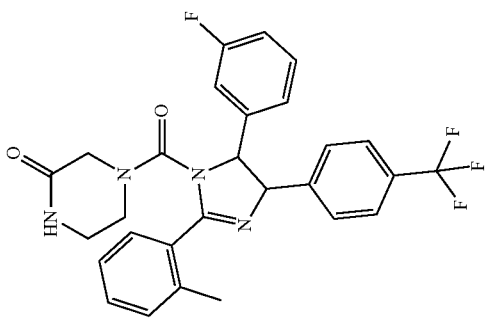
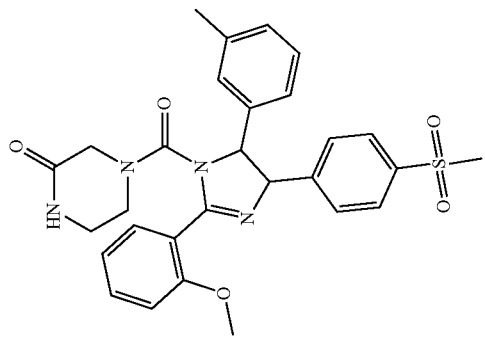

TABLE 4-continued
STRUCTURES OF 160 IMIDAZOLINE ANALOGS SYNTHESIZED VIA PARALLEL APPROACH
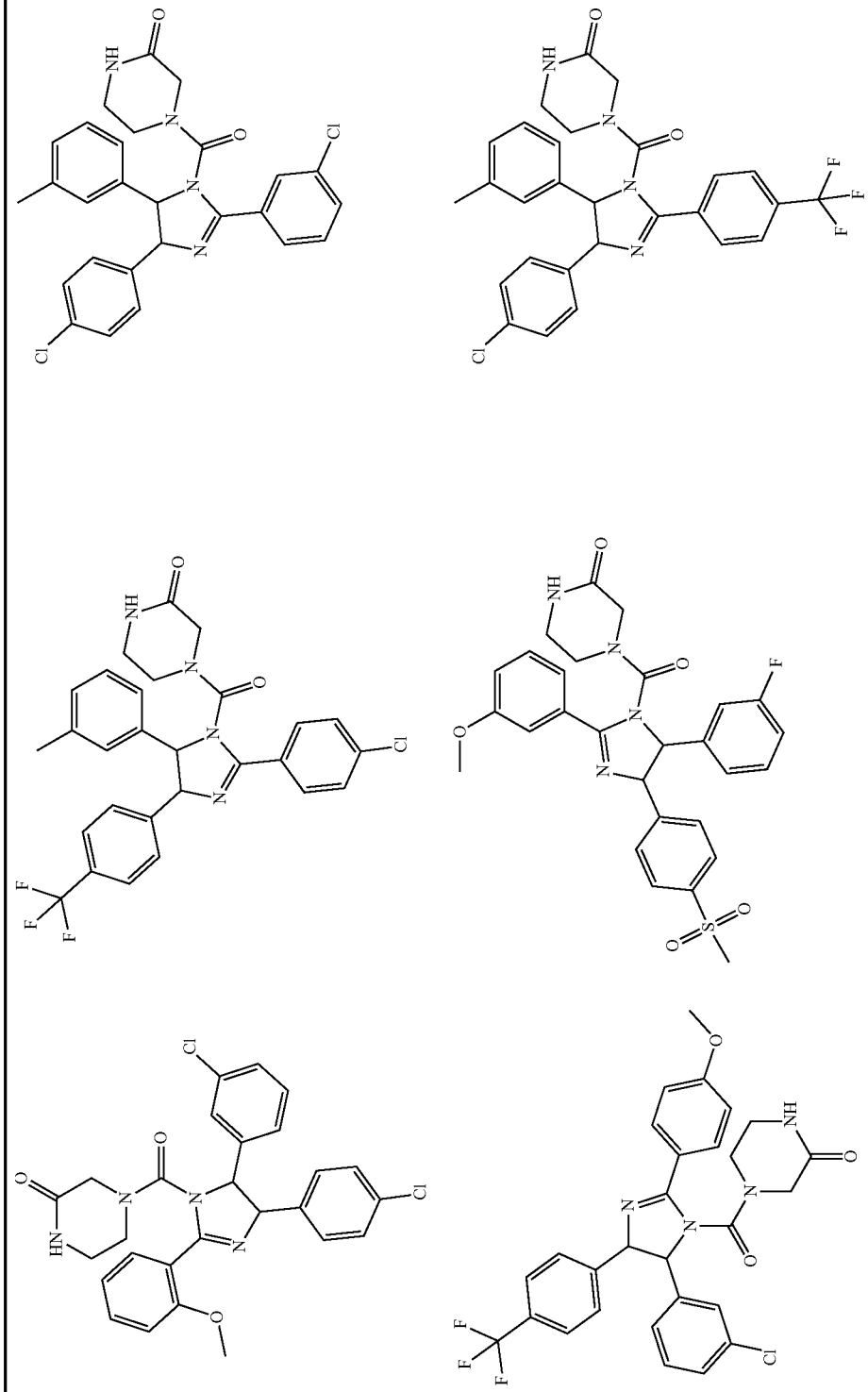

TABLE 4-continued
STRUCTURES OF 160 IMIDAZOLINE
ANALOGS SYNTHESIZED VIA PARALLEL APPROACH
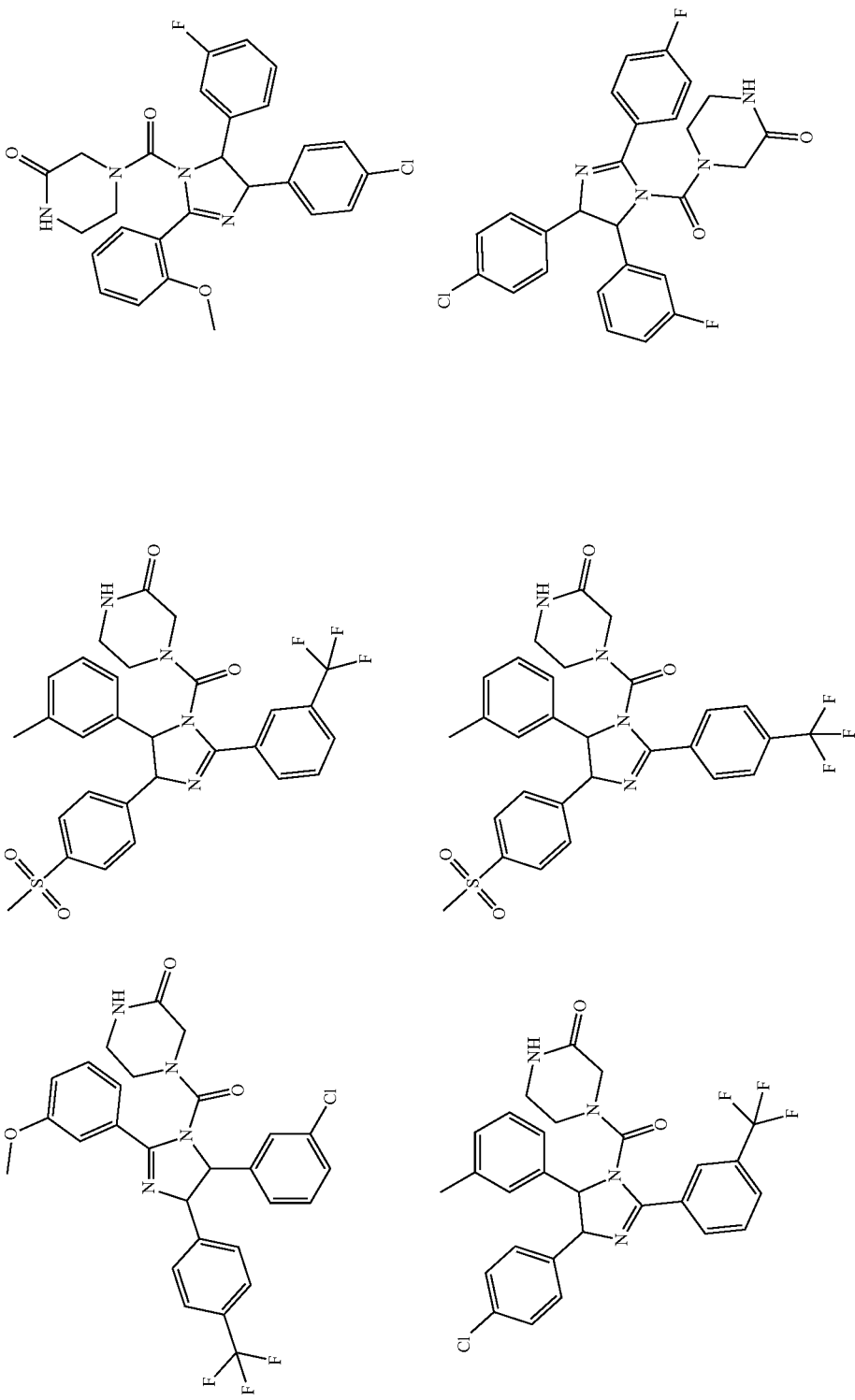

TABLE 4-continued
STRUCTURES OF 160 IMIDAZOLINE ANALOGS SYNTHESIZED VIA PARALLEL APPROACH
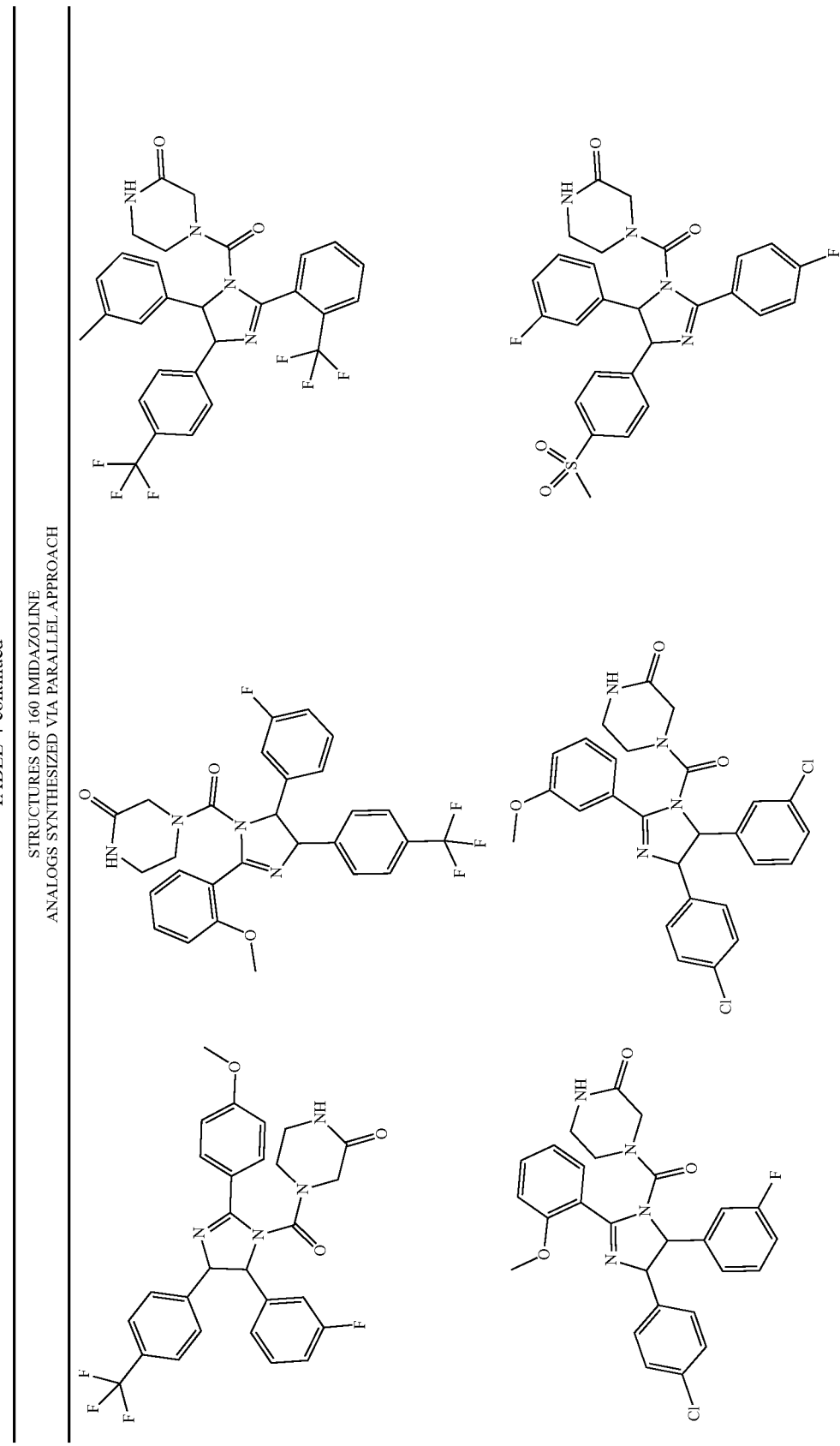

TABLE 4-continued
STRUCTURES OF 160 IMIDAZOLINE
ANALOGS SYNTHESIZED VIA PARALLEL APPROACH
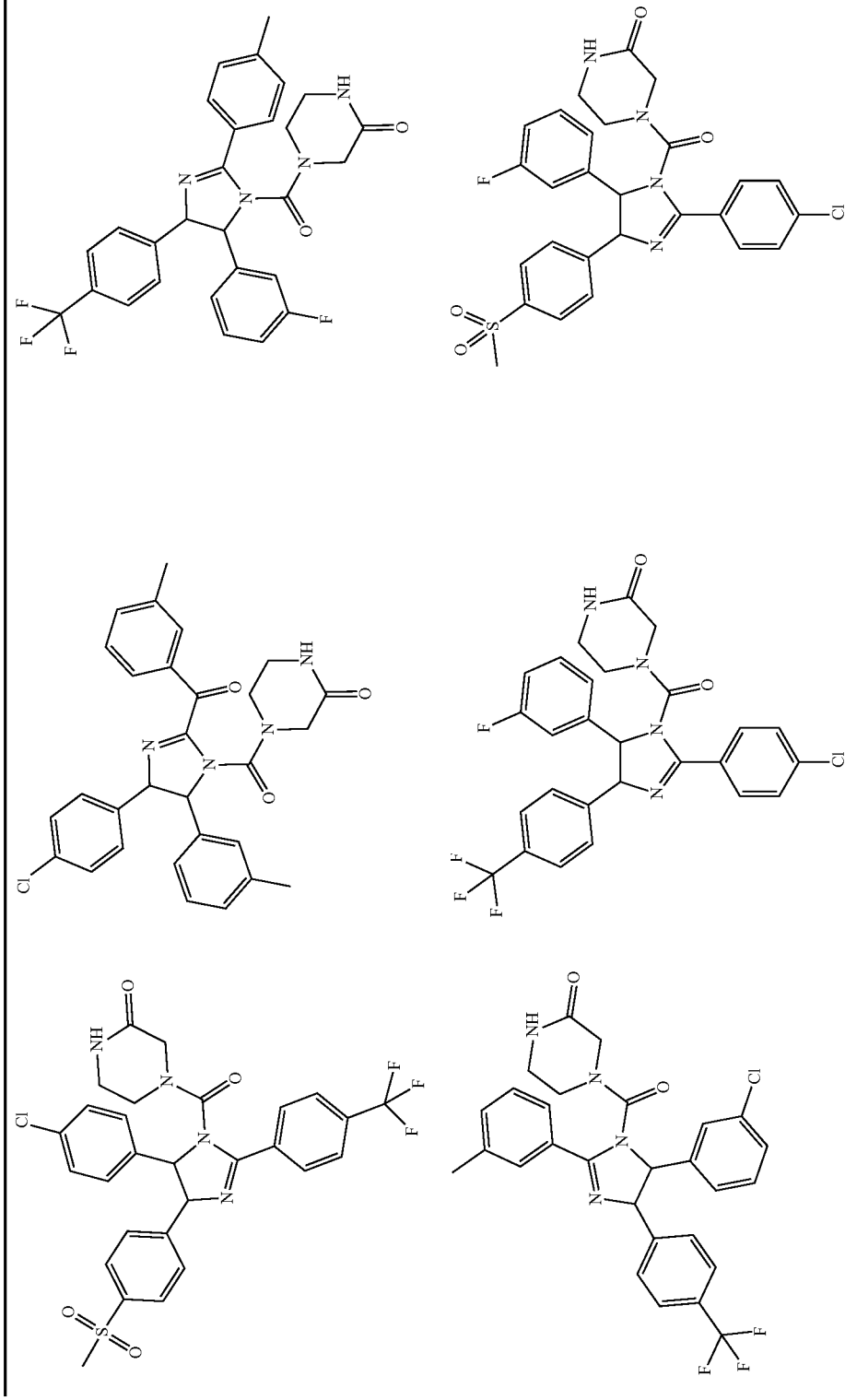

TABLE 4-continued
STRUCTURES OF 160 IMIDAZOLINE
ANALOGS SYNTHESIZED VIA PARALLEL APPROACH
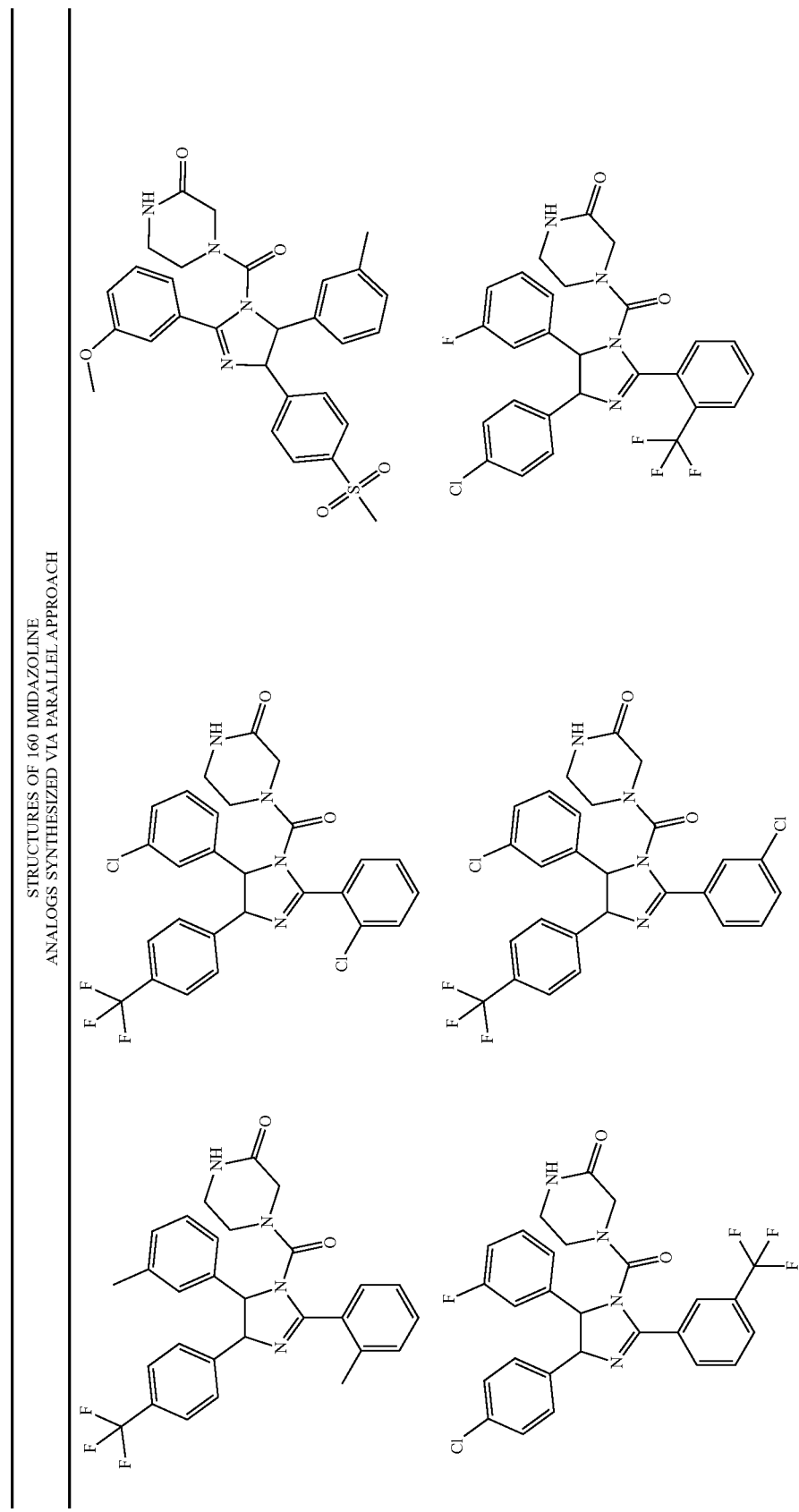

TABLE 4-continued
STRUCTURES OF 160 IMIDAZOLINE
ANALOGS SYNTHESIZED VIA PARALLEL APPROACH
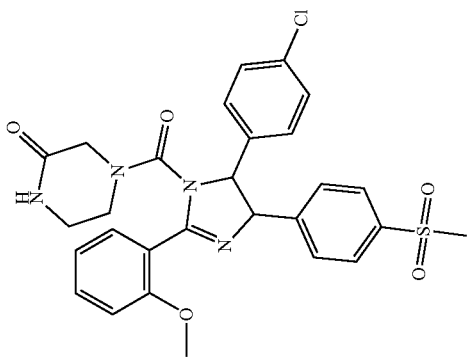
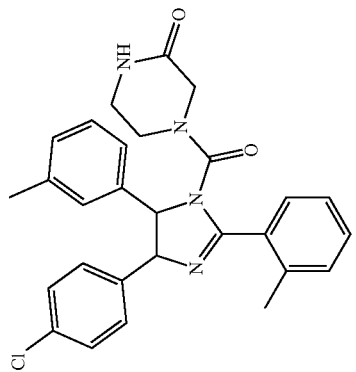
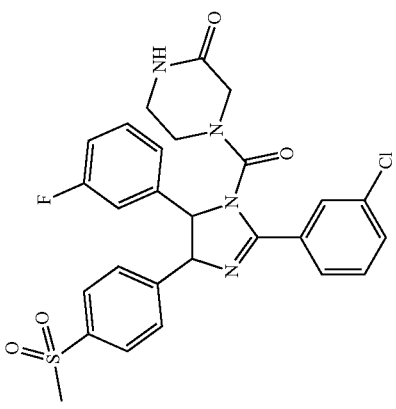
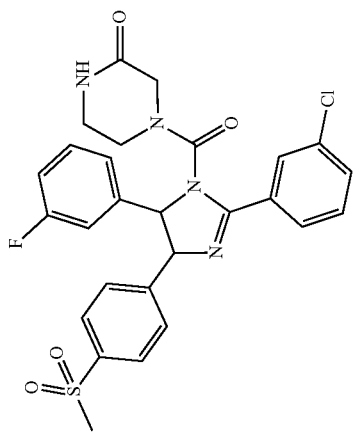
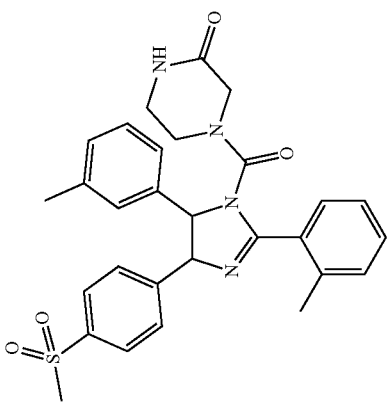
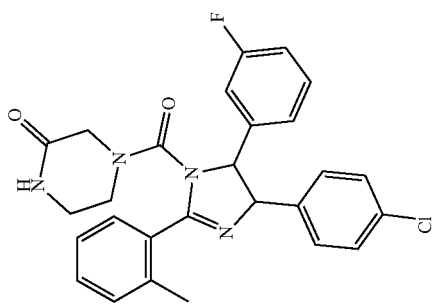

TABLE 4-continued
STRUCTURES OF 160 IMIDAZOLINE
ANALOGS SYNTHESIZED VIA PARALLEL APPROACH
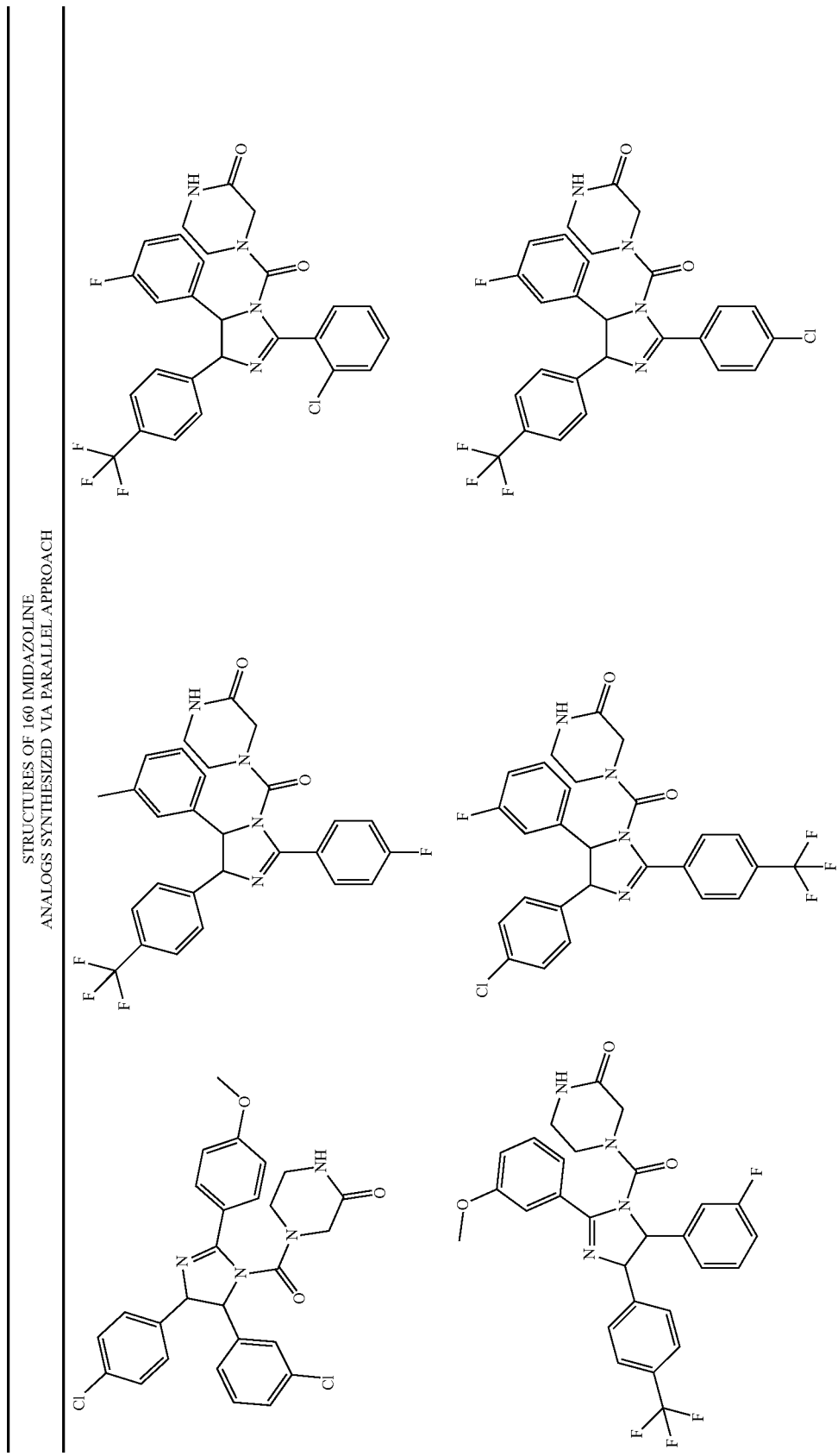

TABLE 4-continued
STRUCTURES OF 160 IMIDAZOLINE
ANALOGS SYNTHESIZED VIA PARALLEL APPROACH
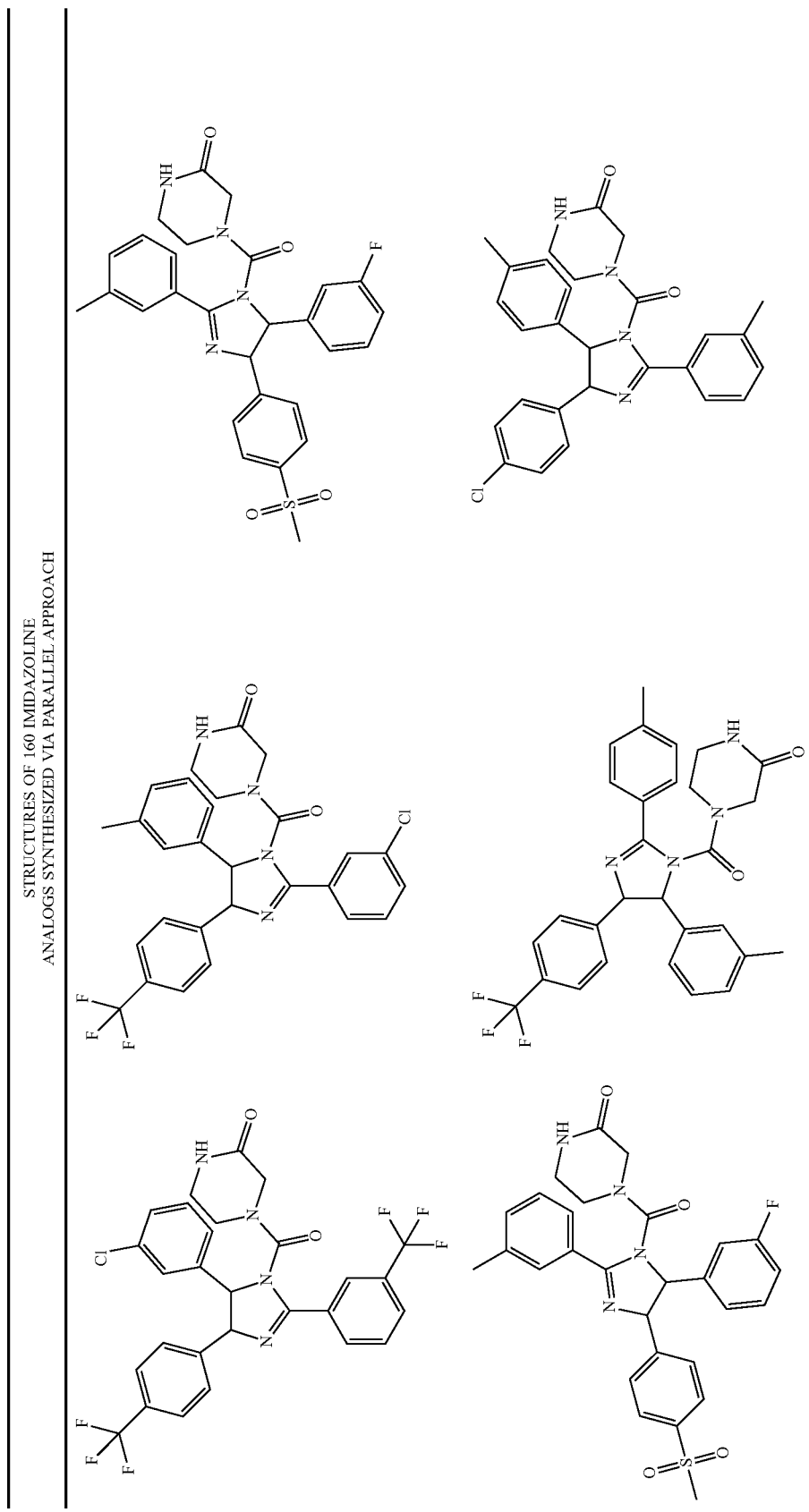

TABLE 4-continued
STRUCTURES OF 160 IMIDAZOLINE
ANALOGS SYNTHESIZED VIA PARALLEL APPROACH
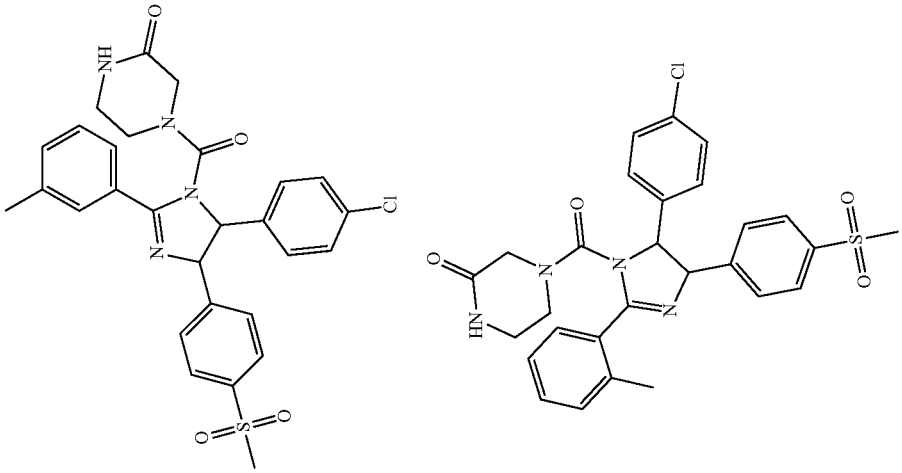
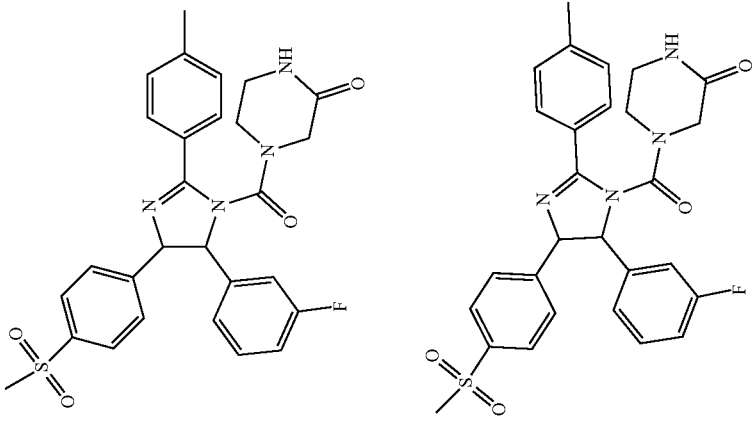
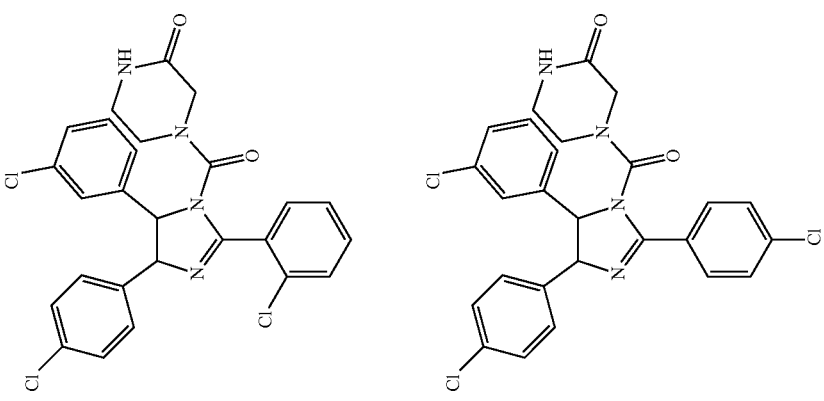

TABLE 4-continued
STRUCTURES OF 160 IMIDAZOLINE ANALOGS SYNTHESIZED VIA PARALLEL APPROACH
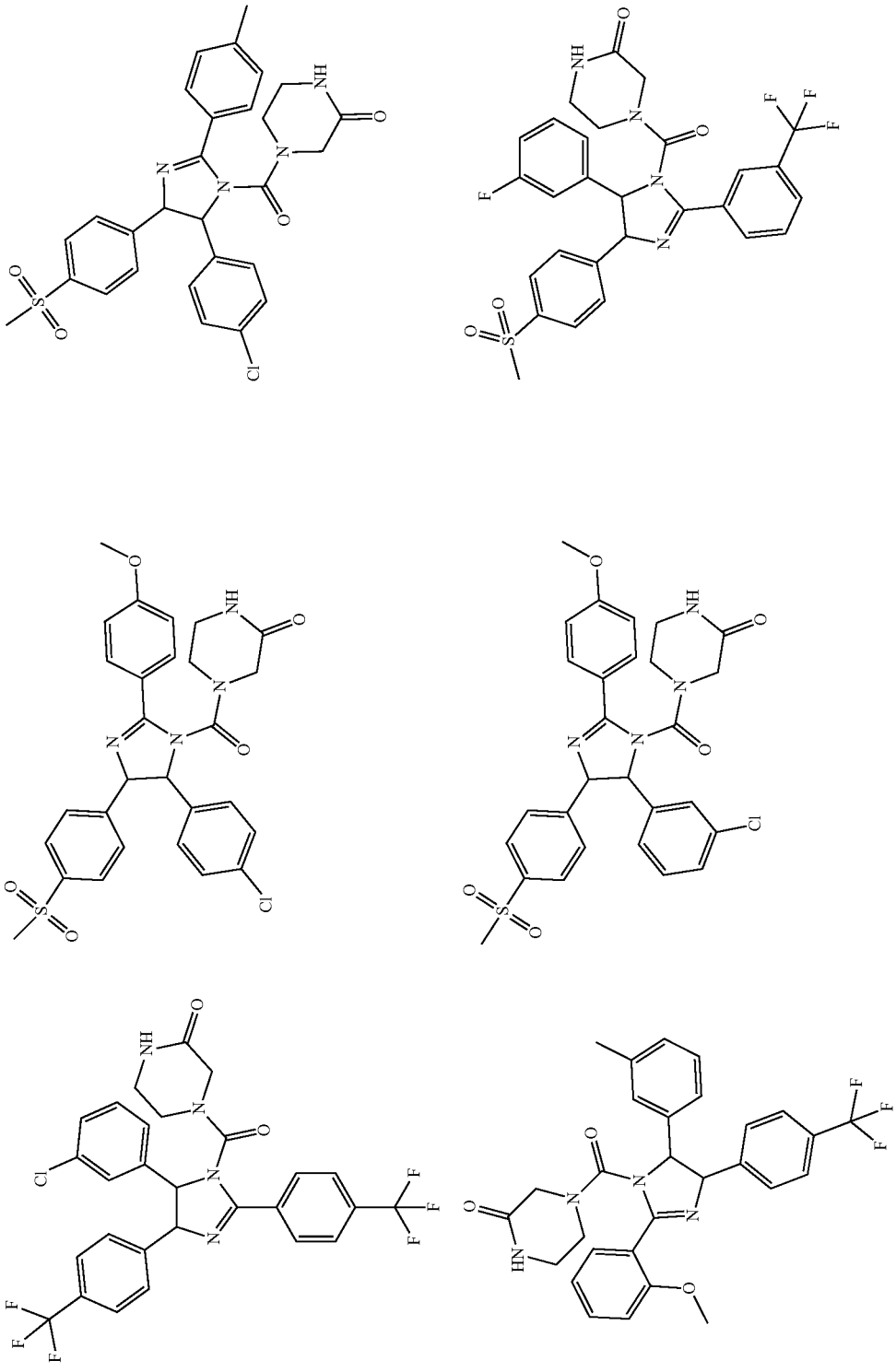

TABLE 4-continued
STRUCTURES OF 160 IMIDAZOLINE
ANALOGS SYNTHESIZED VIA PARALLEL APPROACH
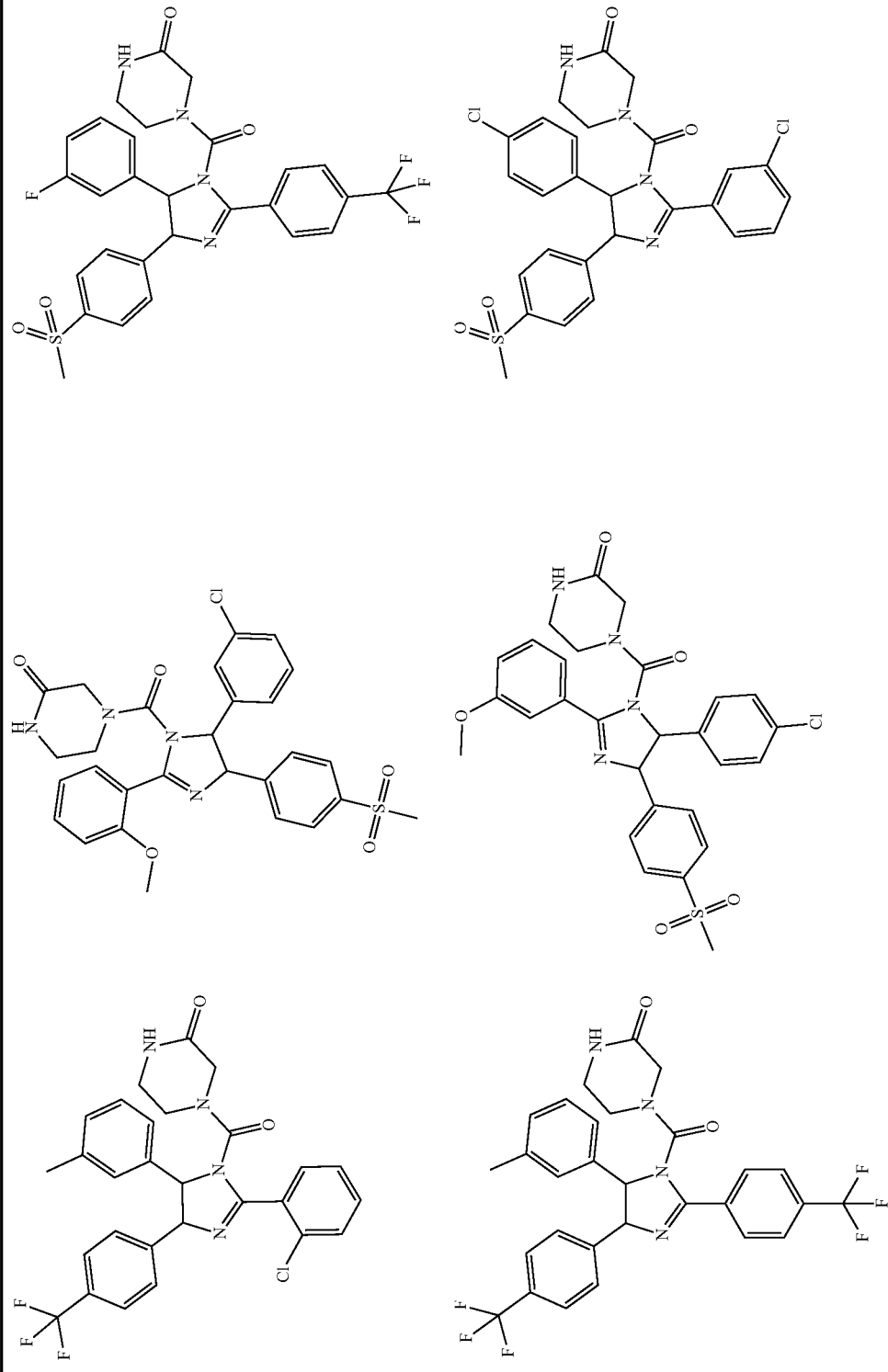

TABLE 4-continued
STRUCTURES OF 160 IMIDAZOLINE
ANALOGS SYNTHESIZED VIA PARALLEL APPROACH
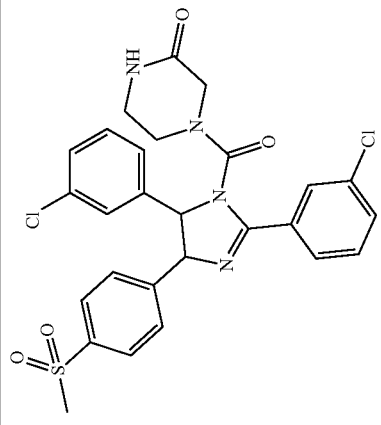

REFERENCES

1. U.S. Pat. No. 6,617,346 to Kong et al.
2. U.S. Pat. No. 6,734,302 to Kong et al.
3. U.S. Pat. No. 7,132,421 to Fotouhi et al.
4. U.S. Pat. No. 7,425,638 to Haley et al.
5. U.S. Patent Publication No. 2005/0282803 to Haley et al.
6. U.S. Patent Publication No. 2005/0288287 to Fotouhi et al.
7. U.S. Patent Publication No. 2006/0211693 to Fotouhi et al.
8. U.S. Patent Publication No. 2007/0129416 to Ding et al.
9. U.S. Patent Publication No. 2007/0167437 to Fotouhi et al.
10. Vassilev, Lyubomir T., et al., "In Vivo Activation of the p53 Pathway by Small-Molecule Antagonists of MDM2," Science 303, 844 (2004).
11. Laurie, Nikia A., et al., "Inactivation of the p53 pathway in retinoblastoma," Nature 444 (November, 2006).
12. Reed, Damon, et al., "Identification and Characterization of the First Small Molecule inhibitor of MDMX, The Journal of Biological Chemistry 285, No. 14, 10786-10796 (Apr. 2, 2010).

What is claimed is:

1. A compound having the formula:

[chemical structure]

wherein $Ar^1$ and $Ar^2$ are independently:

[chemical structure]

wherein $Ar^1$ and $Ar^2$ are different and have a cis relationship;
wherein $R^1$ is hydrogen;
wherein $R^2$ and $R^3$ are independently selected from halogen, methoxy, ethoxy, n-propoxyl, i-propoxyl, n-butoxyl, i-butoxyl, and t-butoxyl;
wherein $R^{4a}$-$R^{4e}$ are independently selected from hydrogen and halogen
or a pharmaceutically acceptable salt thereof.

2. The compound of claim 1, having the formula:

[chemical structure]

3. A pharmaceutical composition comprising, in a pharmaceutically acceptable carrier, a compound of claim 1 or a pharmaceutically acceptable salt thereof.

4. The pharmaceutical composition of claim 3, wherein the compound has the formula:

[chemical structure]

5. The compound of claim 1, wherein $R^2$ and $R^3$ are independently selected from halogen, methoxy, and i-propoxyl.

6. The compound of claim 1, wherein $R^{4a}$-$R^{4e}$ are independently selected from hydrogen, chloro, and bromo.

7. The compound of claim 1, wherein $R^2$ and $R^3$ are independently selected from halogen, methoxy, and i-propoxyl; and wherein $R^{4a}$-$R^{4e}$ are independently selected from hydrogen, chloro, and bromo.

8. The compound of claim 1, wherein $R^3$ is methoxy or chloro.

9. The compound of claim 1, wherein $R^2$ is i-propoxyl.

10. The compound of claim 1, wherein $Ar^e$ is 4-chlorophenyl.

11. The compound of claim 1, wherein AO is 4-bromophenyl.

12. The compound of claim 1, wherein AO is 3-chlorophenyl.

13. The compound of claim 1, wherein $R^3$ is methoxy, wherein $R^2$ is i-propoxyl, wherein $Ar^2$ is 4-chlorophenyl, and wherein $Ar^1$ is 4-bromophenyl.

14. The compound of claim 1, $R^3$ is chloro, wherein $R^2$ is i-propoxyl, $Ar^2$ is 4-chlorophenyl, and wherein $Ar^1$ is 3-chlorophenyl.

15. The pharmaceutical composition of claim 3, wherein $R^2$ and $R^3$ are independently selected from halogen, methoxy, and i-propoxyl.

16. The pharmaceutical composition of claim 3, wherein $R^{4a}$-$R^{4e}$ are independently selected from hydrogen, chloro, and bromo.

17. The pharmaceutical composition of claim 3, wherein $R^2$ and $R^3$ are independently selected from halogen, methoxy, and i-propoxyl; and wherein $R^{4a}$-$R^{4e}$ are independently selected from hydrogen, chloro, and bromo.

18. The pharmaceutical composition of claim 3, wherein $R^3$ is methoxy or chloro.

19. The pharmaceutical composition of claim 3, wherein $R^2$ is i-propoxyl.

20. The pharmaceutical composition of claim 3, wherein $Ar^2$ is 4-chlorophenyl.

21. The pharmaceutical composition of claim 3, wherein AO is 4-bromophenyl.

22. The pharmaceutical composition of claim 3, wherein AO is 3-chlorophenyl.

23. The pharmaceutical composition of claim 3, wherein $R^3$ is methoxy, wherein $R^2$ is i-propoxyl, wherein $Ar^2$ is 4-chlorophenyl, and wherein $Ar^1$ is 4-bromophenyl.

24. The pharmaceutical composition of claim 3, $R^3$ is chloro, wherein $R^2$ is i-propoxyl, $Ar^2$ is 4-chlorophenyl, and wherein $Ar^1$ is 3-chlorophenyl.

\* \* \* \* \*